(12) United States Patent
Oda et al.

(10) Patent No.: US 7,759,130 B2
(45) Date of Patent: Jul. 20, 2010

(54) MASS SPECTROMETRIC QUANTITATION METHOD FOR BIOMOLECULES BASED ON METABOLICALLY LABELED INTERNAL STANDARDS

(75) Inventors: Yoshiya Oda, Tsukuba (JP); Yasushi Ishihama, Tsukuba (JP); Tsuyoshi Tabata, Tsukuba (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 1033 days.

(21) Appl. No.: 10/579,780

(22) PCT Filed: Nov. 22, 2004

(86) PCT No.: PCT/JP2004/017370

§ 371 (c)(1),
(2), (4) Date: May 18, 2006

(87) PCT Pub. No.: WO2005/050188

PCT Pub. Date: Jun. 2, 2005

(65) Prior Publication Data

US 2007/0134806 A1 Jun. 14, 2007

(30) Foreign Application Priority Data

Nov. 21, 2003 (JP) ............................. 2003-392690
Apr. 2, 2004 (JP) ............................. 2004-109845

(51) Int. Cl.
*G01N 24/00* (2006.01)

(52) U.S. Cl. ............................. 436/173; 436/8; 436/13; 436/14; 436/15

(58) Field of Classification Search ....................... None
See application file for complete search history.

(56) References Cited

U.S. PATENT DOCUMENTS 6,300,626 B1 * 10/2001 Brock et al. .................. 250/287
6,391,649 B1   5/2002 Chait et al. .................. 436/173

(Continued)

FOREIGN PATENT DOCUMENTS

JP    P 2000-131305 A    12/2000

(Continued)

OTHER PUBLICATIONS

Zhong et al. Two-Dimensional Mass Spectra Generated from the Analysis of 15N-Labeled and Unlabeled Peptides for Efficient Protein Identification and de novo Peptide Sequencing, (J. Proteom. Research, 2004, v. 3, pp. 1155-1163.*

(Continued)

*Primary Examiner*—Yelena G Gakh
(74) *Attorney, Agent, or Firm*—Morgan Lewis & Bockius LLP

(57) ABSTRACT

An object of the present invention is to quantitate with good accuracy, furthermore, quantitate absolutely, one or a plurality of biological molecules in a sample such as a tissue, a biological fluid, a cell, a cell organ or protein complex.

By adding a metabolically isotope labeled biological molecule as an internal standard substance and measuring with a mass spectrometer, quantitating with good accuracy one or a plurality of target molecules in a sample has become possible. In addition, by performing waveform separation processing during mass analysis, a highly accurate quantitative analysis method of mass analysis is provided.

8 Claims, 27 Drawing Sheets

U.S. PATENT DOCUMENTS

| | | | |
|---|---|---|---|
| 2002/0076739 | A1 | 6/2002 | Aebersold et al. |
| 2002/0123055 | A1 | 9/2002 | Estell |

FOREIGN PATENT DOCUMENTS

| | | |
|---|---|---|
| JP | 2002-333430 | 11/2002 |
| JP | A-2003-107066 | 4/2003 |
| JP | P 2003-107066 A | 9/2003 |
| JP | A-2000-131305 | 5/2006 |
| WO | WO 03/016861 | 2/2003 |

OTHER PUBLICATIONS

Wu et al. "Metabolic Labeling of Mammalian Organisms with Stable Isotopes for Quantitative Proteomic Analysis", Anal. Chem., Jun. 23, 2004.*

Supplementary European Search Report, EP 04 81 9013.6, dated Feb. 10, 2009.

Stable Isotope Labeling by Amino Acids in Cell Culture, SILAC, as a Simple and Accurate Approach to Expression Proteomics, Shao-En Ong et al., 2002, The American Society for Biochemistry and Molecular Biology, Inc., pp. 376-386.

Absolute quantification of proteins and phosphoproteins from cell lysates by tandem MS, Scott A. Gerber et al., Department of Cell Biology, Harvard Medical School, Proceedings of the National Academy of Science, vol. 100, No. 12, Jun. 10, 2003, pp. 6940-6945.

Quantitation of peptides and proteins by matrix-assisted laser desorption/ionization mass spectrometry using $^{18}$O-labeled internal standards, Olga A. Mirgorodskaya et al., Rapid Communication in Mass Spectrometry, 200, vol. 14, 1, Jan. 1, 2000, pp. 1226-1232.

Quantitative Profiling of Proteins in Complex Mixtures Using Liquid Chromatography and Mass Spectrometry, Dirk Chelius et al. Journal of Proteome Research, vol. 1, No. 4, 2002, pp. 317-323.

Proteomic Tools for Quantitation by Mass Spectrometry, Jennie Lill, Mass Spectrometry Review, vol. 22, No. 3, May 2003, pp. 182-194.

Edwin P. Romijn, et al., "Recent Liquid Chromatographic-(tande,m) mass spectrometric applications in proteomics", Journal of Chromatography A, Jun. 6, 2003; vol. 1000, No. 1/2, pp. 589-608.

"Post-Genomic Mass Spectrometry" 1993, pp. 39-72, Toshimitsu Niwa Ed., Kagalcudojin (English translation of abstract enclosed).

Cagney et al. "De novo peptide sequencing and quantitative profiling of complex protein mixtures using mass-coded abundance tagging" Nat Biotechnol. Feb. 2002;20(2):163-170.

Drewes et al. "Global approaches to protein-protein interactions" Curr Opin Cell Biol. Apr. 2003;15(2):199-205.

Gavin et al. "Protein complexes and proteome organization from yeast to man" Curr Opin Chem Biol. Feb. 2003;7(1):21-27.

Gerber et al. "Absolute quantification of proteins and phosphoproteins from cell lysates by tandem MS" Proc Natl Acad Sci U S A. Jun. 10, 2003;100(12):6940-6945. Epub May 27, 2003.

Goodlett et al. "Differential stable isotope labeling of peptides for quantitation and de novo sequence derivation" Rapid Commun Mass Spectrom. 2001;15(14):1214-1221.

Griffin et al. "Toward a high-throughput approach to quantitative proteomic analysis: expression-dependent protein identification by mass spectrometry" J Am Soc Mass Spectrom. Dec. 2001;12(12):1238-1246.

Gygi et al. "Quantitative analysis of complex protein mixtures using isotope-coded affinity tags" Nat Biotechnol. Oct. 1999;17(10):994-999.

Han et al. "Quantitative profiling of differentiation-induced microsomal proteins using isotope-coded affinity tags and mass spectrometry" Nat Biotechnol. Oct. 2001;19(10):946-951.

Ishihama et al. "Simple and sensitive quantitation method for mevalonic acid in plasma using gas chromatography/mass spectrometry" Rapid Commun Mass Spectrom. May 1994;8(5):377-380.

Kahn "From genome to proteome: looking at a cell's proteins" Science. Oct. 20, 1995;270(5235):369-370.

Matsui et al. "Direct determination of E2020 enantiomers in plasma by liquid chromatography-mass spectrometry and column-switching techniques" J Chromatogr A. Mar. 3, 1995;694(1):209-218.

Matsui et al. "Simultaneous determination of donepezil (aricept) enantiomers in human plasma by liquid chromatography-electrospray tandem mass spectrometry" J Chromatogr B Biomed Sci Appl. Jun. 11, 1999;729(1-2):147-155.

Neubauer et al. "Mass spectrometry and EST-database searching allows characterization of the multi-protein spliceosome complex" Nat Genet. Sep. 1998;20(1):46-50.

Oda et al. "Accurate quantitation of protein expression and site-specific phosphorylation" Proc Natl Acad Sci U S A. Jun. 8, 1999;96(12):6591-6596.

Oda et al. "Quantitation of platelet-activating factor in biological samples using liquid chromatography/mass spectrometry with column-switching technique" Anal Biochem. Oct. 10, 1995;231(1):141-150.

Ong et al. "Mass spectrometric-based approaches in quantitative proteomics" Methods. Feb. 2003;29(2):124-130.

Ono et al. "Clinical and experimental studies on the role of platelet-activating factor (PAF) in the pathogenesis of septic DIC" Surg Today. 1993;23(3):228-233.

Romijn et al. "Recent liquid chromatographic-(tandem) mass spectrometric applications in proteomics" J Chromatogr A. Jun. 6, 2003;1000(1-2):589-608.

Sechi "A method to identify and simultaneously determine the relative quantities of proteins isolated by gel electrophoresis" Rapid Commun Mass Spectrom. 2002;16(15):1416-1424.

Sechi et al. "Modification of cysteine residues by alkylation. A tool in peptide mapping and protein identification" Anal Chem. Dec. 15, 1998;70(24):5150-5158.

Sechi et al. "Quantitative proteomics using mass spectrometry" Curr Opin Chem Biol. Feb. 2003;7(1):70-77.

Smolka et al. "Quantitative protein profiling using two-dimensional gel electrophoresis, isotope-coded affinity tag labeling, and mass spectrometry" Mol Cell Proteomics. Jan. 2002;1(1):19-29.

Wigge et al. "Analysis of the Saccharomyces spindle pole by matrix-assisted laser desorption/ionization (MALDI) mass spectrometry" J Cell Biol. May 18, 1998;141(4):967-977.

Yao et al. "Proteolytic 18O labeling for comparative proteomics: model studies with two serotypes of adenovirus" Anal Chem. Jul. 1, 2001;73(13):2836-2842.

Yodosha "Proteome analysis method" printed Jul. 10, 2000 pp. 111-122 (English translation of abstract enclosed).

Zhou et al. "Quantitative proteome analysis by solid-phase isotope tagging and mass spectrometry" Nat Biotechnol. May 2002;20(5):512-515.

* cited by examiner

FIG.27

| PEPTIDE SEQUENCE (PROTEIN NAME) | Wild PEAK INTENSITY RATIO/KNOCK OUT PEAK INTENSITY RATIO *LABELED MOLECULE WITH THE SAME SEQUENCE WAS USED AS THE INTERNAL STANDARD | Wild PEAK INTENSITY RATIO/KNOCK OUT PEAK INTENSITY RATIO **LABELED MOLECULE WITH A DIFFERENT SEQUENCE WAS USED AS THE INTERNAL STANDARD |
|---|---|---|
| SEQUENCE NO.1: AHQLVMEGYNWCHDR (protein phosphatase 2a) SEE FIG. 10 | 2.92/3.09=0.95 | 2.81/3.82=0.74 LABELED MOLECULE WITH THE SEQUENCE NO. 2 WAS USED AS THE INTERNAL STANDARD |
| SEQUENCE NO.2: HHITPLLSAVYEGHVSCVK (myotrophin) SEE FIG. 10 | 2.85/3.97=0.72 | 2.96/3.21=0.92 LABELED MOLECULE WITH THE SEQUENCE NO. 1 WAS USED AS THE INTERNAL STANDARD |
| SEQUENCE NO.3: HFSVEGGQLEFR (heat shock protein 1) SEE FIG. 11 | 0.45/0.46=0.97 | 2.58/3.03=0.85 LABELED MOLECULE WITH THE SEQUENCE NO. 4 WAS USED AS THE INTERNAL STANDARD |
| SEQUENCE NO.4: AISHEHSPSDLEAHFVPLVK (protein phosphatase PP2A) SEE FIG. 11 | 2.35/2.14=1.10 | 0.41/0.33=1.23 LABELED MOLECULE WITH THE SEQUENCE NO. 3 WAS USED AS THE INTERNAL STANDARD |
| SEQUENCE NO.5: VIHDNFGIVEGLMTTVHAIT ATQK (glyceraldehyde-3-phosphate de hydrogenase) SEE FIG. 12 | 1.18/0.73=1.61 | 1.86/2.07=0.90 LABELED MOLECULE WITH THE SEQUENCE NO. 6 WAS USED AS THE INTERNAL STANDARD |
| SEQUENCE NO.6: HYFQNTQNTQGLIFVVDSNDR (ADP-ribosylation factor) SEE FIG. 12 | 1.84/1.86=0.99 | 0.89/1.18=0.75 LABELED MOLECULE WITH THE SEQUENCE NO. 5 WAS USED AS THE INTERNAL STANDARD |
| SEQUENCE NO.7: YALYDATYETK (cofilin) SEE FIG. 13 | 2.17/2.60=0.83 | 10.8/9.2=1.17 LABELED MOLECULE WITH THE SEQUENCE NO. 8 WAS USED AS THE INTERNAL STANDARD |
| SEQUENCE NO.8: FPGQLNADLR (tubulin, beta) SEE FIG. 13 | 11.38/9.4=1.21 | 2.28/2.66=0.86 LABELED MOLECULE WITH THE SEQUENCE NO. 7 WAS USED AS THE INTERNAL STANDARD |

FIG.28

| SEQUENCE | QUANTITATION NUMBER |
|---|---|
| ALVLELCCNDESGEDVEVPYVR | 1.51091043 |
| KPLLESGTLGTK | 1.351344211 |
| NFPNAIEHTLQWAR | 0.379425372 |
| NFPNAIEHTLQWAR | 1.006616361 |
| NFPNAIEHTLQWAR | 0.498511448 |
| NFPNAIEHTLQWAR | 0.620944209 |
| NFPNAIEHTLQWAR | 0.744001926 |
| NFPNAIEHTLQWAR | 0.39584672 |
| NFPNAIEHTLQWAR | 0.569211695 |
| NFPNAIEHTLQWAR | 0.682017147 |
| NFPNAIEHTLQWAR | 0.362867677 |
| NFPNAIEHTLQWAR | 1.20440506 |
| NFPNAIEHTLQWAR | 1.443092102 |
| NFPNAIEHTLQWAR | 0.767798114 |
| NFPNAIEHTLQWAR | 1.736296952 |
| NFPNAIEHTLQWAR | 0.2713649 |
| NFPNAIEHTLQWAR | 2.245947181 |
| NFPNAIEHTLQWAR | 3.110330946 |
| NFPNAIEHTLQWAR | 0.251063062 |
| YFLVGAGAIGCELLK | 21.56982391 |
| YFLVGAGAIGCELLK | 0.651272581 |
| YFLVGAGAIGCELLK | 8.513072128 |
| YFLVGAGAIGCELLK | 5.037104157 |

FIG.29

SEARCH TARGET : ALVLELCCNDESGEDVEVPYVR

IDENTIFIED PROTEINS :

gi | 23510340 | ref | NP_695012.1 |
    gi | 35830 | emb | CAA40296.1 |
    gi | 24485 | emb | CAA37078.1 |

SEARCH TARGET : KPLLESGTLGTK

IDENTIFIED PROTEINS :

gi | 23510340 | ref | NP_695012.1 |
    gi | 35830 | emb | CAA40296.1 |
    gi | 24485 | emb | CAA37078.1 |

SEARCH TARGET : NFPNAIEHTLQWAR

IDENTIFIED PROTEINS :

gi | 23510340 | ref | NP_695012.1 |
    gi | 35830 | emb | CAA40296.1 |
    gi | 24485 | emb | CAA37078.1 |

SEARCH TARGET : YFLVGAGAIGCELLK

IDENTIFIED PROTEINS :

gi | 23510340 | ref | NP_695012.1 |
    gi | 35830 | emb | CAA40296.1 |
    gi | 24485 | emb | CAA37078.1 |

FIG.30A gi | 23510340 | ref | NP_695012.1 |
gi | 35830 | emb | CAA40296.1 |
gi | 24485 | emb | CAA37078.1 |

FIG.30B official_symbol : UBE1 product : ubiquitin-activating enzyme E1 go(molecular function) :

ATP binding.
    ligase activity.
    ubiquitin activating enzyme activity.

go(biological process) :

DNA replication.
    ubiquitin cycle.

MASS SPECTROMETRIC QUANTITATION METHOD FOR BIOMOLECULES BASED ON METABOLICALLY LABELED INTERNAL STANDARDS

TECHNICAL FIELD

The present invention relates to a method for quantitating one or a plurality of biological molecules in a sample by adding to the sample an internal standard substance that is a metabolically isotope labeled biological molecule, or a cell containing an internal standard substance that is a metabolically isotope labeled biological molecule, and measuring with a mass spectrometer.

In addition, the present invention relates to a quantitative analysis method for a biological molecule; more specifically, the present invention relates to an analysis method using an isotope labeled biological molecule and to a program for this analysis.

BACKGROUND ART

A genome is the total DNA contained in one cell, containing the entirety of the genes and the intergenic regions of a living organism, and organisms known to us are defined by the genome. Currently, reading of the human nucleotide sequences has already been completed, and the number of genes is being predicted. However, nucleotide sequence information is not sufficient to elucidate biological phenomena, and although the total genomes of *Escherichia coli*, yeast, *Caenorhabditis elegans*, drosophila and the like have actually been elucidated, it does not mean that the entirety of the gene function of these model living organisms has been elucidated.

Proteomics is an important item in the post-genomic era, and this technology is gathering attention from the perspective of carrying out functional analysis of genes. Owing to the current proteome technology, that is to say, a mass spectroscopic device, a database, and a search engine linking these, the ease with which a protein is identified has leaped forward, allowing a specific protein mixture (for instance, a protein complex) to be identified comprehensively (for example, see Non-patent References 1 to 4). However, merely identifying a protein, or merely elucidating a component, is insufficient as functional analysis. The reason is, a proteome being dynamic, the expression state thereof varies depending on the timing or the location. Therefore, carrying out an analysis of the variation of an individual protein should allow the advantages of proteomics to be exploited. Thus, similarly to Differential Display in a DNA chip, a Differential Display at the protein level is created also in proteome, and a variety of attempts to capture the variation of individual protein level are carried out.

Two-dimensional electrophoresis is routinely used as means for proteome analysis; however, with such a method that compares spots of protein stained on a gel, comparing accurately the quantity of individual protein present in two samples to be compared is extremely difficult. The reasons being, issues exist in:

1. reproducibility of extraction from cell and reproducibility due to pretreatment manipulation such as cell fractionation/crude purification
2. reproducibility of protein separation in two-dimensional electrophoresis and the like
3. reproducibility of gel staining and the like; furthermore,
4. when a plurality of proteins are mixed in one spot/band, the quantitative aspect with respect to an individual protein is lost.

Thus, currently, capturing a small variation is difficult with a pattern comparison by gel staining, except when the expression amount varies dramatically, i.e., 10 to 100 times or more.

In addition, even if a dramatic variation is detected in this way, by merely comparing a spot on a gel, the protein corresponding to this spot remains unidentified, and the target spot must be cut out from the gel and protein identification work be carried out with a mass spectroscopic device.

Obtaining quantitative data in an analysis by the mass spectroscopic device necessarily requires correction with an internal standard substance, as reproducibility of ionization rate is poor. In addition, the quantitative value varies exceedingly for each experiment due to the pretreatment procedure (extraction, derivatization, separation and the like) up to the analysis with the mass spectroscopic device. Thus, by pre-adding to a sample an internal standard substance obtained by labeling with a stable isotope a target low molecular weight substance, protein or the like, all these corrections has become possible, and improvement of quantitation accuracy has kept forward. Quantitative analysis is carried out in a drug, a lipid, a protein or the like, using an internal standard substance labeled with a stable isotope element (for example, see Non-patent References 5 to 10).

The aforementioned quantitation of a low molecular substance such as a drug or a lipid, and protein by the mass spectroscopic device is applicable only when the target substance is known. Meanwhile, in proteomics, unidentified and numerous target substances must be measured. Therefore, in recent years, quantitative proteome using the mass spectroscopic device has become possible by labeling the entirety of the proteins contained in the samples to be compared. Currently reported methods (for example, see Non-patent Reference 11) can be divided roughly into the following three classes (see FIG. 1):

In Vivo Labeling Method

As a quantitative proteome that combines a stable isotope and a mass spectroscopic device, a method by Oda et al. exists, in which yeast proteins are labeled with $^{15}N$ (for example, see Patent Reference 1 and Non-patent References 12 to 13). Two types of cells to be compared are cultured respectively in a culture medium containing an isotope labeled amino acid and a culture medium not containing an isotope labeled amino acid, the cultured cells are mixed, then proteins are extracted, fractionated, and analyzed with the mass spectroscopic device, and the peak intensities of isotope labeled proteins and isotopically unlabeled proteins are compared. With this method, even if there is an error in the recovery rate during the analysis, the intercellular difference can be obtained quantitatively, and in addition, identification of the proteins can be carried out simultaneously with the spectrum data.

However, while this in vivo labeling method is in principle applicable to every cell as long as they are cultured cells, in reality, such as large change in cell growth rate due to the change in culture conditions, culture in a culture medium containing a stable isotope is often difficult. In other words, it can be performed only with limited cells, which are not influenced by the culture condition. In addition, tissue from animal and human or the like, cannot be cultured easily, and cannot be measured with this method.

Method for In Vitro Labeling Before Digestion

Thus, the following method has been found, as a method for comprehensively quantitating proteins in a tissue. That is to say, protein quantitation became possible by adding an isotope labeled reagent reactive to cysteine residues and an non-isotope labeled reagent reactive to cysteine residues respectively to two types of samples to be compared and labeling cysteine residues on proteins contained in the samples, purifying the proteins with a column, analyzing with a mass spectroscopic device, and comparing a pair of peak intensities (for example, see Non-patent References 14 to 19). However, proteins that do not contain a cysteine residue cannot be quantified with this method, in addition, the variation of quantitative value at each experiment in the pretreatment stage such as purification cannot be corrected.

Method for In Vitro Labeling after Digestion and During Digestion

Some methods for proteins not containing a cysteine residue and some methods with improved purification operability have been reported. Protein quantitation became possible by digesting via an enzymatic reaction a protein contained in two types of samples to be compared, labeling the obtained C-terminus and N-terminus of a peptide fragment, glutamic acid residue, aspartic acid residue and the like respectively with an isotope labeled molecule and a non-isotope labeled molecule, analyzing with a mass spectroscopic device, and comparing a pair of peak intensities (for example, see Non-patent Reference 20 to 23).

However, with these methods, the variation of quantitative value at each experiment in the pretreatment stage, such as digestion, fractionation and purification of the protein contained in the sample, cannot be corrected.

As described above, current quantitative proteome analysis method can be divided roughly into in vivo labeling method and in vitro labeling method. In the former, labeling is simple, and highly reproducible data can be expected; however, when the sample is a tissue, a biological fluid, a cell organ, a protein complex, a cell incapable of growing in a culture medium containing a stable isotope, or the like, it cannot be applied to proteins that do not incorporate stable isotope contained therein. The latter can be applied to every sample; however, the variation of quantitative value at each experiment in the pretreatment stage until labeling, such as sample disruption, extraction, digestion, fractionation and purification, cannot be corrected. In addition, the labeling reaction per se is often not simple such that differences in the experience of the experimenters show.

Quantitative proteome analysis methods thus far has been directly comparing an internal standard substance and a test sample, such that sample preparation needed to be carried out for each measurement. Further, carrying out comparison of three or more samples was not simple, which also decreased accuracy. Furthermore, when the measurement subject changed the internal standard substance to be labeled also changed, each time requiring the labeling conditions to be examined; in addition, comparison between experiments was not possible.

Moreover, quantitative proteome analysis method thus far has been directly comparing an internal standard substance and a test sample, and when the measurement subject changed, the internal standard substance to be labeled also needed to be changed. On the other hand, quantitating the internal standard substance biological molecule was not simple; therefore, absolute quantitation was very difficult.

Among the quantitative proteome analysis methods reported thus far, the AQUA method exists as an absolute quantitation method (for example, see Patent Reference 2). This is a method in which a stable isotope is incorporated into a portion of a synthetic peptide, and determines the ratio with respect to the target protein. However, with this method, an isotope labeled synthetic peptide must always be prepared for each experiment, quantification must also be carried out at each experiment, such that comprehensive quantitation is difficult. In addition, it is influenced by the recovery rate in the purification process of the objective protein, and also influenced by the efficiency of in-gel digestion generally told to be 30-50%, such that accurate quantitation is difficult.

On the other hand, as we stepped into the post genomic era, it has become more and more important to separate, identify and further quantitate proteins, which are important biological molecules in a living organism. In particular, for research and development of techniques for diagnosis and treatment of diseases, the function of multiple proteins must be elucidated.

Conventionally, two-dimensional electrophoresis has been used for the proteome analysis of proteins expressed by a cell. Here, the term "proteome analysis" means analysis for elucidating the relationship between genetic information and various proteins interacting intricately inside the cell (for example, see Non-patent Reference 24). In other words, proteome analysis designates a method for comprehensively analyzing all the proteins constituting a cell.

In the above two-dimensional electrophoresis, the expressed proteins are developed on a gel, and the spot corresponding to the subject protein is cut out to identify the type thereof comprehensively. Therefore, two-dimensional electrophoresis is a qualitative analysis means that is useful in proteome analysis.

However, it has been pointed out that two-dimensional electrophoresis was not suitable for a quantitative analysis of protein owing to the quantity of protein developed being very small and the recovery rate at analytical time being prone to errors.

Meanwhile, mass spectroscopy is used as another important protein analysis technique. The present method is a method for analyzing an accurate mass of a protein or a peptide using a mass spectroscopic device. This mass spectroscopic device generally comprises a device for ionizing proteins and peptides, and a mass separation unit for separation according to their masses, and is constituted by a mass spectrometer for analyzing the mass. Then, the ease with which a protein is identified today can be said to have kept forward with a mass spectrometer, a protein database, and a search system linking these. Therefore, a specific protein group (for example, a group of proteins that form a given complex) can be comprehensively identified.

However, merely identifying a protein, or elucidating components by mass spectroscopy is insufficient as functional analysis of protein. The reason being, in a functional analysis by proteome, comparison with a pathology, and analysis of the variation of an individual protein due to the influenced of a stimulation by a drug or a ligand, knock out or overexpression of a target gene, and the like, that is to say, quantitative data allowing the amount of protein expressed to be compared, become necessary.

Based on such a background, quantitative analyses using a mass spectroscopic device exploiting isotope labeling have been attempted (for example, see Non-patent Reference 25).

[Non-patent Reference 1] "Nature Genetics" Volume 20, September 1998, p. 46-50

[Non-patent Reference 2] "Journal of Cell Biology" Volume 141, No. 4, 18 May 1998, p. 967-977

[Non-patent Reference 3] "Current Opinion in Cell Biology" Volume 15, No. 2, April 2003, p. 199-205

[Non-patent Reference 4] "Current Opinion in Chemical Biology" Volume 7, No. 1, February 2003, p. 21-27

[Non-patent Reference 5] "Surgery Today" Volume 23, No. 3, 1993, p. 228-233

[Non-patent Reference 6] "Rapid Communications in Mass Spectrometry" Volume 8, No. 5, 1994, p. 377-380
[Non-patent Reference 7] "Journal of Chromatography A" Volume 694, No. 1, May 1995, p. 209-218
[Non-patent Reference 8] "Analytical Biochemistry" Volume 231, No. 1, October 1995, p. 141-150
[Non-patent Reference 9] "Journal of Chromatography B" Volume 729, Nos. 1-2, June 1999, p. 147-155
[Non-patent Reference 10] "Proceedings of the National Academy of Sciences of the United States of America" Volume 100, No. 12, June 2003, p. 6940-6945
[Non-patent Reference 11] "Current Opinion in Chemical Biology" Volume 7, No. 1, February 2003, p. 70-77
[Non-patent Reference 12] "Proceedings of the National Academy of Sciences of the United States of America" Volume 96, No. 12, June 1999, p. 6591-6596
[Non-patent Reference 13] "Methods" Volume 29, No. 2, February 2003, p. 124-130
[Non-patent Reference 14] "Nature Biotechnology" Volume 17, No. 10, October 1999, p. 994-999
[Non-patent Reference 15] "Analytical Chemistry" Volume 70, No. 24, December 1998, p. 5150-5158
[Non-patent Reference 16] "Rapid Communications in Mass Spectrometry" Volume 16, No. 15, 2002, p. 1416-1424
[Non-patent Reference 17] "Journal of American Society of Mass Spectrometry" Volume 12, No. 12, December 2001, p. 1238-1246
[Non-patent Reference 18] "Nature Biotechnology" Volume 19, No. 10, October 2001, p. 946-951
[Non-patent Reference 19] "Molecular and Cellular Proteomics" Volume 1, No. 1, January 2002, p. 19-29
[Non-patent Reference 20] "Analytical Chemistry" Volume 73, No. 13, July 2001, p. 2836-2842
[Non-patent Reference 21] "Rapid Communications in Mass Spectrometry" Volume 15, No. 14, 2001, p. 1214-1221
[Non-patent Reference 22] "Nature Biotechnology" Volume 20, No. 2, February 2002, p. 163-170
[Non-patent Reference 23] "Nature Biotechnology" Volume 20, No. 5, May 2002, p. 512-515
[Non-patent Reference 24] Karn, P. Science 270, pp. 369-370, 1995
[Non-patent Reference 25] "Proteome Analysis Method", Yodosha, printed 10 Jul. 2000, pp. 111-122
[Patent Reference 1] U.S. Pat. No. 6,391,649
[Patent Reference 2] WO2003 016861

DISCLOSURE OF INVENTION

Problems to be Solved by the Invention

The present invention was devised in view of such a situation, and the problem to be solved is to quantitate with good accuracy furthermore, absolutely quantitate, one or a plurality of biological molecules in a sample that cannot be labeled metabolically (for instance, tissue, biological fluid, cell, cell organ, protein complex and the like).

In addition, in an analysis using isotope labeling, sometimes mass spectra from a plurality of different biological molecules are contributing to one mass spectrum peak, making quantitative analysis of biological molecule difficult. Thus, an object of the present invention is to provide an analysis system and an analysis method that enable a quantitative analysis of a mass spectrum, even when mass spectra from a plurality of different biological molecules are contributing to a mass spectrum. In addition, the present invention provides an analysis system and an analysis method for adding quantitative analysis and functional information related to such biological molecule.

Furthermore, it is also an object of the present invention to provide a program that causes a computer to execute the previous quantitative analysis method.

Means for Solving the Problems

As a result of earnest studies to solve the above problems, the present inventors have discovered that, in mass spectroscopy of a biological molecule, by preparing an isotope labeled biological molecule beforehand, adding it to each sample and carrying out measurements with a mass spectroscopic device, one or a plurality of biological molecules in a sample that cannot be labeled metabolically (for instance, tissue, biological fluid, cell, cell organ, protein complex and the like) could be quantified with good accuracy. Further, the present inventors have discovered that, by having quantitated the isotope labeled biological molecule prepared beforehand, a comprehensive absolute quantitation of a biological molecule was also possible, and reached at the present invention. Furthermore, the present inventors have discovered that, in mass spectroscopy of a biological molecule, performing the isotope labeling method at the same time as waveform separation processing on a mass spectrum, quantitative analysis of biological molecule expression with higher accuracy was possible, and reached at the present invention.

That is to say, in a first aspect of the present invention, there is provided:

[1] a method for quantitating a biological molecule in a sample with a mass spectrometer, comprising adding to the sample an internal standard substance that is a metabolically isotope labeled biological molecule, or a cell containing an internal standard substance that is a metabolically isotope labeled biological molecule,

[2] a method for quantitating one or a plurality of biological molecules in a sample, comprising the steps of:
adding to the sample an internal standard substance that is a metabolically isotope labeled biological molecule, or a cell containing an internal standard substance that is a metabolically isotope labeled biological molecule, which are obtained by adding a precursor of a biological molecule that is isotope labeled so as to culture;
extracting and fractionating a biological molecule from the each sample;
analyzing the each fractionated biological molecule with a mass spectroscopic device;
identifying the biological molecule from mass analysis information; and
determining a ratio of intensities between a labeled peak and an unlabeled peak of each biological molecule to quantitate the biological molecule,

[3] the method according to item [1] or [2], wherein the ratio of peak intensity is compared between each sample to quantitate the biological molecule relatively,

[4] the method according to any one of items [1] to [3], wherein the biological molecule in the internal standard substance that is the metabolically isotope labeled biological molecule, or in the cell containing the internal standard substance that is the metabolically isotope labeled biological molecule, is present in a known quantity,

[5] the method according to any one of items [1] to [4], wherein the quantitation is an absolute quantitation,

[6] a method for quantitating one or a plurality of biological molecules in a sample, comprising the steps of:

(1) adding to a sample an internal standard substance that is a metabolically isotope labeled biological molecule, or a cell containing an internal standard substance that is a metabolically isotope labeled biological molecule;

(2) performing mass analysis of each biological molecule present in the sample;

(3) identifying the biological molecule from mass analysis information; and (4) determining a ratio of intensities between a labeled peak and an unlabeled peak of each biological molecule to quantitate the biological molecule,

[7] the method according to item [6], further comprising extracting and fractionating a biological molecule from the sample,

[8] the method according to item [6] or [7], further comprising performing isotope labeling of the biological molecule metabolically by adding a precursor of the biological molecule that is isotope labeled so as to culture,

[9] the method according to any one of items [6] to [8], wherein the method is performed for a plurality of samples, and further comprising comparing a ratio of peak intensity of each biological molecule between each sample,

[10] the method according to any one of items [6] to [9], which is a method for quantitating one or a plurality of biological molecules in the sample absolutely, wherein the biological molecule in the internal standard substance that is the metabolically isotope labeled biological molecule, or the biological molecule in the cell containing the internal standard substance that is the metabolically isotope labeled biological molecule, is present in a known quantity,

[11] the method according to any one of items [6] to [10], further comprising quantitating absolutely a biological molecule in the internal standard substance that is the metabolically isotope labeled biological molecule, or a biological molecule in the cell containing the internal standard substance that is the metabolically isotope labeled biological molecule,

[12] the method according to item [11], wherein the step according to item [11] comprises the steps of:

(a) adding a non-isotope labeled synthetic peptide to the internal standard substance that is the metabolically isotope labeled biological molecule, or to the cell containing the internal standard substance that is the metabolically isotope labeled biological molecule;

(b) extracting and fractionating a biological molecule from the internal standard substance that is the metabolically isotope labeled biological molecule or the cell containing the internal standard substance that is the metabolically isotope labeled biological molecule;

(c) performing mass analysis of the each fractionated biological molecule;

(d) identifying the biological molecule from mass analysis information; and (e) determining a ratio of intensities between a labeled peak and an unlabeled peak of each biological molecule to quantitate absolutely the biological molecule,

[13] the method according to any one of items [1] to [12], wherein the sample is a sample that is unable to be labeled metabolically,

[14] the method according to any one of items [1] to [13], wherein the sample is a sample that is unable to be labeled by a cell culture,

[15] the method according to any one of items [1] to [14], wherein the biological molecule is a molecule selected from the group consisting of a protein, a lipid, a sugar chain, a nucleic acid, and combinations thereof,

[16] the method according to any one of items [1] to [15], wherein the biological molecule is a protein,

[17] the method according to any one of items [1] to [16], wherein the biological molecule is a protein, the method further comprises the steps of: extracting and fractionating the protein; and digesting the protein,

[18] the method according to any one of items [1] to [17], wherein the sample is a sample selected from the group consisting of a tissue, a biological fluid, a cell, a cell organ and a protein complex,

[19] the method according to any one of items [1] to [18], wherein the isotope is an isotope selected from the group consisting of $^2$H, $^{13}$C, $^{15}$N, $^{17}$O, $^{18}$O, $^{33}$P, $^{34}$S, and combinations thereof,

[20] the method according to any one of items [1] to [19], wherein the isotope is $^{13}$C,

[21] an internal standard substance that is a metabolically isotope labeled biological molecule to be used in the method according to any one of items [1] to [20],

[22] a cell containing an internal standard substance that is a metabolically isotope labeled biological molecule to be used in the method according to any one of items [1] to [20],

[23] a reagent for use in the method according to any one of items [1] to [20], comprising an internal standard substance that is a metabolically isotope labeled biological molecule,

[24] a reagent for use in the method according to any one of items [1] to [20], comprising a cell containing an internal standard substance that is a metabolically isotope labeled biological molecule,

[25] a use of an internal standard substance that is a metabolically isotope labeled biological molecule for the method according to any one of items [1] to [20],

[26] a use of a cell containing an internal standard substance that is a metabolically isotope labeled biological molecule for the method according to any one of items [1] to [20],

[27] a program for causing a computer receiving data on mass analysis of one or a plurality of biological molecules in a sample obtained in a mass spectroscopic device to quantitate one or a plurality of biological molecules in the sample, the program comprising performing the steps of:

(1) receiving an analytical result obtained by analyzing with the mass spectroscopic device each biological molecule in the each sample, wherein an internal standard substance that is a metabolically isotope labeled biological molecule or a cell containing an internal standard substance that is a metabolically isotope labeled biological molecule is added to the sample;

(2) identifying the biological molecule from the analytical result of mass analysis; and (3) determining a ratio of intensities between a labeled peak and an unlabeled peak of each biological molecule to quantitate the biological molecule,

[28] a program for causing a computer receiving data on the mass analysis of one or a plurality of biological molecules in a sample obtained in a mass spectroscopic device to quantitate the one or a plurality of biological molecules in the sample, the program comprising performing the steps of:

(1) receiving an analytical result obtained by analyzing with the mass spectroscopic device each biological molecule in each sample, wherein an internal standard substance that is a metabolically isotope labeled biological molecule, or a cell containing an internal standard substance that is a metabolically isotope labeled biological molecule is added to the sample, and a biological molecule is extracted and fractionated from the each sample;

(2) identifying the biological molecule from the analytical result of mass analysis; and (3) determining a ratio of intensities between a labeled peak and an unlabeled peak of each biological molecule to quantitate said biological molecule,

[29] the program according to item [27] or [28], wherein analysis for a plurality of samples is performed, and further comprising performing of comparing a peak intensity ratio of each biological molecule between each sample,

[30] the program according to any one of items [27] to [29], which is a program for quantitating absolutely one or a plurality of biological molecules in the sample, and wherein the biological molecule in the internal standard substance that is the metabolically isotope labeled biological molecule, or in the cell containing the internal standard substance that is the metabolically isotope labeled biological molecule, is present in a known quantity, or the like.

In addition, in a second aspect of the present invention, there is provided:

[31] an analysis system for analyzing data on mass analysis of a first biological molecule and a second biological molecule that has been isotope labeled for corresponding to the first biological molecule, comprising:

a mass spectroscopic device for performing mass analysis of the first and the second biological molecules; and a control unit comprising a data input and output unit for receiving the data on the mass analysis of the biological molecule from the mass spectroscopic device, wherein the control unit comprises:

a processing unit for determining a first m/z value of the first biological molecule for which a sequence of a biological molecular component has been determined, and a second m/z value of the second biological molecule for which a sequence of a biological molecular component has been determined, and, extracting data containing a mass spectrum against m/z values of the first and the second biological molecules and a mass spectrum against a time (a mass chromatogram) at m/z values of the first biological molecule and the second biological molecule from data on mass analysis obtained in the mass spectroscopic device, based on the first and the second m/z values; and a waveform processing unit for receiving the mass spectrum against the time (the mass chromatogram) at the first and the second m/z values from the processing unit, and performing waveform separation processing of the mass spectrum against the time (the mass chromatogram). According to such constitution, a mass spectrum derived from an individual biological molecule can be obtained, and a more quantitative analysis is possible.

In a preferred aspect of the present invention, in the analysis system according to item [31], [32] the determination of the first and the second m/z values is carried out in such a way that the determination of the second m/z value is made by determining from the first m/z value of the first biological molecule for which the sequence of the biological molecular component has been determined, based on information on the number of non-isotope labeled component of the first biological molecule and an electric charge of the first biological molecule, or the determination of the first m/z value is made by determining from the second m/z value of the second biological molecule for which the sequence of the biological molecular component has been determined, based on information on the number of isotope labeled components of the second biological molecule and an electric charge of the second biological molecule. According to such constitution, the variation of the expression of biological molecules containing non-isotope labeled and isotope labeled components can be followed by monitoring one of the biological molecules.

In a preferred aspect of the present invention, in the analysis system according to item [31] or [32], [33] the control unit further comprises a computation unit for calculating an area of a waveform derived from an individual biological molecule obtained by waveform separation processing from the waveform separation processing unit, and calculating a ratio (an area of a first waveform)/(an area of a second waveform) from a value of the area of the first waveform derived from an individual biological molecule at the first m/z value and a value of the area of the second waveform derived from an individual biological molecule at the second m/z value. According to such constitution, quantitative analysis of the expression of other protein becomes possible by contrast with one of the proteins.

In a preferred aspect of the present invention, in the analysis system according to any one of items [31] to [33], [34] the control unit further comprises an information addition unit for performing, after waveform separation, classification for each sequence of a component of the biological molecule, retrieving the sequence with a database containing information on the function of biological molecules, and linking the sequence to function from the result of the verification so as to group. According to such constitution, linking of the sequence of the waveform separated biological molecular component with functional information becomes possible.

In a preferred aspect of the present invention, in the analysis system according to any one of items [31] to [34], [35] the control unit further comprises a computation unit for identifying the biological molecule from the sequence of the biological molecular component, and determining, from a quantitative value of each biological molecular component constituting the biological molecule, a mean value to serve as a representative quantitative value for the biological molecule. According to such constitution, the representative quantitative value of the component of the biological molecule can be determined and can be linked with functional information by the verification with a database described below.

In a preferred aspect of the present invention, in the analysis system according to any one of items [31] to [35], [36] the control unit further comprises an information addition unit for retrieving the sequence of the biological molecular component with the database containing information on the function of biological molecules, and acquiring information on function of the biological molecule. According to such constitution, knowledge on the relationship between the representative quantitative value of the component and functional information can be obtained.

In a preferred aspect of the present invention, in the analysis system according to any one of items [31] to [36], [37]

when mass analyses of the first and the second biological molecules are performed in the presence of an internal standard substance, the waveform processing unit for receiving a mass spectrum against a time (a mass chromatogram) at the m/z value of the internal standard substance and further performing waveform separation processing to obtain a waveform specific to the internal standard substance, and the computation unit for calculating an area of the waveform specific to the internal standard substance from the waveform processing unit and at the same time further calculating a ratio (the area of the first waveform)/(the area of the waveform specific to the internal standard substance), and/or a ratio (the area of the second waveform)/(the area of the waveform specific to the internal standard substance). According to such constitution, absolute quantitation becomes possible when the biological molecule in the internal standard substance is in a known quantity.

In addition, in a third aspect of the present invention, there is provided:

[38] an analysis system for analyzing data on mass analysis of an internal standard substance, which is an isotope labeled biological molecule for corresponding to a first and a second biological molecule, comprising:

a mass spectroscopic device for performing mass analysis of the first and the second biological molecules as well as the isotope labeled biological molecule; and a control unit comprising a data input and output unit for receiving the data on mass analysis of the biological molecules from the mass spectroscopic device;

wherein the control unit comprises:

a processing unit for determining a first m/z value and a second m/z value of the biological molecule for which a sequence of a biological molecular component has been determined and a m/z value of an internal standard substance which is isotope labeled biological molecule for which a sequence of a biological molecular component has been determined, and, extracting data containing mass spectrum against the m/z value and a mass spectrum against a time (a mass chromatogram) of the first and the second biological molecules as well as of the biological molecule constituting the internal standard substance from the data on mass analysis obtained in the mass spectroscopic device, based on the m/z values of the first and the second as well as the internal standard substance; and a waveform processing unit for receiving the mass spectrum against the time (the mass chromatogram) at the m/z values of the first and the second biological molecules as well as the internal standard substance from the processing unit and performing waveform separation processing of the mass spectrum against the time (the mass chromatogram). According to such constitution, even if the biological molecule is non-isotope labeled, in a comparison with an isotope labeled internal standard substance, the mass spectrum derived from the biological molecule specific to this biological molecule can be obtained, and a more quantitative analysis is possible.

In a preferred aspect of the present invention, in the analysis system according to item [38], [39] the determination of the first m/z value and the second m/z value, as well as the m/z value of the internal standard substance is carried out in such a way that the determination of the m/z value of the biological molecule constituting the internal standard substance is made by determining, from the first m/z value and the second m/z value of the first and the second biological molecules for which a sequence of the biological molecular component has been determined, based on information on the number of non-isotope labeled components of the first and the second biological molecules and an electric charge of the first and the second biological molecules, or the determination of the first m/z value and the second m/z value of the first and the second biological molecules is made by determining, from the m/z value of the internal standard substance for which a sequence of the biological molecular component has been determined, based on information on the number of isotope labeled biological molecular components of the internal standard substance and an electric charge of the biological molecule constituting the internal standard substance.

In a preferred aspect of the present invention, in the analysis system according to item [38] or [39], [40] the control unit further comprises a computation unit for calculating an area of a waveform derived from an individual biological molecule obtained by waveform separation processing from the waveform separation processing unit, and calculating a ratio (an area of a first waveform)/(an area of a waveform specific to the internal standard substance), and/or, a ratio (an area of a second waveform)/(an area of a waveform specific to the internal standard substance) from values of the areas of the first waveform and the second waveform derived from specific biological molecules at the first and the second m/z values, and a value of the area of the internal standard substance waveform derived from an individual biological molecule at the m/z value of the internal standard substance.

In a preferred aspect of the present invention, in the analysis system according to any one of items [38] to [40], [41] the control unit further comprises an information addition unit for performing, after waveform separation, classification for each sequence of the biological molecular component, retrieving the sequence with a database containing information on the function of biological molecules, and linking the sequence with function from the result of the verification so as to group.

In a preferred aspect of the present invention, in the analysis system according to any one of items [38] to [41], [42] the control unit further comprises a computation unit for identifying the biological molecule from the sequence of the biological molecular component, and determining, from a quantitative value of each biological molecular component constituting the biological molecule, a mean value to serve as a representative quantitative value for the biological molecule.

In a preferred aspect of the present invention, in the analysis system according to any one of items [38] to [42], [43] the control unit further comprises an information addition unit for retrieving the sequence of the biological molecular component with the database containing information on the function of biological molecules, and acquiring information on function of the biological molecule.

In a preferred aspect of the present invention, in the analysis system according to any one of items [31] to [43], [44] the isotope used in the isotope labeling is any isotope selected from the group consisting of $^2H$, $^{13}C$, $^{15}N$, $^{17}O$, $^{18}O$, $^{33}P$ and $^{34}S$, as well as combinations thereof.

In a preferred aspect of the present invention, in the analysis system according to any one of items [31] to [44], [45] the determination of the sequence of the component is carried out by MS/MS processing.

In a preferred aspect of the present invention, in the analysis system according to [45], [46] the determination of the sequence of the component is carried out by retrieving data obtained by MS/MS processing with a database regarding the biological molecule.

In a preferred aspect of the present invention, in the analysis system according to any one of items [31] to [46], [47] the biological molecule is a biological molecule that has been separated from the sample over time.

In a preferred aspect of the present invention, in the analysis system according to any one of items [31] to [47], [48] the biological molecule is any molecule selected from the group consisting of a protein, a lipid, a sugar chain and a nucleic acid as well as combinations thereof.

In addition, in a fourth aspect of the present invention, there is provided:

[49] an analysis method for analyzing data on mass analysis of a first biological molecule and a second biological molecule that has been isotope labeled for corresponding to the first biological molecule, comprising the steps of:

determining, among the data on the mass analysis of the biological molecule measured in a mass spectroscopic device, a first m/z value of the first biological molecule for which a sequence of a biological molecular component has been determined, and a second m/z value of the second biological molecule for which a sequence of a biological molecular component has been determined, extracting data containing a mass spectrum against m/z values and a mass spectrum against a time (a mass chromatogram) of the first biological molecule and the second biological molecule from the data on the mass analysis, based on the first and the second m/z values; and performing waveform separation processing of the mass spectrum against the time (the mass chromatogram) of the first and the second biological molecules,

[50] the analysis method according to item [49], wherein the determination of the first m/z value and the second m/z value is carried out in such a way that the determination of the second m/z value is made by determining from the first m/z value of the first biological molecule for which the sequence of the biological molecular component has been determined, based on information on the number of non-isotope labeled components of the first biological molecule and an electric charge of the first biological molecule, or the determination of the first m/z value of the second biological molecule is made by determining from the second m/z value of the second biological molecule for which the sequence of the biological molecular component has been determined, based on information on the number of isotope labeled components of the second biological molecule and an electric charge of the second biological molecule,

[51] the analysis method according to item [49] or [50], further comprising the steps of:

calculating an area of a waveform derived from an individual biological molecule obtained by the waveform separation processing step; and calculating a ratio (an area of a first waveform)/(an area of a second waveform) from a value of the area of the first waveform derived from an individual biological molecule at the first m/z value, and a value of the area of the second waveform derived from an individual biological molecule at the second m/z value,

[52] the analysis method according to any one of items [49] to [51], further comprising the steps of:

performing, after the waveform separation, classification for each sequence of a component of the biological molecule, retrieving the sequence with a database containing information on the function of biological molecules, and linking the sequence to function from the result of the verification so as to group,

[53] the analysis method according to any one of items [49] to [52], further comprising the steps of:

identifying the biological molecule from the sequence of the biological molecular component; and determining, from a quantitative value of each biological molecular component constituting the biological molecule, a mean value to serve as a representative quantitative value for the biological molecule,

[54] the analysis method according to items [49] to [53], further comprising retrieving the sequence of the biological molecular component with a database containing information on the function of biological molecules so as to acquire information on the function of the biological molecule,

[55] the analysis method according to item [49] to [54], further comprising the steps of:

performing determination of a m/z value of the internal standard substance along with m/z values of the first and the second biological molecules, extraction of data containing a mass spectrum against a time (a mass chromatogram) of the internal standard substance, waveform separation processing of the mass spectrum against the time (the mass chromatogram) of the internal standard substance and calculation of an area of a waveform specific to the internal standard substance; and calculating a ratio (the area of the first waveform)/(the area of the waveform specific to the internal standard substance), and/or, a ratio (the area of the second waveform)/(the area of the waveform specific to the internal standard substance),

[56] an analysis method for analyzing data on mass analysis of an internal standard substance, which is a biological molecule that has been isotope labeled for corresponding to a first and a second biological molecule, comprising the steps of:

determining, among the data on the mass analysis of the biological molecules measured in a mass spectroscopic device, a first m/z value and a second m/z value of the first and the second biological molecules for which a sequence of a biological molecular component has been determined, and a m/z value of the biological molecule constituting the internal standard substance for which a sequence of a biological molecular component has been determined;

extracting data containing a mass spectrum against m/z values and a mass spectrum against a time (a mass chromatogram) of the first and the second biological molecules as well as of the biological molecule constituting the internal standard substance from the data on the mass analysis, based on the m/z values of the first and the second as well as of the internal standard substance; and performing waveform separation processing of the mass spectrum against the time (the mass chromatogram) of the first and second of the biological molecules, as well as the biological molecule constituting the internal standard substance,

[57] the analysis method according to item [56], wherein the determination of the first m/z value and the second m/z value, as well as the m/z value of the internal standard substance is carried out in such was that the determination of the m/z value of the biological molecule constituting the internal standard substance is made by determining, from the first m/z value and the second m/z value of the first and the second biological molecules for which a sequence of the biological molecular component has been determined, based on information on the number of non-isotope labeled components of the first and the second biological molecules and an electric charge of the first and the second biological molecules, or the determination of the first m/z value and the second m/z value is made by determining, from the m/z value of the internal standard substance for which a sequence of the biological molecular component has been determined, based on information on the number of isotope labeled biological molecular components of the internal standard substance and an electric charge of the biological molecule constituting the internal standard substance,

[58] the analysis method according to item [56] or [57], further comprising the steps of:

calculating an area of a waveform derived from an individual biological molecule obtained by the waveform separation processing step; and performing calculation a ratio (an area of a first waveform)/(an area of a waveform specific to the internal standard substance), and/or, a ratio (an area of a second waveform)/(an area of a waveform specific to the internal standard substance) from values of the areas of the first and the second waveforms derived from specific biological molecules at the first and the second m/z values, and a value of the area of the internal standard substance waveform derived from an individual biological molecule at m/z value of the internal standard substance,

[59] the analysis method according to any one of items [56] to [58], further comprising the steps of:

performing, after the waveform separation, classification for each sequence of the component of the biological molecule;

retrieving the sequence with a database containing information on the function of biological molecules; and linking the sequence to function from the result of the verification so as to group,

[60] the analysis method according to any one of items [56] to [59], further comprising the steps of:

identifying the biological molecule from the sequence of the biological molecular component; and determining, from a quantitative value of each biological molecular component constituting the biological molecule, a mean value to serve as a representative quantitative value for the biological molecule,

[61] the analysis method according to any one of items [56] to [60], further comprising retrieving the sequence of the biological molecular component with a database containing information on the function of biological molecules so as to acquire information on the function of the biological molecule,

[62] the analysis method according to any one of items [49] to [61], wherein the isotope used in the isotope labeling is any isotope selected from the group consisting of $^2H$, $^{13}C$, $^{15}N$, $^{17}O$, $^{18}O$, $^{33}P$ and $^{34}S$, as well as combinations thereof,

[63] the analysis method according to any one of items [49] to [62], wherein the determination of the sequence of the component is carried out by MS/MS processing,

[64] the analysis method according to item [63], wherein the determination of the sequence of the component is carried out by retrieving data obtained by MS/MS processing with a database regarding a biological molecule,

[65] the analysis method according to any one of items [49] to [64], wherein the biological molecule is a biological molecule that has been separated from the sample over time,

[66] the analysis method according to any one of items [49] to [65], wherein the biological molecule is any molecule selected from the group consisting of a protein, a lipid, a sugar chain and a nucleic acid, as well as combinations thereof.

In addition, in a fifth aspect of the present invention, there is provided:

[67] a program for causing a computer receiving data obtained in a mass spectroscopic device to analyze the data in which the data is related to mass analysis of a first biological molecule and a second biological molecule, which has been isotope labeled for corresponding to the first biological molecule, the program performing the steps of:

determining, among the data on the mass analysis of the biological molecule measured in the mass spectroscopic device, a first m/z value of the first biological molecule for which a sequence of a biological molecular component has been determined, and a second m/z value of the second biological molecule for which a sequence of a biological molecular component has been determined, extracting data containing a mass spectrum against m/z values and a mass spectrum against a time (a mass chromatogram) of the first biological molecule and the second biological molecule from the data on the mass analysis, based on the first and the second m/z values; and performing waveform separation processing of the mass spectrum against the time (the mass chromatogram) of the first and the second biological molecules,

[68] the program according to item [67], wherein the determination of the first m/z value and the second m/z value is carried out in such a way that the determination of the second m/z value is made by determining from the first m/z value of the first biological molecule for which the sequence of the biological molecular component has been determined, based on information on the number of non-isotope labeled components of the first biological molecule and an electric charge of the first biological molecule, or the determination of the first m/z value of the second biological molecule is made by determining from the second m/z value of the second biological molecule for which the sequence of the biological molecular component has been determined, based on information on the number of isotope labeled components of the second biological molecule and an electric charge of the second biological molecule,

[69] the program according to item [67] or [68], further comprising performing the steps of:

calculating an area of a waveform derived from an individual biological molecule obtained by the waveform separation processing step; and calculating a ratio (an area of a first waveform)/(an area of a second waveform) from a value of the area of the first waveform derived from an individual biological molecule at the first m/z value, and a value of the area of the second waveform derived from an individual biological molecule at the second m/z value,

[70] the program according to any one of items [67] to [69], further comprising performing the steps of:

performing, after the waveform separation, classification for each sequence of a component of the biological molecule, retrieving the sequence with a database containing information on the function of biological molecules, and linking the sequence to function from the result of the verification so as to group,

[71] the program according to any one of items [67] to [70], further comprising performing the steps of:

identifying the biological molecule from the sequence of the biological molecular component; and determining, from a quantitative value of each biological molecular component constituting the biological molecule, a mean value to serve as a representative quantitative value for the biological molecule,

[72] the program according to any one of items [67] to [71], further comprising performing of retrieving the sequence of the biological molecular component with a database containing information on the function of biological molecules so as to acquire information on the function of the biological molecule,

[73] the program according to any one of items [67] to [72], further comprising performing the steps of:

obtaining, in the mass spectroscopic device, data on the mass analysis of an internal standard substance along with the mass analysis of the first and the second biological molecules, extracting a mass spectrum against a time (a mass chromatogram) of the internal standard substance from the data on the mass analysis, and performing waveform separation processing of the mass spectrum against the time (the mass chromatogram) of the internal standard substance, and calculating an area of a waveform specific to the internal standard substance obtained from the waveform separation processing to compute a ratio (an area of a first waveform)/(an area of a waveform specific to the internal standard substance), and/or, a ratio (an area of a second waveform)/(an area of a waveform specific to the internal standard substance),

[74] a program for causing a computer receiving data obtained in a mass spectroscopic device to analyze the data in which the data is related to mass analysis of a first and a second biological molecule, and an internal standard substance, which is a biological molecule that has been isotope labeled for corresponding to the first and the second biological molecules, the program performing the steps of:

determining, among the data on the mass analysis of the biological molecules measured in the mass spectroscopic device, a first m/z value and a second m/z value of the first and the second biological molecules for which a sequence of a biological molecular component has been determined, and a m/z value of the biological molecule constituting the internal standard substance for which a sequence of a biological molecular component has been determined;

extracting data containing a mass spectrum against m/z values and a mass spectrum against a time (a mass chromatogram) of the first and the second biological molecules as well as of the internal standard substance biological molecule from the data on the mass analysis, based on the m/z values of the first and the second as well as of the internal standard substance; and performing waveform separation processing of the mass spectrum against the time (the mass chromatogram) of the first and second of the biological molecules, as well as the biological molecule constituting the internal standard substance,

[75] the program according to item [74], wherein the determination of the first m/z value and the second m/z value, as well as the m/z value of the internal standard substance is carried out in such was that the determination of the m/z value of the biological molecule constituting the internal standard substance is made by determining, from the first m/z value and the second m/z value of the first and the second biological molecules for which a sequence of the biological molecular component has been determined, based on information on the number of non-isotope labeled components of the first and the second biological molecules and an electric charge of the first and the second biological molecules, or the determination of the first m/z value and the second m/z value is made by determining, from the m/z value of the internal standard substance for which a sequence of the biological molecular component has been determined, based on information on the number of isotope labeled biological molecular components of the internal standard substance and an electric charge of the biological molecule constituting the internal standard substance,

[76] the program according to item [74] or [75], further comprising performing the steps of:

calculating an area of a waveform derived from an individual biological molecule obtained by the waveform separation processing step; and performing calculation a ratio (an area of a first waveform)/(an area of a waveform specific to the internal standard substance), and/or, a ratio (an area of a second waveform)/(an area of a waveform specific to the internal standard substance) from values of the areas of the first and the second waveforms derived from specific biological molecules at the first and the second m/z values, and a value of the area of the internal standard substance waveform derived from an individual biological molecule at m/z value of the internal standard substance,

[77] the program according to any one of items [74] to [76], further comprising performing the steps of:

performing, after the waveform separation, classification for each sequence of the component of the biological molecule;

retrieving the sequence with a database containing information on the function of biological molecules; and linking the sequence to function from the result of the verification so as to group,

[78] the program according to any one of items [74] to [77], further comprising performing the steps of:

identifying the biological molecule from the sequence of the biological molecular component; and determining, from a quantitative value of each biological molecular component constituting the biological molecule, a mean value to serve as a representative quantitative value for the biological molecule,

[79] the program according to any one of items [74] to [78], further comprising performing of retrieving the sequence of the biological molecular component with a database containing information on the function of biological molecules so as to acquire information on the function of the biological molecule,

[80] the program according to any one of items [67] to [79], wherein the isotope used in the isotope labeling is any isotope selected from the group consisting of $^2$H, $^{13}$C, $^{15}$N, $^{17}$O, $^{18}$O, $^{33}$P and $^{34}$S, as well as combinations thereof,

[81] the program according to any one of items [67] to [80], wherein the determination of the sequence of the component is carried out by MS/MS processing,

[82] the program according to item 81, wherein the determination of the sequence of the component is carried out by retrieving data obtained by MS/MS processing with a database regarding the biological molecule,

[83] the program according to any one of items [67] to [82], wherein the biological molecule is a biological molecule that has been separated from the sample over time.

[84] the program according to any one of items [67] to [83], wherein the biological molecule is any molecule selected from the group consisting of a protein, a lipid, a sugar chain and a nucleic acid, as well as combinations thereof.

In addition, in a sixth aspect of the present invention, there is provided:

[85] an analysis method for analyzing data on mass analysis of an internal standard substance, which is a biological molecule that has been isotope labeled for corresponding to a first and a second biological molecule, comprising the steps of:

determining, among data on the mass analysis of the biological molecule measured in a mass spectroscopic device, a first m/z value and a second m/z value of the first and the second biological molecules for which a sequence of a biological molecular component has been determined, and a m/z value of a biological molecule constituting an internal standard substance for which a sequence of a biological molecular component has been determined; and retrieving with a database containing information on the function of biological molecules based on the obtained data, so as to acquire information on the function of the biological molecule,

[86] the analysis method according to item [85], further comprising, after the determination step, extracting a mass spectrum against m/z values and a mass spectrum against a time (a mass chromatogram) of the first and the second biological molecules as well as of the biological molecule constituting the internal standard substance, from the data on the mass analysis, based on the first and the second m/z values as well as the m/z value of the internal standard substance.

[87] the analysis method according to item [85] or [86], wherein the determination of the first m/z value and the second m/z value, as well as the m/z value of the internal standard substance is carried out in such was that the determination of the m/z value of the biological molecule constituting the internal standard substance is made by determining, from the first m/z value and the second m/z value of the first and the second biological molecules for which a sequence of the biological molecular component has been determined, based on information on the number of non-isotope labeled components of the first and the second biological molecules and an electric charge of the first and the second biological molecules, or the determination of the first m/z value and the second m/z value is made by determining, from the m/z value of the internal standard substance for which a sequence of the biological molecular component has been determined, based on information on the number of isotope labeled biological molecular components of the internal standard substance and an electric charge of the biological molecule constituting the internal standard substance,

[88] the analysis method according to any one of items [85] to [87], further comprising performing calculation of a ratio (a first peak)/(a peak specific to the internal standard substance), and/or, a ratio (a second peak)/(a peak specific to the internal standard substance) from values of the first and the second peaks derived from specific biological molecules at the first and the second m/z values, and a value of an internal standard substance peak derived from an individual biological molecule at the m/z value of the internal standard substance,

[89] the analysis method according to any one of items [85] to [88], further comprising linking the sequence to function from the result of the verification so as to group,

[90] the analysis method according to any one of items [85] to [89], further comprising the steps of:

identifying the biological molecule from the sequence of the biological molecular component; and determining, from a quantitative value of each biological molecular component constituting the biological molecule, a mean value to serve as a representative quantitative value for the biological molecule,

[91] the analysis method according to any one of items [85] to [90], wherein the isotope used in the isotope labeling is any isotope selected from the group consisting of $^2$H, $^{13}$C, $^{15}$N, $^{17}$O, $^{18}$O, $^{33}$P and $^{34}$S, as well as combinations thereof,

[92] the analysis method according to any one of items [85] to [91], wherein the determination of the sequence of the component is carried out by MS/MS processing,

[93] the analysis method according to item [92], wherein the determination of the sequence of the component is carried out by retrieving data obtained by MS/MS processing with a database regarding a biological molecule,

[94] the analysis method according to any one of items [85] to [93], wherein the biological molecule is a biological molecule that has been separated from the sample over time,

[95] the analysis method according to any one of items [85] to [94], wherein the biological molecule is any molecule selected from the group consisting of a protein, a lipid, a sugar chain, and a nucleic acid, as well as combinations thereof, and

[96] a program for causing a computer receiving data obtained in a mass spectroscopic device to analyze the data in which the data is related to mass analysis of a first and a second biological molecule, and an internal standard substance, which is a biological molecule that has been isotope labeled for corresponding to the first and the second biological molecules, the program performing the steps of:

determining, among the data on the mass analysis of the biological molecule measured in the mass spectroscopic device, a first m/z value and a second m/z value of the first and the second biological molecule for which a sequence of a biological molecular component has been determined, and a m/z value of a biological molecule constituting an internal standard substance for which a sequence of a biological molecular component has been determined, retrieving with a database containing information on the function of biological molecules based on the obtained data, so as to acquire information on the function of the biological molecule,

[97] the program according to item [96], further comprising performing of, after the determination step, extracting a mass spectrum against m/z values and a mass spectrum against a time (a mass chromatogram) of the first and the second biological molecules as well as of the biological molecule constituting the internal standard substance, from the data on the mass analysis, based on the first and the second m/z values as well as the m/z value of the internal standard substance,

[98] the program according to item [96] or [97], wherein the determination of the first m/z value and the second m/z value, as well as the m/z value of the internal standard substance is carried out in such was that the determination of the m/z value of the biological molecule constituting the internal standard substance is made by determining, from the first m/z value and the second m/z value of the first and the second biological molecules for which a sequence of the biological molecular component has been determined, based on information on the number of non-isotope labeled components of the first and the second biological molecules and an electric charge of the first and the second biological molecules, or the determination of the first m/z value and the second m/z value is made by determining, from the m/z value of the internal standard substance for which a sequence of the biological molecular component has been determined, based on information on the number of isotope labeled biological molecular components of the internal standard substance and an electric charge of the biological molecule constituting the internal standard substance,

[99] the program according to any one of items 96 to 98, further comprising performing calculation of a ratio (a first peak)/(a peak specific to the internal standard substance), and/or, a ratio (a second peak)/(a peak specific to the internal standard substance) from values of the first and the second peaks derived from specific biological molecules at the first and the second m/z values, and a value of an internal standard substance peak derived from an individual biological molecule at the m/z value of the internal standard substance,

[100] the program according to any one of items 96 to 99, further comprising performing of linking the sequence to function from the result of the verification so as to group,

[101] the program according to any one of items [96] to [100], further comprising performing the steps of:
 identifying the biological molecule from the sequence of the biological molecular component; and
 determining, from a quantitative value of each biological molecular component constituting the biological molecule, a mean value to serve as a representative quantitative value for the biological molecule,

[102] the program according to any one of items [96] to [101], wherein the isotope used in the isotope labeling is any isotope selected from the group comprising $^2H$, $^{13}C$, $^{15}N$, $^{17}O$, $^{18}O$, $^{33}P$ and $^{34}S$, as well as combinations thereof,

[103] the program according to any one of items [96] to [102], wherein the determination of the sequence of the component is carried out by MS/MS processing,

[104] the program according to item 103, wherein the determination of the sequence of the component is carried out by retrieving data obtained by MS/MS processing with a database regarding a biological molecule,

[105] the program according to any one of items [96] to [104], wherein the biological molecule is a biological molecule that has been separated from the sample over time,

[106] the program according to any one of items [96] to [105], wherein the biological molecule is any molecule selected from the group consisting of a protein, a lipid, a sugar chain and a nucleic acid, as well as combinations thereof.

In addition, in a seventh aspect of the present invention, there is provided:

[107] a program for causing a computer receiving data on mass analysis obtained in a mass spectroscopic device in which the date is related to one or a plurality of biological molecules in a sample, to quantitate the one or a plurality of biological molecules in the sample, the program performing the steps of:
 determining, among the data on the mass analysis of the biological molecule measured in the mass spectroscopic device, a first m/z value of the first biological molecule for which a sequence of a biological molecular component has been determined, and a second m/z value of the second biological molecule for which a sequence of a biological molecular component has been determined,
 extracting data containing a mass spectrum against m/z values and a mass spectrum against a time (a mass chromatogram) of the first biological molecule and the second biological molecule from the data on the mass analysis, based on the first and the second m/z values; and
 performing waveform separation processing of the mass spectrum against the time (the mass chromatogram) of the first and the second biological molecules,

[108] the program according to item [107], wherein the determination of the first m/z value and the second m/z value is carried out in such a way that the determination of the second m/z value is made by determining from the first m/z value of the first biological molecule for which the sequence of the biological molecular component has been determined, based on information on the number of non-isotope labeled components of the first biological molecule and an electric charge of the first biological molecule, or the determination of the first m/z value of the second biological molecule is made by determining from the second m/z value of the second biological molecule for which the sequence of the biological molecular component has been determined, based on information on the number of isotope labeled components of the second biological molecule and an electric charge of the second biological molecule,

[109] the program according to item [107] or [108], further comprising performing the steps of:
 calculating an area of a waveform derived from an individual biological molecule obtained by the waveform separation processing step; and
 calculating a ratio (an area of a first waveform)/(an area of a second waveform) from a value of the area of the first waveform derived from an individual biological molecule at the first m/z value, and a value of the area of the second waveform derived from an individual biological molecule at the second m/z value,

[110] the program according to any one of items [107] to [109], further comprising performing the steps of:
 performing, after the waveform separation, classification for each sequence of a component of the biological molecule,
 retrieving the sequence with a database containing information on the function of biological molecules, and
 linking the sequence to function from the result of the verification so as to group,

[111] the program according to any one of items [107] to [110], further comprising performing the steps of:
 identifying the biological molecule from the sequence of the biological molecular component; and
 determining, from a quantitative value of each biological molecular component constituting the biological molecule, a mean value to serve as a representative quantitative value for the biological molecule,

[112] the program according to any one of items [107] to [111], further comprising performing of retrieving the sequence of the biological molecular component with a database containing information on the function of biological molecules so as to acquire information on the function of the biological molecule,

[113] the program according to any one of items [107] to [112], wherein the isotope used in the isotope labeling is any isotope selected from the group comprising $^2H$, $^{13}C$, $^{15}N$, $^{17}O$, $^{18}O$, $^{33}P$ and $^{34}S$, as well as combinations thereof,

[114] the program according to any one of items [107] to [113], wherein the determination of the sequence of the component is carried out by MS/MS processing,

[115] the program according to item [114], wherein the determination of the sequence of the component is carried out by retrieving data obtained by MS/MS processing with a database regarding a biological molecule,

[116] the program according to any one of items [107] to [115], wherein the biological molecule is a biological molecule that has been separated from the sample over time,

[117] the program according to any one of items [107] to [116], wherein the biological molecule is any molecule selected from the group consisting of a protein, a lipid, a sugar chain and a nucleic acid, as well as combinations thereof, and the like.

ADVANTAGEOUS EFFECTS OF THE INVENTION

According to the present invention, one or a plurality of biological molecules in a sample that cannot be labeled metabolically (for instance, tissue, biological fluid, cell, cell organ, protein complex and the like) can be quantitated with good accuracy.

That is to say, a conventional in vivo labeling method could only be performed in limited cells, such as those not influenced by a culture condition; however, in the present invention, since an internal standard substance that is a metabolically isotope labeled biological molecule or a cell containing an internal standard substance that is a metabolically isotope labeled biological molecule has been added to a sample, one or a plurality of biological molecules in the sample that cannot be labeled metabolically (for instance, tissue, biological fluid, cell, cell organ, protein complex and the like) can be quantitated, without limiting to cells that can be cultured.

In addition, with a conventional in vitro labeling method, the variation of quantitative value at each experiment in the pretreatment stage, such as sample disruption, extraction, digestion, fractionation and purification could not be corrected; however, in the present invention, since an internal standard substance that is a metabolically isotope labeled biological molecule or a cell containing an internal standard substance that is a metabolically isotope labeled biological molecule is added prior to carrying out sample disruption, extraction, digestion, fractionation, purification and the like, one or a plurality of biological molecules in a sample can be quantitated with good accuracy.

According to the present invention, comparison among three or more samples has become easy. That is to say, quantitative proteome analysis method so far has been directly comparing an internal standard substance and a test sample, such that sample preparation has to be carried out at each measurement. In addition, when the subject to be measured changes, an internal standard substance to be labeled also changes, such that each time, labeling conditions has to be examined, in addition, comparison between experiments is not possible; however, with the present invention, by conserving and adequately using an internal standard substance that is a metabolically isotope labeled biological molecule or a cell containing an internal standard substance that is a metabolically isotope labeled biological molecule, comparison of data between experiments, for instance, obtaining comparative data after a given time lapse (for instance, after one month, after one year, etc.) and analyzing against existing experimental data, becomes possible. Furthermore, by transferring or lending the internal standard substance that is the metabolically isotope labeled biological molecule or the cell containing the internal standard substance that is the metabolically isotope labeled biological molecule used, until now impossible data comparison between investigators, which was not possible so far, becomes possible.

According to the present invention, by calculating beforehand a concentration of an internal standard substance that is a metabolically isotope labeled biological molecule or a biological molecule in a cell containing an internal standard substance that is a metabolically isotope labeled biological molecule, absolute quantitation of the biological molecule is possible. By transferring or lending the internal standard substance that is the metabolically isotope labeled biological molecule or the cell containing the internal standard substance that is the metabolically isotope labeled biological molecule, data sharing between investigators becomes possible. In addition, once the absolute quantity of the internal standard substance that is the metabolically isotope labeled biological molecule or a biological molecule in the cell containing the internal standard substance that is the metabolically isotope labeled biological molecule has been determined, quantitation is not necessary for each experiment, and the value is applicable to various experiments thereafter.

Furthermore, according to the analysis device and analysis method of the present invention, a mass spectrum derived from an individual biological molecule can be obtained, and quantitatively analyzing the amount of biological molecule expressed in a cell inside an organism, which varies sometimes constantly, becomes possible. In addition, according to a program of the present invention, the previous analysis method can be implemented in a computer. Furthermore, by retrieving the quantitative analysis result with a database such as NCBInr, addition of functional information to the quantitative analysis result is also possible.

With a conventional method (AQUA method), since a synthetic peptide is added to a sample, quantitative values could not be obtained with good accuracy, due to a low protein recovery rate in the fractionation, extraction, purification and digestion (in particular in-gel digestion) steps. On the other hand, with the method of the present invention, since an internal standard substance that is a metabolically isotope labeled biological molecule or a cell containing an internal standard substance that is a metabolically isotope labeled biological molecule is added to a sample, highly reproducible quantitative value can be obtained with good accuracy, without being influenced by the protein recovery rate in the fractionation, extraction, purification and digestion (in particular in-gel digestion) steps.

In addition, in a conventional method, as a synthetic peptide is added to a sample, peptides that can be quantitated are limited to peptides having a sequence that is identical to the synthetic peptide. Therefore, influence on the quantitative value of the protein becomes large, due to errors in the results of peptide measurement. On the other hand, in the method of the present invention, a biological molecule in an internal standard substance that is a metabolically isotope labeled biological molecule or a cell containing an internal standard substance that is a metabolically isotope labeled biological molecule is quantitated, and the internal standard substance that is the metabolically isotope labeled biological molecule or the cell containing the internal standard substance that is the metabolically isotope labeled biological molecule is added to a sample; therefore, peptides that can be quantitated are not limited to peptides having a sequence that is identical to the synthetic peptide, and other peptides derived from a protein that the peptide was constituting can also be quantitated. Therefore, one protein can be quantitated via a plurality of peptides, such that a highly reproducible quantitative value can be obtained with good accuracy, without a large influence on the quantitative value of the protein due to errors in the results of individual peptide measurement.

Furthermore, a peptide synthesizer employs 10-fold excess amounts of reagents, and moreover, the synthesis scale is from microgram to milligram units. Therefore, synthesis of an isotope labeled peptide becomes extremely expensive, and a comprehensive quantitating with a conventional method is difficult from the viewpoint of costs. On the other hand, with the method of the present invention, isotope labeling of the biological molecule is carried out by a cell culture, such that production is possible with good efficiency even for small quantities. In addition, as the synthetic peptide for quantitating a biological molecule in an internal standard substance that is a metabolically isotope labeled biological molecule or a cell containing an internal standard substance that is a metabolically isotope labeled biological molecule can be handled with ordinary peptide synthesis that does not require an isotope, it is suited for a comprehensive quantitation method.

BRIEF DESCRIPTION OF DRAWINGS

FIG. 26A indicates the result of waveform separation processing of a mass chromatogram represented by L shown in FIG. 19, while FIG. 26B indicates the result of waveform separation processing of a mass chromatogram represented by H shown in FIG. 19.

FIG. 27 shows the result of comparison of peak intensity ratios derived from a wild type mouse brain (Wild) and derived from ADAM22 gene deficient mouse brain (K/O), when peaks of the same sequence derived from an internal standard substance that is a metabolically isotope labeled biological molecule were used and when the peaks from different sequences were used, when calculating the intensity ratios of peaks derived from a wild type mouse brain (Wild) and derived from ADAM22 gene deficient mouse brain (K/O) with respect to the peak derived from an internal standard substance that is a metabolically isotope labeled biological molecule.

FIG. 28 shows a sequence after waveform separation considered in one example of the present invention, and the quantitative value of this sequence.

FIG. 29 shows a listing of GiNo of proteins identified against each sequence, as a result of performing a pattern search in HomoSapiens of the NCBInr database in one example according to the present invention.

FIGS. 30A and 30B show one example of result of analyses of mass analysis data after waveform separation, using a database in the present invention.

BEST MODE FOR CARRYING OUT THE INVENTION

Figure 1:
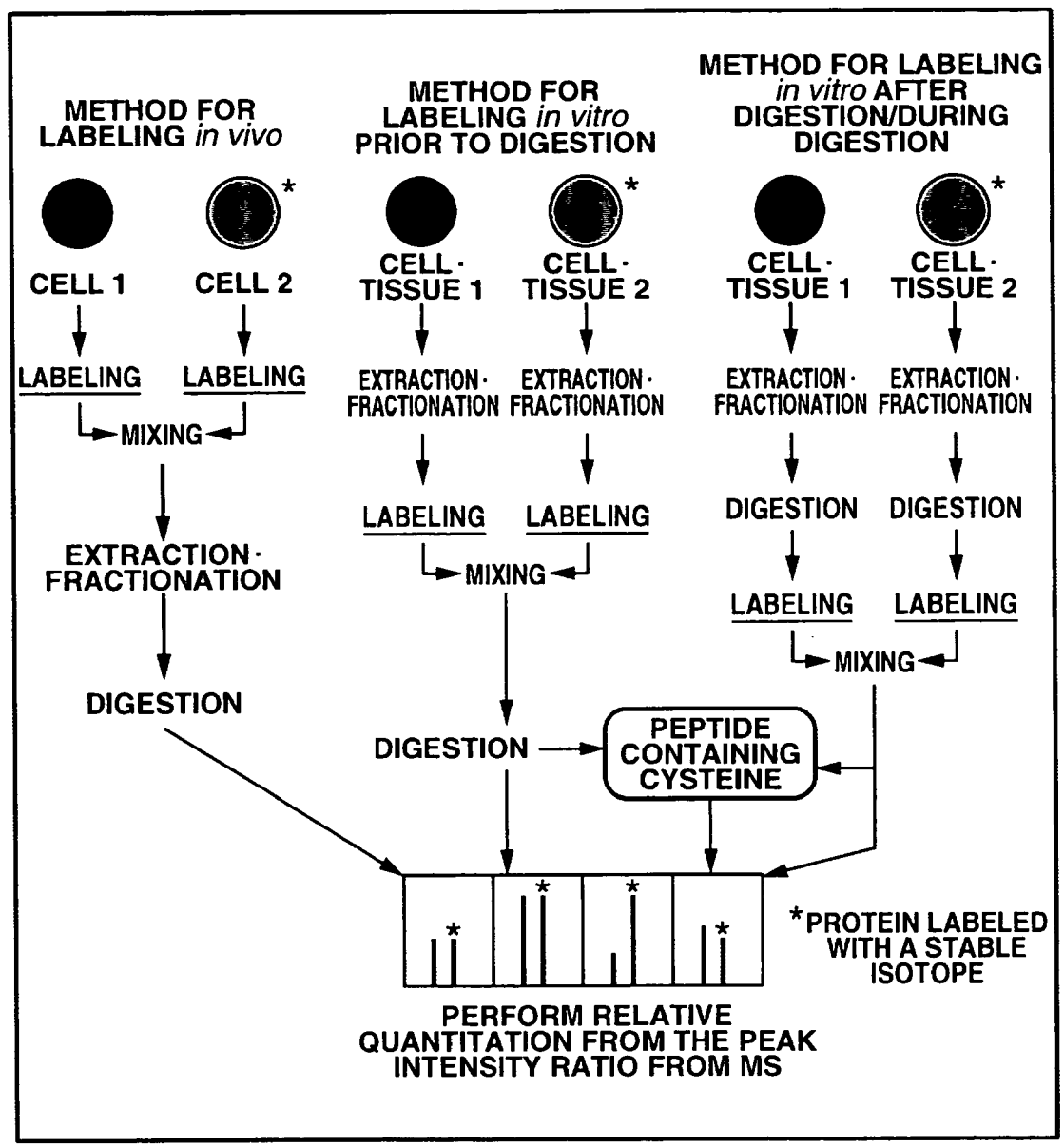
FIG. 1 shows a representation of a quantitation method in the prior art.

In the following embodiments of the present invention will be described in detail with reference to figures. The following embodiments are exemplified to describe the present invention, and the present invention is not intended to be limited to these embodiments only. The present invention can be carried out in various modes as long as they do not depart from the spirit and the scope of the present invention. Note that references, disclosure publications, patent publications and other patent references quoted in the present specification, are incorporated in the present specification by reference.

The term "sample" used in the present invention means a measurement subject containing a biological molecule, and preferably indicates a tissue, a biological fluid, a cell, a cell organ or a protein complex. Examples of the tissue include, for instance, brain, each brain site (for instance, olfactory bulb, amygdaloid nucleus, basal ganglion, hippocampus, thalamus, hypothalamus, brain cortex, medulla oblongata, cerebellum), spinal cord, pituitary gland, stomach, pancreas, kidney, liver, genital gland, thyroid gland, gallbladder, bone marrow, adrenal gland, skin, muscle, lung, duodenum, small intestine, large intestine, blood vessel, heart, thymus gland, spleen, submaxillary salivary gland, parotid gland, sublingual gland, peripheral blood, prostate gland, testicle, ovary, placentae, uterus, bone, articulation, skeletal muscle and the like. Examples of the biological fluid include, for instance, blood (including blood plasma and serum), urine, feces, saliva, lacrimal fluid, infiltration fluid (including ascites and tissue fluid) and the like. Examples of the cell include, for instance, hepatocyte, splenic cell, nerve cell, glial cell, pancreatic β cell, bone marrow cell, mesangial cell, Langerhans' cell, epidermis cell, epithelial cell, goblet cell, endothelial cell, smooth muscle cell, fibroblast, fiber cell, muscle cell, adipocyte, immunocyte (for instance, macrophage, T cell, B cell, natural killer cell, mast cell, neutrophil, eosinophil, basophil, monocyte), megakaryocyte, synoviocyte, chondrocytic, osteocytic, osteoblast, osteoclast, mammary gland cell, interstitial cell or a precursor cell thereof, stem cell, carcinoma cell and the like. Examples of the cell organ include, for instance, nucleus, organelle (nucleolus, nuclear envelope, cell membrane, mitochondria, lysosome, ribosome, peroxisome, endoplasmic reticulum (rough endoplasmic reticulum, smooth endoplasmic reticulum, sarcoplasmic reticulum and the like), Golgi apparatus, microtubule, centrosome, actin filament and the like), cytosol, synapse, basement membrane, intercellular adhesion apparatus and the like. The term "protein complex" means two or more proteins in a physically conjugated state. These are concrete examples, and the present invention is not limited to these.

The term "biological molecule" used in the present invention means a protein, a lipid, a sugar chain or a nucleic acid, or, a combination thereof, and preferably a protein. In addition, it goes without saying that biological molecules include those that have received a physiological modification (for instance, phosphorylated protein and the like).

The term "protein" used in the present invention includes a peptide in which two or more amino acids are bonded by a peptide bond.

The term "metabolically isotope labeled biological molecule" used in the present invention means a biological molecule labeled metabolically by adding an isotope labeled precursor of the biological molecule. The above-mentioned "metabolically" means a physiologically condition via an enzymatic reaction or the like, and preferably a metabolic reaction in a cultured cell.

The term "precursor" used in the present invention means a molecule that may become a component of a biological molecule. A precursor, when the biological molecule is a protein, is preferably an amino acid, more preferably an essential amino acid, for instance, a leucine, an isoleucine, a tryptophan, a methionine, a lysine, a phenylalanine, a valine or a threonine, and particularly preferably a leucine, when the biological molecule is a lipid, for instance a sphingolipid, serine is preferred, in case of a sugar, is preferably a glucose, in case of a nucleic acid, is preferably an aspartic acid, a glutamine or a glycine, as purine nucleotides are biologically synthesized therefrom, but is not limited to these. In other words, the type of a precursor is not limited, as long as it is incorporated into a biological molecule.

The term "internal standard substance" used in the present invention means a substance that is added in a given amount to a sample when quantitating a substance to be measured in a mass spectroscopic device, mainly to correct the variation in the quantitative value at each experiment.

The term "internal standard substance that is a metabolically isotope labeled biological molecule" used in the present invention means an internal standard substance that contains one or a plurality of metabolically isotope labeled biological molecules.

The term "a cell containing an internal standard substance that is a metabolically isotope labeled biological molecule" used in the present invention means a cell containing an internal standard substance that contains one or a plurality of metabolically isotope labeled biological molecules.

The term "quantitation" used in the present invention broadly includes absolute quantitation and relative quantitation. The term "absolute quantitation" used in the present invention is a quantitation method with the object of obtaining a measurement result as a quantity or a concentration, and "relative quantitation" means a quantitation method other than absolute quantitation.

The term "sample that is unable to be labeled metabolically" used in the present invention means a sample other than a sample that is able to be labeled metabolically. A sample that is able to be labeled metabolically means a sample that is able to be labeled metabolically without receiving the influence of an isotope labeled precursor of the biological molecule due to culturing. A "sample that is unable to be labeled metabolically" includes, for example, samples that can be labeled metabolically while receiving the influence of an isotope labeled precursor of the biological molecule due to culturing and samples that is able to be labeled by introduction into an organism, tissue culture, and other methods.

The term "sample that is unable to be labeled by cell culture" used in the present invention means a sample in which a cell is unable to be cultured. In other words a sample that is able to be labeled by introduction into an organism, tissue culture, and other methods except cell culture, without being able to culture a cell, is deemed included in "sample that is unable to be labeled by cell culture". Examples of "sample that is unable to be labeled by cell culture" include, for instance, tissue, biological fluid, cell organ or protein complex.

FIRST EMBODIMENT OF THE PRESENT INVENTION

The present invention provides an internal standard substance that is a metabolically isotope labeled biological molecule, a cell containing an internal standard substance that is a metabolically isotope labeled biological molecule, a reagent containing the internal standard substance, a reagent containing the cell that contains the internal standard substance, and the like.

In the following, a method for preparing an internal standard substance that is a metabolically isotope labeled biological molecule and a cell containing an internal standard substance that is a metabolically isotope labeled biological molecule will be described in particular.

The cell containing an internal standard substance that is a metabolically isotope labeled biological molecule is a cell of the same species as the sample to be measured, preferably derived from the same tissue, in particular preferably easy to grow in a culture medium containing an isotope, but is not limited to these. A cell containing an internal standard substance that is a metabolically isotope labeled biological molecule selection can be prepared by culturing the selected cell in a culture medium containing a component as an isotope labeled precursor of the biological molecule. Any culture condition is adequate, and it suffices to select conditions suitable for culturing the living cell in a liquid culture medium or a solid culture medium. For instance, if an animal cell is selected, a culture can be carried out using a culture medium such as DMEM, MEM, RPMI1640 or IMDM, adding as necessary serum such as fetal bovine serum (FCS), amino acid, glucose, penicillin or streptomycin, and the like, at a pH of approximately 6 to 8, at 30 to 40° C., for around 15 to 200 hours. Otherwise, replacement of the culture medium midway, aeration and stirring can be carried out, as necessary.

Although a radioisotope can be applied for the isotope, the use of a stable isotope is preferred. For the stable isotope, preferably 2H, $^{13}C$, $^{15}N$, $^{17}O$, $^{18}O$, $^{33}P$ or $^{34}S$, or a combination thereof, in particular preferably $^{13}C$ is used, but the isotope is not limited to these. In other words, the type of the isotope used in the present invention is not limited, as long as it may be incorporated into a cell and label a biological molecule. Examples of a precursor of an isotope labeled biological molecule include, $^{13}C$ labeled ($^{13}C\times6$) leucine (manufactured by Cambridge Isotope Labs (CIL), L-Leucine U-$^{13}C6$, CLM-2262) or the like.

The cell containing the internal standard substance that is the metabolically isotope labeled biological molecule obtained as above can be used as is, but it can also be disrupted. Examples of methods for disrupting include methods using a dounce-type Teflon® homogenizer, Polytron, a Waring blender, a potter-type glass homogenizer, a sonicator, a cell lysis solution (for instance, M-PER: cat no. 78501, T-PER: cat no. 78510 and the like, from PIERCE) or the freeze thawing method, and the method using a cell lysis solution is preferred. As necessary, the protein can be quantitated. In this way, the internal standard substance that is the metabolically isotope labeled biological molecule can be prepared. These internal standard substance that are metabolically isotope labeled biological molecules or cells containing the internal standard substance that is the metabolically isotope labeled biological molecule can be conserved under adequate conditions, preferably at −20° C. or below, in particular preferably at −80° C. or below.

The present invention provides a method for quantitating a biological molecule in a sample with a mass spectrometer, in which an internal standard substance that is a metabolically isotope labeled biological molecule or a cell containing an internal standard substance that is a biological molecule is added to a sample.

This quantitation method comprises the step of: adding to a sample, an internal standard substance that is a metabolically isotope labeled biological molecule or a cell containing an internal standard substance that is a metabolically isotope labeled biological molecule; extracting, fractionating and the like biological molecule from each sample; measuring with a mass spectroscopic device; and determining from the results obtained with the mass spectroscopic device a ratio of intensities between a labeled peak and an unlabeled peak for each biological molecule to quantitate the biological molecule.

In addition, the program according to the present invention, as described below, causes each step of the quantitation or analysis method of the present invention to be executed on a computer. The program according to the present invention can be installed or downloaded onto a computer through various storage media, such as, a CD-ROM, a magnetic disk and a semiconductor memory.

A detailed description is given in the following.

<Method for Preparing a Measurement Sample for Mass Spectrometry>

An internal standard substance that is a metabolically isotope labeled biological molecule or a cell containing an internal standard substance that is a metabolically isotope labeled biological molecule, preferably a given quantity of an internal standard substance that is a metabolically isotope labeled biological molecule or a cell containing an internal standard substance that is a metabolically isotope labeled biological molecule, is added to a sample.

Then, the sample to which the internal standard substance that is the metabolically isotope labeled biological molecule or the cell containing the internal standard substance that is the metabolically isotope labeled biological molecule has been added can be disrupted, a biological molecule, preferably a protein, is extracted, then fractionated. This serves as a fractionated sample. Examples of method for disrupting/extracting include methods using a dounce-type Teflon® homogenizer, Polytron, a Waring blender, a potter-type glass homogenizer, a sonicator or a cell lysis solution (for instance, M-PER: cat no. 78501, T-PER: cat no. 78510 and the like by Pierce), or the freeze thawing method, and methods using a dounce-type Teflon® homogenizer or a potter-type glass homogenizer are preferred. Examples of fractionation method include fractionation centrifugation, sucrose density gradient centrifugation and the like, and sucrose density gradient centrifugation is preferred.

Next, the fractionated sample can be purified, as necessary. This serves as a purified sample. Examples of purification method include group specific affinity column purification, methods using cation exchange chromatography, anion exchange chromatography or reverse phase chromatography, immunoprecipitation method, ammonium sulfate precipitation method, precipitation method by an organic solvent, ultrafiltration method, gel filtration method, dialysis and the like, and the group specific affinity column purification is preferred. Each manipulation of disruption/extraction, fractionation and purification, is not limited to these, and can be suitably selected and also combined, according to technical common knowledge in those skilled in the art.

Thereafter, as necessary, the purified sample can be subjected to separation and digestion. This serves as a separated sample and a digested sample. For the separation method, two-dimensional electrophoresis, SDS PAGE, various chromatographies (for instance, affinity chromatography, reverse phase chromatography, anion exchange chromatography, cation exchange chromatography, and the like), and the like, can be used without limitation to these, and a suitable method is adequately selected. Examples of digestion method include enzyme digestion, chemical decomposition, and the like, preferably enzyme digestion, without limitation to this, and a suitable method is adequately selected. Examples of enzyme used in enzyme digestion include trypsin, chymotrypsin, Lys-C, Asp-N, Glu-C, and the like, and trypsin is preferred.

The fractionated sample, purified sample, separated sample or digested sample obtained in this way can be separated by high performance liquid chromatography (HPLC). This serves as a sample separated by HPLC. For the column used in HPLC, a suitable column is adequately selected according to technical common knowledge in those skilled in the art, and an anion exchange column or a cation exchange column is preferred. Conditions for HPLC (flow rate, detector, mobile phase, and the like) can be suitably selected according to technical common knowledge in those skilled in the art.

<Method for Measuring a Measurement Sample for a Mass Spectroscopic Device>

Next, a measurement sample obtained by the above manipulation (referring to the fractionated sample, purified sample, separated sample, digested sample or sample separated by HPLC) is measured with a mass spectroscopic device. For the mass spectroscopic device, a multipurpose device such as for gas chromatography mass spectrometry (GC/MS), which is a mass spectroscopic device bound to a gas chromatograph, or for liquid chromatography mass spectrometry (LC/MS), which is a device bound to a liquid chromatograph, can be used to carry out the above measurement. The ionization method in the mass spectroscopic device can be suitably selected according to each device. Examples include, for instance, MALDI (Matrix Assisted Laser Desorption Ionization method), ESI (Electrospray Ionization method), EI (Electron Ionization method), CI (Chemical Ionization method), APCI (Atmospheric Pressure Chemical Ionization method), FAB (Fast Atom Bombardment method), LD, FD, SIMS, TSP, and the like, and MALDI or ESI is preferred. The analyzer can be suitably selected according to each device. Analysis can be carried out using a multipurpose device, such as, for instance, TOF (Time Of Flight type), ion trap, double focusing type, quadrupole type or Fourier transform type. The device and method for mass analysis are not limited to those given herein, and those suitably used in general for mass analysis may be appropriately selected by those skilled in the art.

<Method for Identifying Biological Molecule>

Using data obtained as a result of measurement by mass analysis, a biological molecule, preferably a protein, can be identified. Analyzing the obtained data by using a commercially available software, for instance, SonarMSMS (Genomic solution) and a database, for instance, database such as NCBInr (http:www.ncbi.nlm.nih.gov/), IPI and Sport, automatic identification of a protein in a sample is possible. Identifying a protein using measurement data on mass analysis is easy for those skilled in the art (Nat Genet. 1998: 20, 46-50; J Cell Biol. 1998: 141, 967-977; J Cell Biol. 2000: 148, 635-651; Nature. 2002: 415, 141-147; Nature. 2002: 415, 180-183; Curr Opin Cell Biol. 2003: 15, 199-205; Curr Opin Cell Biol. 2003: 7, 21-27).

<Method for Determining and Comparing a Ratio of Intensities Between a Labeled Peak and an Unlabeled Peak of a Biological Molecule>

In the present invention, a "labeled peak of a biological molecule (hereinafter, sometimes simply referred to as labeled peak)" means the intensity of a signal derived from a metabolically isotope labeled biological molecule or the total thereof (in general represented by an area, which is understood by those skilled in the art), in a mass spectrum against m/z values (hereinafter, simply referred to as "mass spectrum") and/or a mass spectrum against a time (hereinafter, sometimes abbreviated as "mass chromatogram") obtained from the measurement result of a mass analysis.

In the present invention, an "unlabeled peak of a biological molecule (hereinafter, sometimes simply referred to as unlabeled peak)" means the intensity of a signal derived from a biological molecule that is not metabolically isotope labeled or the total thereof, in a mass spectrum and/or a mass chromatogram.

Figure 2:
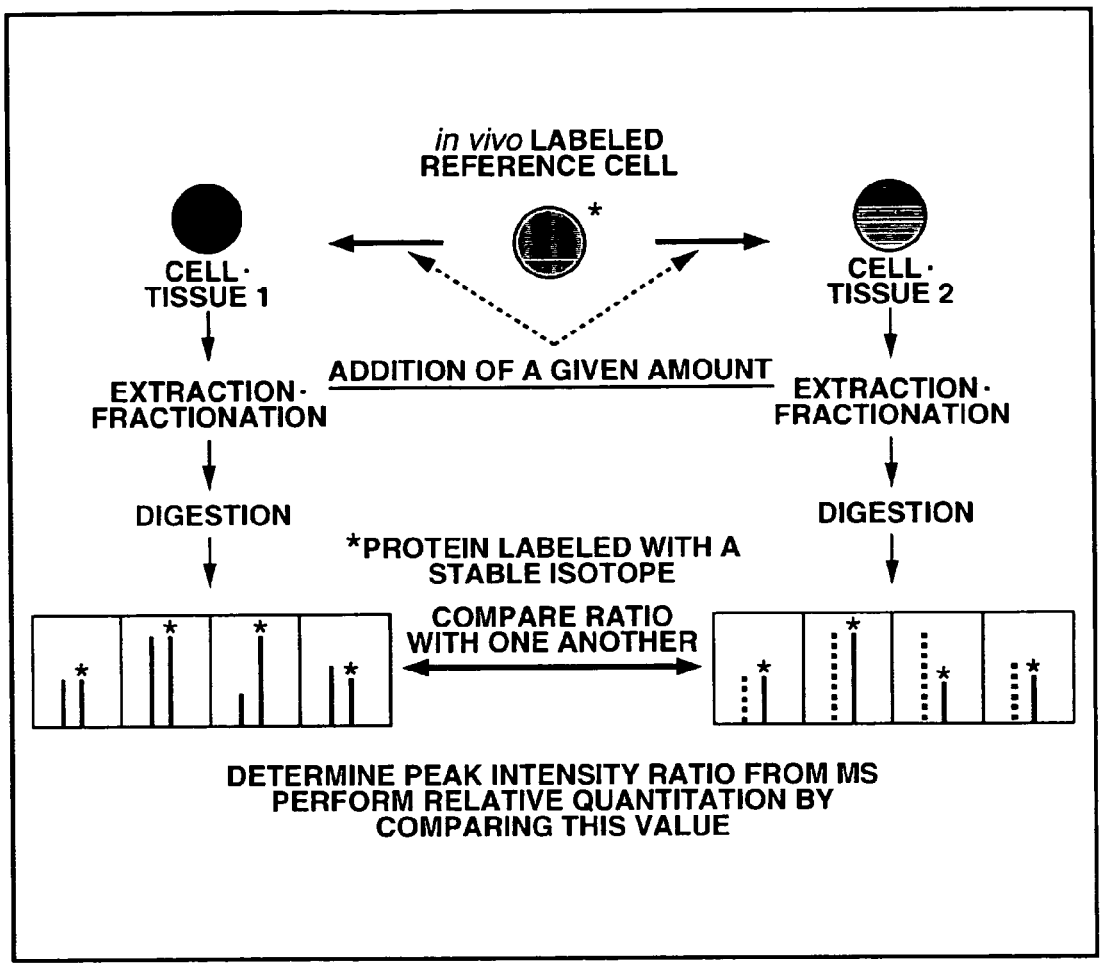
FIG. 2 shows a representation of a quantitation method according to the present invention.

Using data obtained as a result of measurement by mass analysis, by determining for each biological molecule a ratio of intensities between a labeled peak derived from an internal standard substance that is a metabolically isotope labeled biological molecule and an unlabeled peak derived from a sample, and by comparing values of the peak intensity ratio between samples, a biological molecule between samples can be quantitated relatively. A metabolically isotope labeled biological molecule has a molecular weight that is larger by an amount of isotope labeled molecular weight as compared to a biological molecule derived from a sample, and is observed in a mass analysis as a peak pair (see FIG. 2). The molecular weight of the isotope labeled biological molecule can be determined by calculating from the identified protein, lipid, sugar chain or nucleotide sequence.

More specifically, for instance, when comparing amounts of biological molecule contained in sample A and sample B, by dividing the unlabeled peak of each biological molecule in sample A with the labeled peak of the internal standard substance corresponding to the biological molecule, unlabeled peak/labeled peak (peak intensity ratio A) in the biological molecule can be determined. On the other hand, by dividing the unlabeled peak of each biological molecule in sample B with the labeled peak of the internal standard substance corresponding to the biological molecule, unlabeled peak/labeled peak (peak intensity ratio B) in the biological molecule can be determined. Next, the biological molecules in sample A and sample B can be quantitated relatively by comparing peak intensity ratio A and peak intensity ratio B.

Note that a biological molecule (for instance, protein or the like) sometimes exists, which is present in a sample and not present in an internal standard substance that is a metabolically isotope labeled biological molecule or a cell containing an internal standard substance that is a metabolically isotope labeled biological molecule. In this case, quantitation is carried out by determining peak intensity ratios with as the subject peaks derived from an internal standard substance that is close as measured with a mass spectroscopic device, preferably, peaks with a close elution time in chromatography in the case of LC/MS, and peaks with a close molecular weight in the case of MALDI-MS, and comparing the peak intensity ratios between samples. Therefore, all the biological molecules (for instance, proteins) in a sample can be measured.

More specifically, when comparing a biological molecule X in sample A and sample B, sometimes biological molecule X is not present in an internal standard substance, and a biological molecule Y is present in the vicinity. Herein, vicinity means a peak derived from an internal standard substance, and, a peak with a close elution time in chromatography in the case of LC/MS, and a peak with a close molecular weight in the case of MALDI-MS. In this case, by dividing an unlabeled peak of biological molecule X in sample A with a labeled peak of an internal standard substance corresponding to biological molecule Y, unlabeled peak in biological molecule X/labeled peak in biological molecule Y (peak intensity ratio C) can be determined. On the other hand, by dividing an unlabeled peak of biological molecule X in sample B with a labeled peak of an internal standard substance biological corresponding to molecule Y, unlabeled peak in biological molecule X/labeled peak in biological molecule Y (peak intensity ratio D) can be determined. Next, a biological molecule in sample A and sample B can be quantitated relatively by comparing the peak intensity ratio C and the peak intensity ratio D. The accuracy of the measurements can be increased by selecting a plurality of close biological molecules.

According to the present invention, absolute quantitation of one or a plurality of biological molecules, preferably proteins, used in the mass analysis becomes possible. In addition, concomitantly, an internal standard substance that is a metabolically isotope labeled biological molecule with one or a plurality of biological molecules in known quantities and a cell containing an internal standard substance that is a metabolically isotope labeled biological molecule with one or a plurality of biological molecules in known quantities, are provided.

In other words, with use of a known quantity of each biological molecule standard material, preferably a protein standard material, by determining absolute quantity of biological molecules, preferably proteins, present in an internal standard substance that is a metabolically isotope labeled biological molecule or a cell containing an internal standard substance that is a metabolically isotope labeled biological molecule, absolute quantitation of a biological molecule, preferably a protein, contained in a target sample is possible. Therefore, absolute quantitation not possible with quantitative proteome analysis so far becomes possible. By determining in this way the absolute quantity of an isotope labeled biological molecule, thereafter, an internal standard substance that is the isotope labeled biological molecule or a cell containing an internal standard substance that is a metabolically isotope labeled biological molecule can be used in various experiments, which is very useful compared to a conventional method in which quantitation had to be carried out for each experiment.

A detailed description is given in the following.

<Method for Quantitating a Biological Molecule Contained in an Internal Standard Substance that is a Metabolically Isotope Labeled Biological Molecule>

The absolute quantity of a biological molecule present in an internal standard substance that is a metabolically isotope labeled biological molecule or a cell containing an internal standard substance that is a metabolically isotope labeled biological molecule can be determined by using a known quantity of a biological molecule standard material and measuring with a mass spectroscopic device.

Specifically, for instance, a known quantity of chemically synthesized biological molecule is added to an internal standard substance that is a metabolically isotope labeled biological molecule or a cell containing an internal standard substance that is a metabolically isotope labeled biological molecule, and disruption, extraction, fractionation and purification are carry out as necessary, by the above-mentioned method. Then, measurement with the mass spectroscopic device is carried out, and by comparing the peak derived from the chemically synthesized biological molecule and the labeled peak, the absolute quantity of the biological molecule present in the internal standard substance that is the metabolically isotope labeled biological molecule or the cell containing the internal standard substance that is the metabolically isotope labeled biological molecule can be determined.

When the biological molecule is a protein, measurement is carried out by SDS-PAGE, EIA, ELISA, RIA, western blot and flow cytometry, in addition to the above methods. These are exemplary, and a method thought to be optimal by those skilled in the art can be used, without limitation to this.

More specifically, a given quantity of an internal standard substance that is a metabolically isotope labeled biological molecule or a cell containing an internal standard substance that is a metabolically isotope labeled biological molecule is disrupted, and the protein extracted, under adequate conditions, preferably under the same conditions as the measurement sample preparation method above. By measuring a target protein in this extract by a method such as SDS-PAGE, EIA, ELISA, RIA, or western blot, the absolute quantity of the biological molecule present in the internal standard substance that is the metabolically isotope labeled biological molecule or the cell containing the internal standard substance that is the metabolically isotope labeled biological molecule is determined.

In addition, when the biological molecule has an activity, such as an enzyme, a specific activity (intensity of activity per protein quantity) that is specific to this biological molecule can be determined. For the specific activity specific to a substance, a reported activity may be used, or it may be measured and determined. Therefore, the absolute quantity of the biological molecule present in the internal standard substance that is the metabolically isotope labeled biological molecule or the cell containing the internal standard substance that is the metabolically isotope labeled biological molecule can be determined, by measuring the activity that the protein in the above extract has.

Note that in the present invention the subject of quantitation is not limited to a protein, and the present invention can be applied to analyses having the object of quantitating and identifying all the substances produced by the cell using the nutrients in a culture medium, such as, for instance, lipid, sugar chain or nucleic acid.

It should be noted that a program according to the present invention for executing the method for determining and comparing the ratio of intensities between a labeled peak and an unlabeled peak of a biological molecule, and the method for quantitating a biological molecule contained in an internal standard substance that is a metabolically isotope labeled biological molecule is described below.

SECOND EMBODIMENT OF THE PRESENT INVENTION

Figure 3:
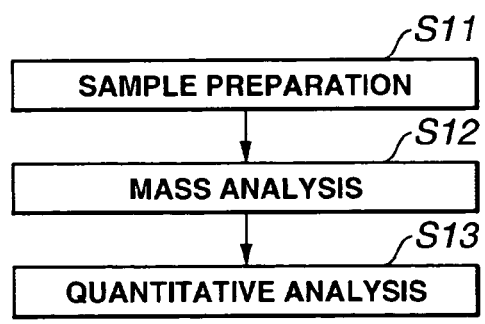
FIG. 3 shows an overall scheme summarizing a quantitative analysis method for a biological molecule according to the present invention.

FIG. 3 shows an overall scheme summarizing a method according to the second embodiment of the present invention for a quantitatively analyzing a protein as one example of biological molecule. As shown in FIG. 3, first, a measurement sample preparation is carried out, mass analysis is then carried out using a mass spectroscopic device. Next, the quantitative analysis method according to the present invention is executed.

The measurement sample preparation shown in step S11 of FIG. 3 comprises the steps of: isotope labeling a sample; extracting and fractionating a biological molecule from each sample and the like. Examples of the methods for isotope labeling the sample include the method of culturing in a culture medium containing an isotope labeled amino acid, the method of isotope labeling chemically or enzymatically in vitro, and the like.

The method of culturing in the culture medium containing the isotope labeled amino acid comprises the step wherein a protein biologically synthesized by the addition of an isotope labeled amino acid metabolically incorporates an isotope labeled amino acid into a non-isotope labeled cell grown and/or cultured in an environment not containing an isotope labeled amino acid, so as to create an isotope labeled protein having the isotope labeled amino acid.

The culture condition for the method of culturing in the culture medium containing the isotope labeled amino acid may be any conditions, and it suffices to set conditions that are optimal for culturing the cells in a liquid culture medium or a solid state culture medium. For example, the culture can be carried out according to the method explained in the above first embodiment of the present invention, and if an animal cell is selected, a culture can be carried out using a culture medium such as DMEM, MEM, RPMI1640 or IMDM, adding as necessary serum such as fetal bovine serum (FCS), amino acid, glucose, penicillin or streptomycin and the like, at a pH of approximately 6 to 8, at 30 to 40° C., for around 15 to 200 hours. Otherwise, replacement of the culture medium midway, aeration and stirring can be carried out, as necessary. The cell containing the isotope labeled protein obtained in this way can be used as is, but it can also be disrupted prior to use. Examples of methods for disrupting include methods using a dounce-type Teflon homogenizer, Polytron, a Waring blender, a potter-type glass homogenizer, a sonicator, a cell lysis solution (for instance, M-PER: cat no. 78501, T-PER: cat no. 78510 and the like, from PIERCE) or the freeze thawing method, and the method using a cell lysis solution is preferred.

In addition, in the second embodiment of the present invention, an isotope labeled protein can also be prepared in vitro. For example, isotope labeling is carried out by alkylating a cysteine residue in a protein using an isotope labeled alkylating reagent (see "Rapid Communications in Mass Spectroscopy" Volume 16, No. 15, 2002, pp. 1416-1424). Further, isotope labeling is also carried out by biotinylating a cysteine residue in a protein using an isotope labeled biotinylation reagent. Furthermore, using an avidin column, it is possible to purify the labeled protein only ("Nature Biotechnology" Volume 17, No. 10, October 1999, pp. 994-999).

Moreover, the C-terminus, the N-terminus, a glutamic acid residue, an aspartic acid residue and the like of a peptide fragment obtained by digesting a protein, can be labeled with an isotope labeled molecule. Specifically, when a protein is digested with an enzyme, water labeled with $^{18}O$ is added in the buffer solution. Chymotrypsin, trypsin, Asp-N, Lys-C or Glu-C can be used as a digestion enzyme. It is well-known that when chymotrypsin or Asp-N is used, one $^{18}O$ is on the C-terminus side of the peptide after hydrolysis, and when trypsin, Lys-C or Glu-C is used, both oxygen atoms on the carboxylic acid at the C-terminus of the peptide after hydrolysis become $^{18}O$.

It is also well-known that there is a method for converting into methyl ester a carboxylic acid of the C-terminus, a glutamic acid residue or an aspartic acid residue of a peptide fragment obtained by digesting a protein (see Goodlett D R, Keller A, Watts J D, Newitt R, Yi E C, Purvine S, Eng J K, von Haller P, Aebersold, Koller E. Differential stable isotope labeling of peptides for quantitation and de nove sequence derivation. Rapid Commun mass Spectrom. 2001: 15, pp. 1214-1221), and isotope labeling can also be carried out by methylation using isotope labeled methanol.

In addition, it is well-known that there are a method for nicotinic acid derivatizing (see Munchbach M, Quadroni M, Miotto G, James P. Quantitation and facilitated de novo sequencing of proteins by isotropic N-terminal labeling of peptides with a fragmentation-directing moiety. Anal. Chem. 2000: 72, pp. 4047-4057), a method for acetylating (see Ji. J. Chakraborty A, Geng M, Zhang X, Amini A, Bina M, Regnier F. Strategy for quantitative and quantitative analysis in proteomics based on signature peptides. J Chromatogr B Biomed Sci Appl. 2000: 745, pp. 197-210) and the N-terminus of a peptide fragment obtained by digesting a protein. Therefore, isotope labeling can also be carried out using these isotope labeled reagents.

Note that the isotope labeled protein or the cell containing the isotope labeled protein can be conserved under adequate conditions, preferably at −20° C. or less, particularly preferably at −80° C. or less. Then, the isotope labeled protein which is obtained in this way can also be used as an internal standard substance in the analysis described below.

Although a radioisotope can be applied for the isotope labeled amino acid used in the present invention, a stable isotope that does not have radioactivity, owing to the ease with which it can be handled, are in particular preferred. Examples of stable isotope include, but are not limited to, include $^2H$, $^{13}C$, $^{15}N$, $^{17}O$, $^{18}O$, $^{33}P$ or $^{34}S$, or a combination thereof, and $^{13}C$ is preferred. The type of isotope used in the present invention is not limited in particular, as long as it may be incorporated into a cell and label a protein. Specifically, $^{13}C$ labeled ($^{13}C\times6$) leucine (manufactured by Cambridge Isotope Labs (CIL), L-Leucine U-13C6, CLM-2262) can be exemplary as a precursor of the isotope labeled protein.

Figure 4:
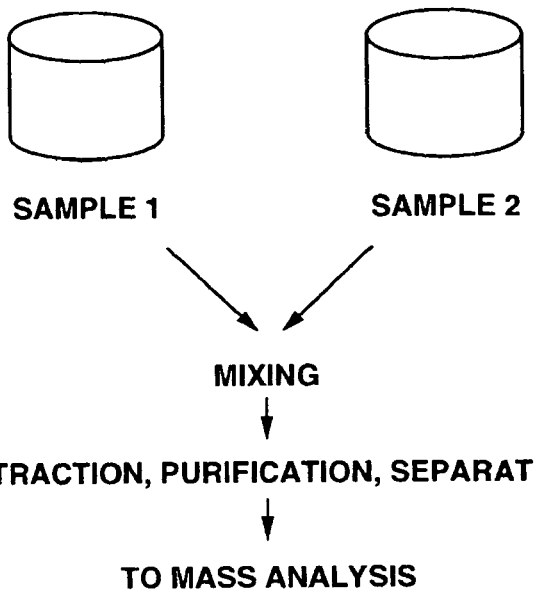
FIG. 4 shows a scheme of one aspect of measurement sample preparation using isotope labeling according to the present invention.

FIG. 4 shows a scheme of one aspect of the second embodiment of the present invention, in regard to measurement sample preparation using isotope labeling according to the present invention. Among the samples to be measured, sample 1 containing an isotope labeled protein on one hand, sample 2 containing a non-isotope labeled protein on the other hand, are prepared. Then, sample 1 and sample 2 are mixed.

Next, the mixed sample is disrupted to extract protein. Then, the above sample can be purified as necessary. Examples of purification method include group specifically affinity column purification, methods using cation exchange chromatography, anion exchange chromatography or reverse phase chromatography, immuno-precipitation method, ammonium sulfate precipitation method, precipitation method by an organic solvent, exclusion filtration method, dialysis and the like.

Thereafter, as further necessary, various separations and digestions can be carried out. Examples of the separation methods include, but are not limited to, two-dimensional electrophoresis, SDA PAGE, various chromatographic (for example, affinity chromatography, reverse phase chromatography, anion exchange chromatography, cation exchange chromatography, and the like), and the like. Examples of the digestion methods include, but are not limited to, enzyme digestion, chemical decomposition and the like. Examples of enzyme used in enzyme digestion include, for example, trypsin, chymotrypsin, Lys-C, Asp-N, Glu-C, and the like.

Although the sample products obtained in this way can be measured as is, they can also be separated by HPLC. Examples of column used in HPLC include, but are not limited to, an anion exchange column, a cation exchange column and the like. Conditions for HPLC (flow rate, detector, mobile phase) are easily understood by those skilled in the art, and can be selected suitably.

In step S12 shown in FIG. 3, mass analysis is carried out on the sample prepared as above. For this mass analysis, a multipurpose device such as gas chromatography mass spectrometry (GC/MS), which is a mass spectroscopic device bound to a gas chromatograph, or liquid chromatography mass spectrometry (LC/MS), which is a mass spectroscopic device bound to a liquid chromatograph, can be used. The ionization method for mass analysis can be suitably selected according to each device as described in the first embodiment of the present invention described above. Examples of the ionization include, for example, MALDI, ESI, EI, CI, APCI, FAB, LD, FD, SIMS, TSP, and the like. The analyzer can be suitably selected according to each device. Analysis can be performed using a multipurpose device, such as, TOF, ionic trap, double focusing type, quadrupole type, or Fourier transform type.

A protein can be identified using data obtained from the result of measurement by mass analysis. An automatic identification of the obtained data in relation to the protein can be carried out using a commercial software, for example, SonarMSMS (Genomic Solution), and a database, for example, a database such as NCBInr (http://www.ncbi.nlm.nih.gov/), IPI or Sport. Identifying a protein using measurement data on mass analysis, can be easily understood by those skilled in the art (for example, see Nat Genet. 1998: 20, 45-50; J Cell Biol. 1998: 141, 967-977; J Cell Biol. 200: 148, 635-651; Nature, 2002: 415, 141-147; Nature. 2002: 415, 180-183; Curr Opin Cell Biol. 2003: 15, 199-205; Curr Opin Cell Biol. 2003: 7, 21-27).

The analysis method according to the present invention allows for the quantitative analysis of the protein in the sample shown in step S13 of FIG. 3, by determining, briefly, by using data obtained from the result of the measurement by mass analysis, for each protein, a ratio of intensities between a peak derived from an isotope labeled protein which is an internal standard substance and a peak derived from a protein in a sample, more specifically, a waveform separated mass chromatogram derived from an individual protein, and comparing between samples the values of these peak intensity ratios, or an areas of waveforms. For example, as described in the first embodiment of the present invention, the step of adding the internal standard substance that is the metabolically isotope labeled biological molecule or the cell containing the internal standard substance that is the metabolically isotope labeled biological molecule, the step of extracting and fractionating a biological molecule from each sample, are carried out in step S13 shown in FIG. 3. Then, the biological molecule is measured with a mass spectroscopic device (see step S12 of FIG. 3). Thereafter, in a quantitative analysis shown in step S13 in FIG. 3, the result obtained in the mass spectroscopic device is acquired, once a labeled peak and an unlabeled peak of each biological molecule are selected, the ratio of each peak intensity is determined, allowing the biological molecule to be quantitated.

Figure 5:
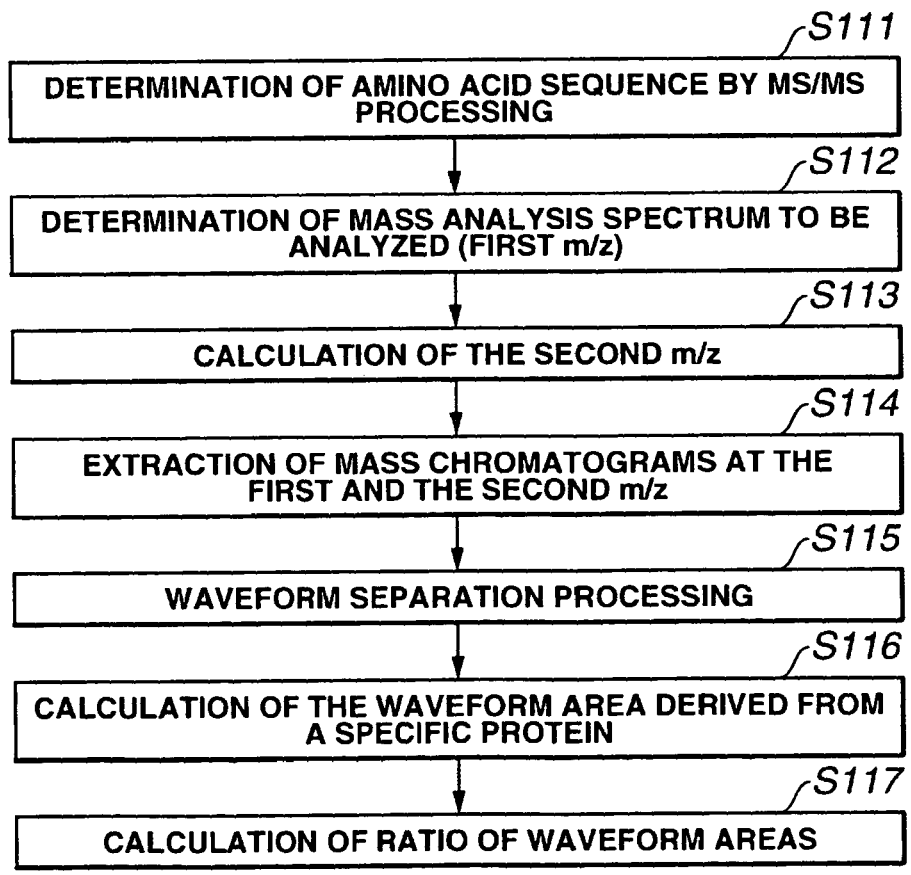
FIG. 5 shows a scheme of the quantitative analysis method according to the present invention, after a mass analysis.

FIG. 5 shows a scheme of the quantitative analysis method according to the present invention, after the mass analysis in the mass spectroscopic device. As shown in FIG. 5, the quantitative analysis method according to the present invention comprises a determination of an amino acid sequence by MS/MS processing of a mass analysis spectrum of an analysis sample (step S111), a determination step of the mass analysis spectrum (first m/z) (step S112), a calculation, from the first m/z value of a protein for which an amino acid sequence has been determined, of a second m/z value of an isotope labeled protein that is isotope labeled with respect to the protein (step S113), an extraction of a mass analysis spectrum against a time (hereinafter, sometimes abbreviated as "mass chromatogram") at the first and second m/z values (step S114), a waveform separation on mass chromatogram of each protein corresponding to the first and second m/z values (step S115), a calculation of the area of a waveform derived from an individual protein obtained by the waveform separation processing (step S116), and a calculation, from the value of the area of first waveform corresponding to the first m/z and the value of the area of second waveform corresponding to the second m/z, the ratio (the area of the second waveform)/(the area of the first waveform) (step S117). In the following, the quantitative analysis method according to the present invention will be explained by describing each step in detail.

Note that the above analysis method is described based on a method that determines, from a mass analysis spectrum of a non-isotope labeled protein, a mass analysis spectrum of a corresponding isotope labeled protein; however, it is easily understood by those skilled in the art that the analysis method according to the present invention can also be carried out by the method of determining a mass analysis spectrum of an isotope labeled protein as an analysis subject, then determining a mass analysis spectrum of a corresponding non-isotope labeled protein.

Figure 6:
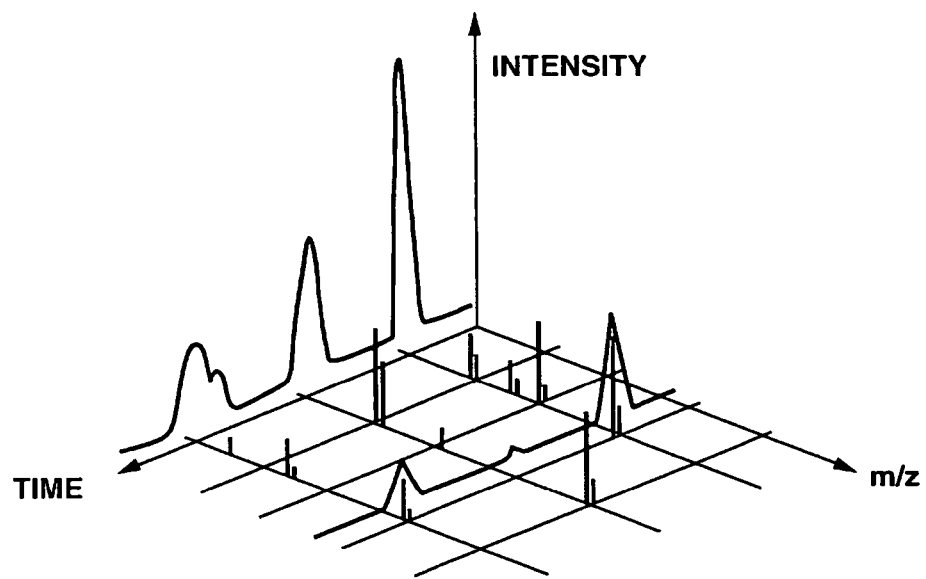
FIG. 6 shows a mass spectrum obtained with a typical mass spectroscopic device.

FIG. 6 shows a typical spectrum obtained with a mass spectroscopic device. Types of obtained spectra include, spectrum showing intensity axis against m/z from an arbitrary time axis (mass spectrum against m/z), and spectrum showing the total amount of ions detected with an intensity against each time (mass analysis spectrum against a time (hereinafter, sometimes abbreviated as "mass chromatogram").

In step S111 shown in FIG. 5, an amino acid sequence is determined by the mass spectrum obtained from MS/MS processing (step S111). Thereafter, a first m/z value of a protein to be analyzed is determined (step S112).

The above-mentioned MS/MS processing is a processing method, which uses a plurality of mass separation units, in which one among the ion species generated in the ionization chamber of the first mass separation unit (hereinafter, referred to as "MS1") is selected as a precursor ion, and product ions generated by disintegration of this precursor ion in the second mass separation unit ("MS2") are detected. Then, it carries out an analysis of amino acid sequence from the m/z value of the product ion, and the method determining an amino acid sequence by MS/MS processing is easily understood by those skilled in the art (for example, see "Post-Genomic Mass Spectrometry" 1993, pp 39-72, Toshimitsu Niwa Ed., Kagakudojin). This determination of amino acid sequence by MS/MS processing can be carried out by retrieving with the NCBInr (http://www.ncbi.nlm.nih.gov/) database via an internet.

Then, from the first m/z value of the protein for which the previous amino acid sequence has been determined, the second m/z of an isotope labeled protein corresponding to this protein is determined. When preparing a sample in step S11 shown in FIG. 3, by culturing a cell using a reagent for which a stable isotope is known, for example, $^{13}C$ labeled ($^{13}C\times6$) leucine, as amino acid to cause isotope labeling, the difference between the first m/z value and the second m/z value is worth six times $^{12}C$ and $^{13}C$, which difference is six. The second m/z value can be then calculated from the value of an electric charge of the protein, in step S113.

Mass spectra against a time at the first m/z and the second m/z values (hereinafter, respectively referred to as "first mass spectrum against a time (hereinafter, sometimes abbreviated as "first mass chromatogram")", and referred to as "second mass spectrum against a time (hereinafter, sometimes abbreviated as "second mass chromatogram")") are extracted from mass spectra obtained in the mass spectroscopic device (step S114).

Figure 7:
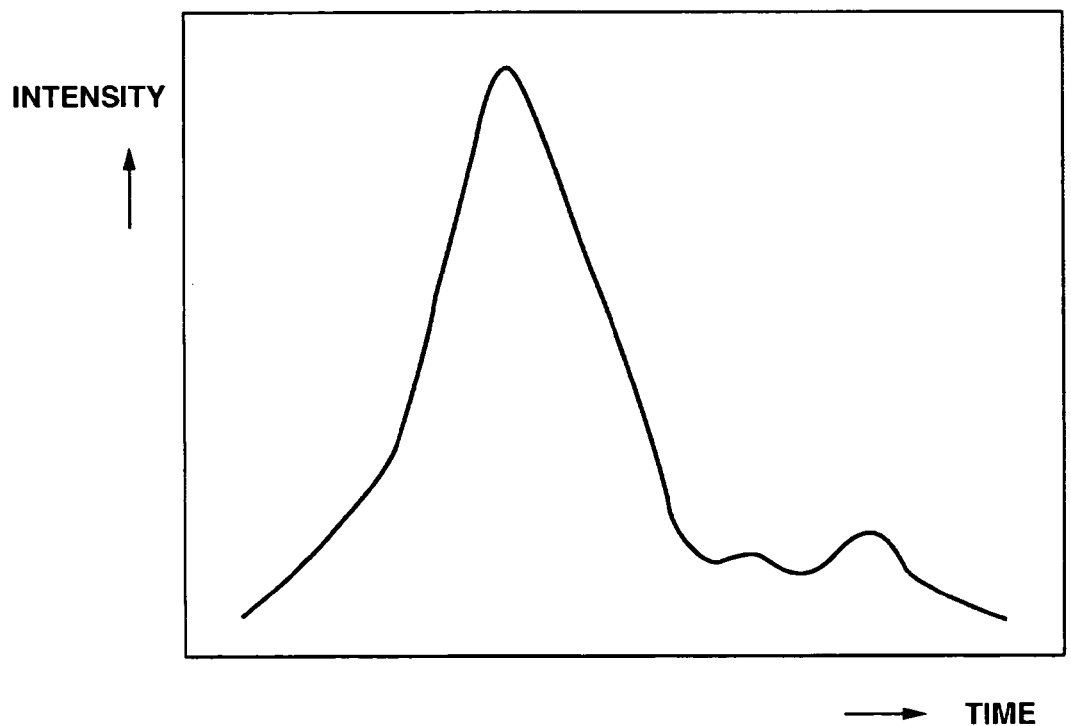
FIG. 7 shows one exemplary mass chromatogram for a single m/z value in which a plurality of peaks are overlapped.

Meanwhile, a plurality of proteins are present inside a cell, and if the masses of these numerous proteins are analyzed at once, a phenomenon in which peaks from different proteins are overlapping may be observed even if it is a single mass chromatogram. FIG. 7 shows for a single m/z value, one exemplary mass chromatogram in which a plurality of peaks are overlapped.

Due to such a phenomenon, a quantitative analysis of amounts of protein expressed in the cell is made difficult. Thus, in the present invention, a waveform separation processing is performed on the first mass chromatogram and second mass chromatogram (step S115), which are shown above, to separate into mass chromatograms derived from specific proteins.

The waveform separation processing used in the present invention is a synthetic separation method, the basis of which is a curve fitting method against a complex waveform. This assumes, first of all, that each peak component can be represented by an individual analytical function. Based on this assumption, a number of peak functions are generated/synthesized, the parameters contained in each peak function are adjusted to minimize the deviation from the observed waveform. From the parameters at the minimum deviation point, each peak waveform is decomposed/separated, to carry out this method. Note that examples of waveform parameters used in the waveform separation processing according to the present invention include the number of peaks, the shape of each peak, the peak position, the peak height, the shape of the baseline and the like.

Figure 8:
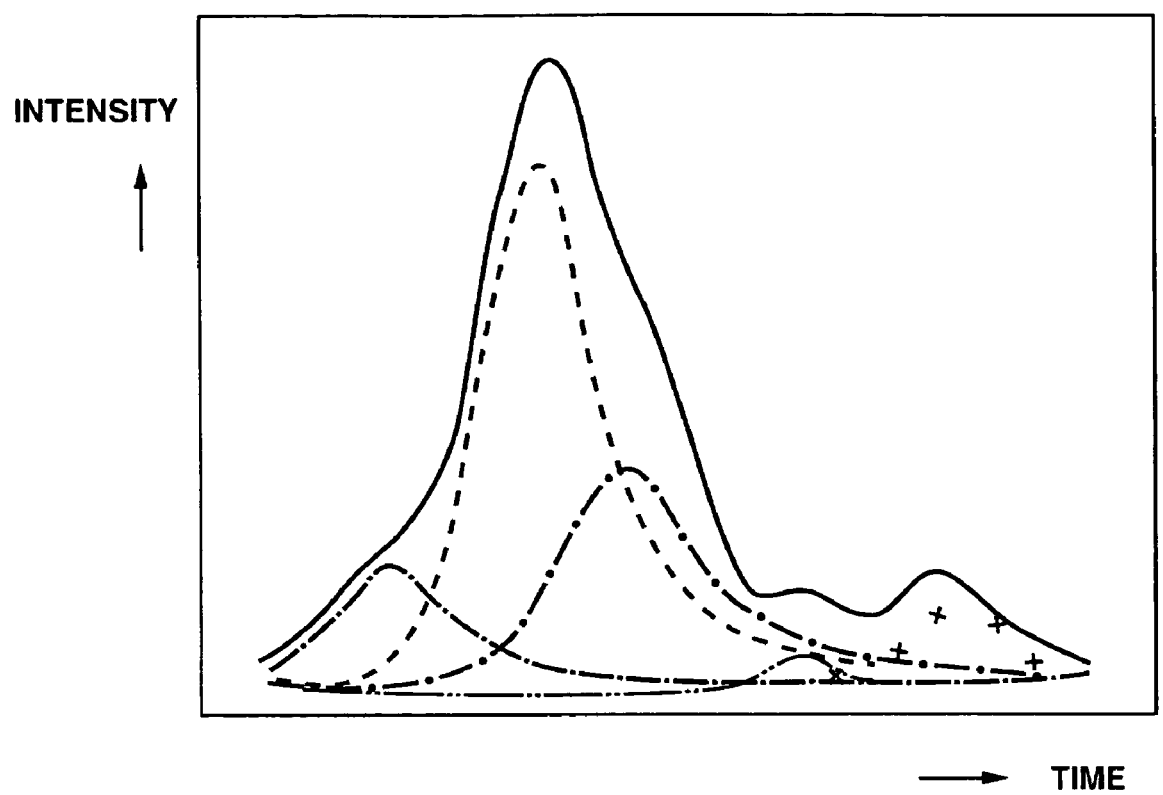
FIG. 8 shows a waveform spectra obtained by separating the spectrum shown in FIG. 7 by use of the waveform separation processing used in the present invention.

FIG. 8 shows mass chromatograms obtained by separating the mass chromatogram shown in FIG. 7 by the waveform separation processing according to the present invention. In the present invention, waveform separation can be carried out, for example, using a Gaussian function and a Lorenz function. As can be apparent from FIG. 8, due to the waveform separation processing according to the present invention, the actually measured mass chromatogram shown in solid line is separated into five by the mass chromatograms shown with broken lines and the like.

The waveform separation processing shown in FIG. 8 is executed for a non-isotope labeled protein and an isotope labeled protein corresponding thereto. The mass chromatogram obtained in this way is a mass chromatogram derived from an individual protein. Then, an area of this mass chromatogram is calculated respectively for the non-isotope labeled protein and the isotope labeled protein, respectively serving as the area of the first waveform and the area of the second waveform (step S116). Next, in step S117, a ratio (the area of second waveform)/(the area of first waveform) is determined, which is used for the quantitative analysis of protein fluctuation. This always enables a quantitative analysis by carrying out comparison with the isotope labeled protein.

Figure 9:
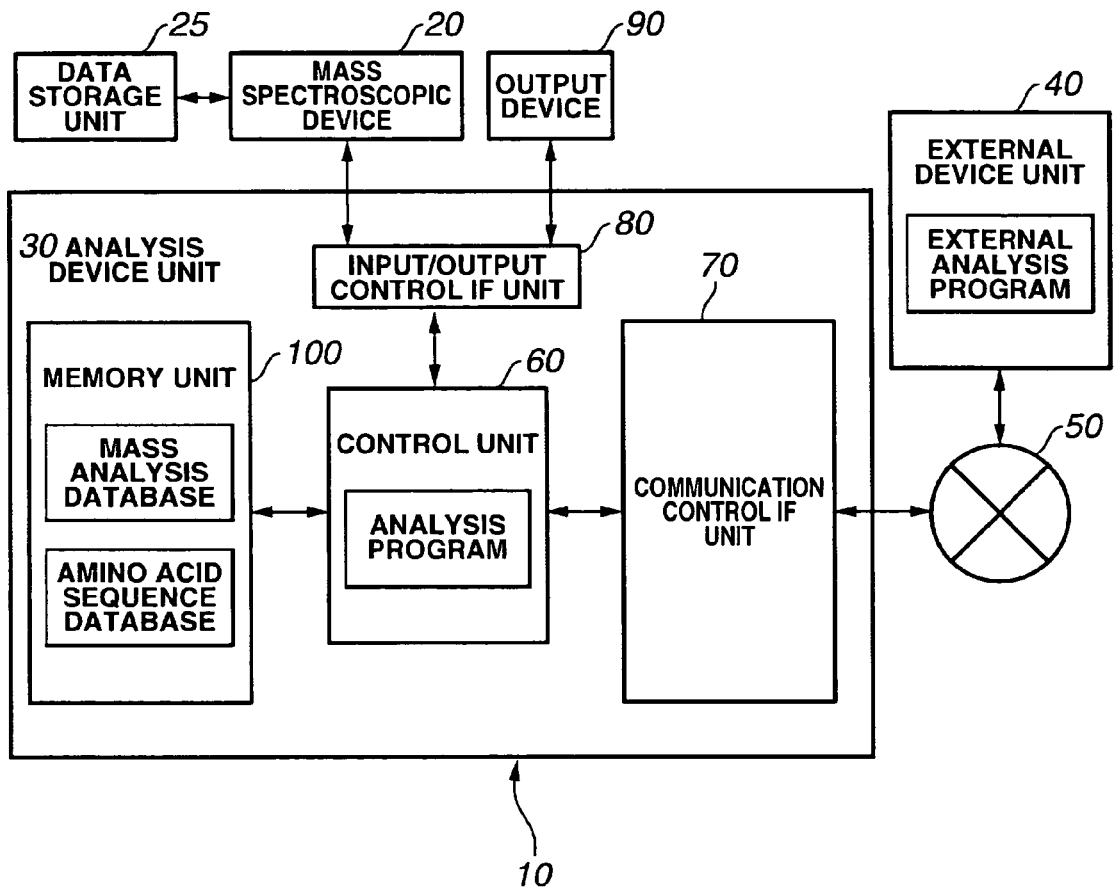
FIG. 9 shows an example of a functional block diagram of the constitution of an analysis system to which the present invention is applied.

In the following, an analysis system that causes a program pertaining to the quantitative analysis method of the present invention to execute on a computer will be described. FIG. 9 shows an example of functional block diagram of the constitution of an analysis system 10 to which the present invention is applied. Note that in FIG. 9, in the constitution, only the portions related to the present invention are shown conceptually, and the analysis system 10 is constituted by a microcomputer.

The analysis system 10 according to the present invention schematically comprises an analysis device unit 30 for analyzing a mass analysis data obtained in a mass spectroscopic device 20, and an external device unit 40 for providing an external analytical program or the like for amino acid sequence determination use, which are communicably connected via a network 50. Note that the network 50 shown in FIG. 9 has a function for reciprocally connecting the analysis device unit 30 and the external device unit 40, and is, for example, an internet or the like.

The mass spectroscopic device 20 used in the present invention is not limited in particular, and it suffices to be a mass spectroscopic device which is commercially available. Then, the mass spectroscopic device 20 may be provided with, in itself, a data storage unit 25 for storing a result obtained by carrying out a measurement in the device. In addition, the mass spectroscopic device 20 used in the present invention may be provided with, in itself, a control unit for controlling a device, or an input/output unit device.

The external device unit 40 shown in FIG. 9 is reciprocally connected to the analysis device unit 30 for analyzing a mass analysis data via a network, and is provided with a function for providing a user with an external database related to amino acid sequence information and the like, or a web site executing an external analytical program, such as, homology search.

Here, the external device unit 40 may be constituted as a WEB server, an ASP server or the like, the hardware constitution thereof may be constituted by an information processing device and device associated thereto, such as generally commercialized workstation or personal computer. In addition, each function of the external device unit 40 is realized by a CPU, a disc device, a memory device, an input device, an output device, a communication control device and the like in the hardware constitution of the external device unit, and programs or the like that control them.

In the present invention, a database such as NCBInr can be used as the external device unit.

The analysis device unit 30 shown in FIG. 9 comprises a control unit 60, such as a CPU, for controlling integrally the entirety of the mass spectroscopic device 20, a communication control interface unit 70 connected to a communication device (not shown) such as a router connected to a communication line and the like, an input/output control interface unit 80 connected to the mass spectroscopic device 20 and an output device 90 such as a display or a printer, and a memory unit 100 for storing various databases. Each unit is communicably connected via an arbitrary communication route. In addition, the analysis device unit 30 according to the present invention is communicably connected to a network via a communication device such as a router and a wired or wireless communication line such as a dedicated line.

The various databases (mass analysis data, amino acid sequence database, and the like) stored in the memory unit 100 are stored in a storage means such as a fixed disc device, and which stores files, data and the like.

Among each of the constitutive elements of the memory unit 100, the mass analysis database is a database obtained in the mass spectroscopic device 20. The amino acid sequence database may also be an amino acid sequence database obtained after analysis of mass spectra obtained in the mass spectroscopic device, or an external amino acid sequence database accessible via the Internet. In addition, it may also be an in-house database constituted by copying these databases, storing an original sequence information, and furthermore, assigning one's own identification number.

The control unit 60 stores a program for executing the analysis method according to the present invention, and is a device for controlling the analysis device unit 30, and the entirety of the analysis system 10. The control unit 60 has an internal memory (not shown) for storing a control program such as an OS (operating system), program in which various application procedures and the like have been defined, and required data, carries out with these programs and the like, information processing to execute a variety of processes. Note that the program for executing the analysis method according to the present invention may be stored in the memory unit 100.

Figure 10:
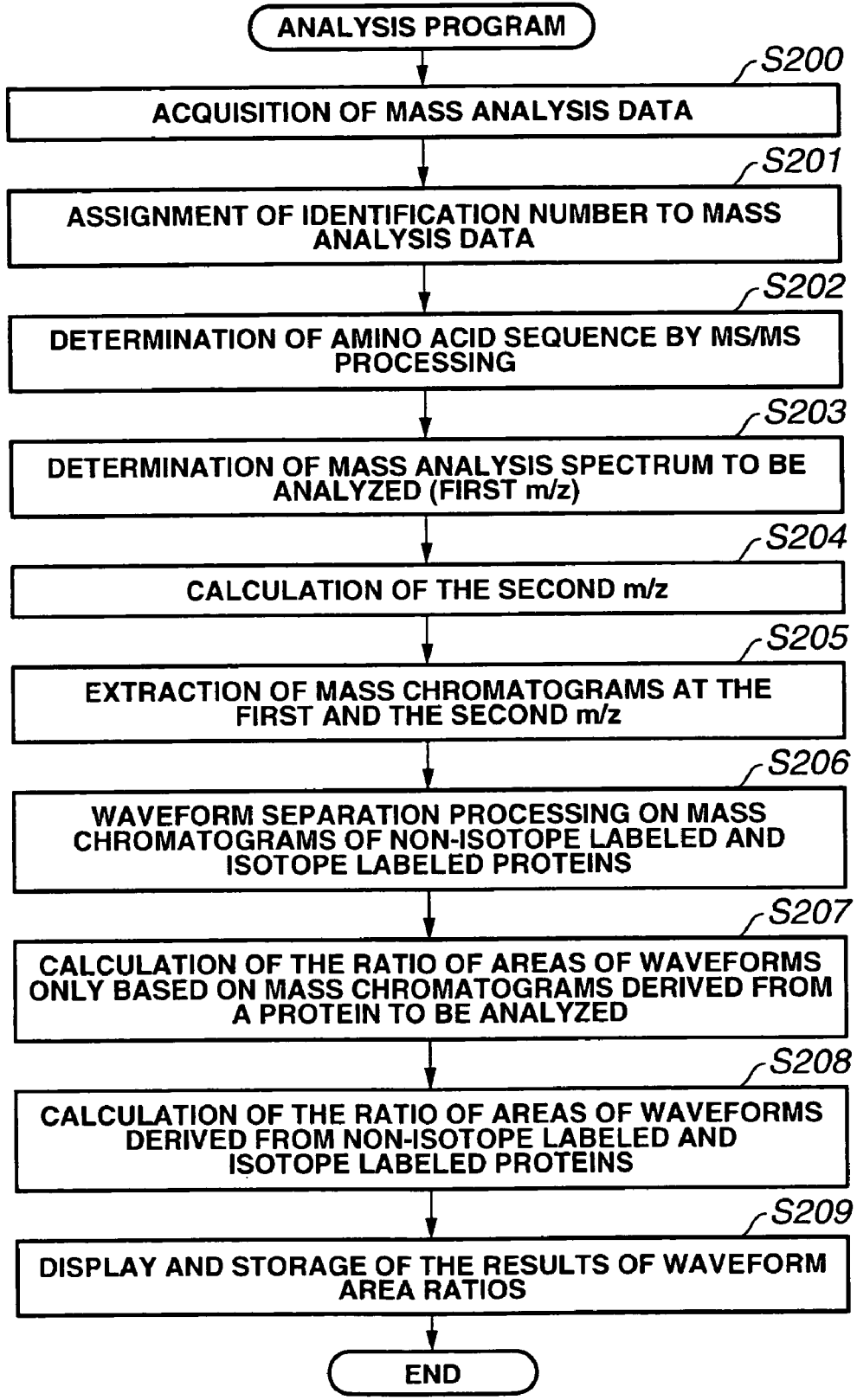
FIG. 10 shows a flowchart schematically representing a program for performing the analysis method according to the present invention.

FIG. 10 is a flowchart conceptually representing one program for executing the analysis method according to the present invention. In step S200, the control unit 60 acquires mass analysis data obtained in the mass spectroscopic device 20. Then, the acquired mass analysis data is saved in the memory unit 100, in doing so, for the convenience of the analysis described below, an identification number such as a scan number is assigned to each mass analysis data (step S201) to make data retrieval easy. Next, in the same way as described in step S111 of FIG. 5, an amino acid sequence can be determined by MS/MS processing in the control unit 60 (step S202) while retrieving with an external database through the Internet 50 via a communication control interface unit, for example, the NCBInr database. Among the mass analysis data, a mass analysis spectrum to be analyzed is determined (see step S203). In this case, the m/z of the mass analysis spectrum determined as described above is determined, which serves as a first m/z. This first m/z value may be assigned to a mass spectrum of a non-isotope labeled protein or a mass spectrum of an isotope labeled protein. The determination can be carried out easily based on the above scan number.

In step S204, from the first m/z value of the protein for which an amino acid sequence has been determined, the second m/z value of an isotope labeled protein corresponding to this protein is determined. This determination step can be determined easily from the number of isotope atoms contained in the amino acid for isotope labeling used when pre-culturing in step S11 of FIG. 3, and an electric charge of the protein corresponding to the first m/z. From the determined second m/z value, a mass chromatogram for this value is extracted from the mass analysis data stored in the memory unit 100 (see step S205).

Next, in step S206, waveform separation processing is carried out on the first mass chromatogram and the second mass chromatogram at the first m/z and second m/z values, as described in FIG. 7 and FIG. 8. With this processing, a mass chromatogram derived from an individual protein can be separated, and stored in the memory unit 100. As areas of waveforms of the mass chromatogram obtained in this way, a area of the first waveform and a area of the second waveform are calculated (step S207), and in step S208, a ratio (the area of the second waveform)/(the area of the first waveform) can be calculated.

Thereafter, according to necessary, the value of the ratio can be displayed on or printed to an output device 90 such as a display or a printer.

As a series of the steps shown in FIG. 10 is carried out while comparing with a mass spectrum originating from the isotope labeled protein, the variation of amounts of the protein expressed in the sample can be analyzed quantitatively. It is also possible to execute repeatedly the series of the steps shown in FIG. 10 on another mass spectrum to be analyzed, according to necessary. For example, it is also possible to observe a difference in the expression pattern of a protein derived from a gene deficient cell, from a comparison with a protein derived from a normal cell.

Furthermore, in FIG. 10, the description is given for a non-isotope labeled biological molecule and an isotope labeled biological molecule; however, instead of an isotope labeled biological molecule, a biological molecule that is an isotope labeled internal standard substance can also be used. In this case, the ratio of the areas of waveforms shown in step S208 of FIG. 10 can be calculated as a ratio (an area of a waveform of the biological molecule)/(an area of a waveform specific to the internal standard substance).

Figure 11:
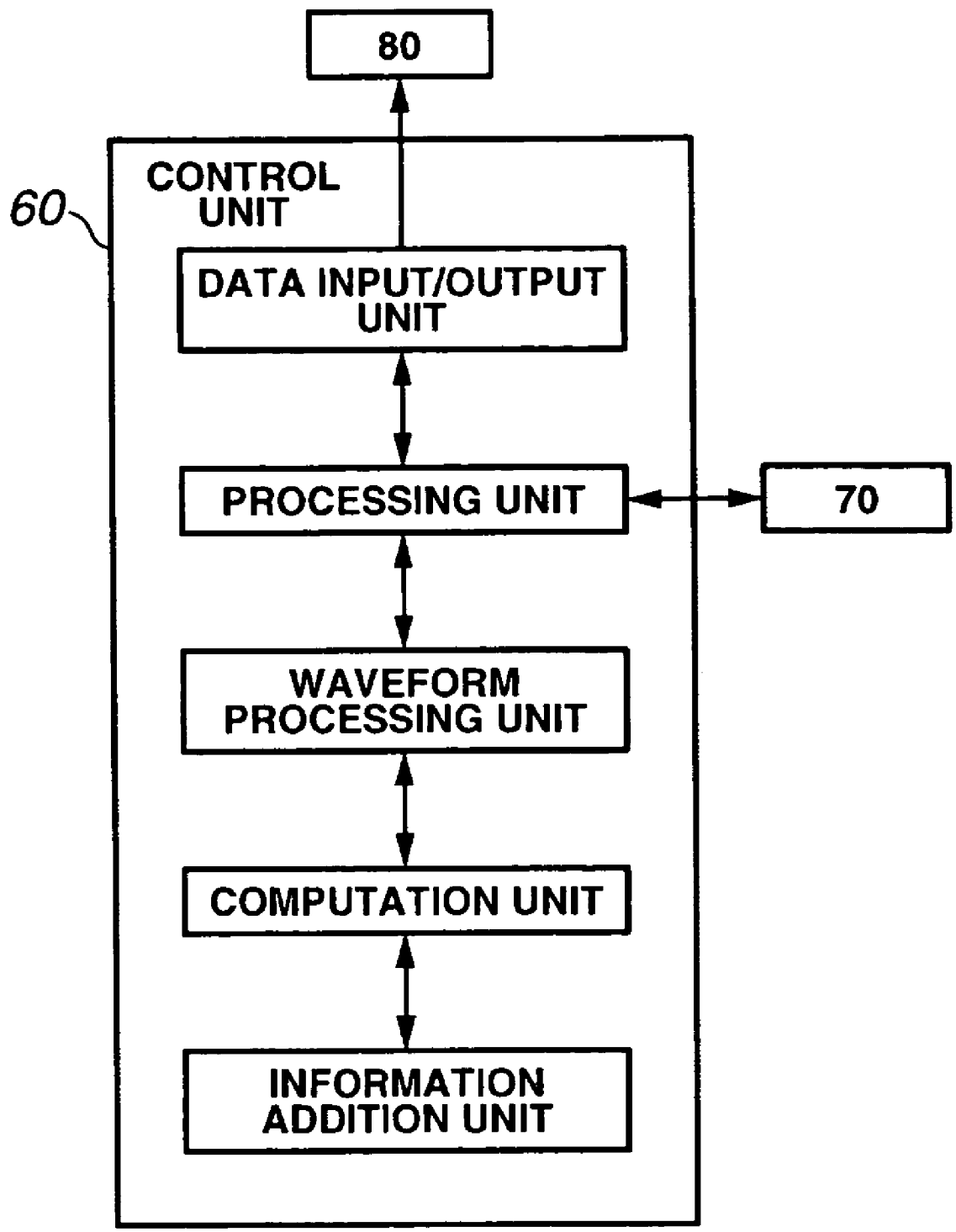
FIG. 11 illustrates a functional block diagram showing a detailed constitution of a control unit used in the present invention.

FIG. 11 is a functional block diagram showing a detailed constitution of the control unit 60 used in the present invention. As described above, the control unit 60 for executing the analysis method according to the present invention described in FIG. 10, obtains the mass analysis data obtained in the mass spectroscopic device 20, through the input control interface unit 80, in the data input/output unit of the control unit 80. While retrieving with an external database, for example, the NCBInr database, the amino acid sequence regarding the obtained protein mass analysis data is determined by MS/MS processing in the processing unit of the control unit 60. The mass spectrum to be analyzed can be determined based on a signal from an input mean, not shown, connected to the mass spectroscopic device 20, or the control unit 80. Here, examples of the input means include a keyboard, a mouse and the like, which are connected to the control unit.

The first m/z value has been determined by the determination described above, and the second m/z value is determined by the processing unit of the control unit 60. Determination of the second m/z value can be carried out by step S113 of FIG. 5. Note that the proteins of the first m/z value and the second m/z value are in a relationship of proteins with an amino acid that is non-isotope labeled, and the same amino acid that is isotope labeled.

Mass chromatograms at the first and second m/z values determined in this way are obtained via a data input/output unit, from a mass analysis database of the memory unit 100, or the mass spectroscopic device 20, in the processing unit. The obtained mass chromatograms at the first and second m/z values are processed by waveform separation in the processing unit, as described in step S115 of FIG. 5 or in step S206 of FIG. 10. Such waveform separation processing allows data observed at first sight as a single protein peak only from the result of a mass chromatogram at an m/z value to be separated into mass chromatograms derived from specific proteins (see FIG. 8).

Next, the data separated into mass chromatograms derived from specific proteins are sent from the waveform processing unit to the computation unit, calculation of the areas of waveforms separated in the computation unit, and calculation of a ratio of the areas of waveforms between mass chromatograms derived from corresponding specific proteins in non-isotope labeled and isotope labeled proteins are executed.

Thus, according to the analysis method pertaining to the present invention, a quantitative analysis is enabled by comparison between waveform separated mass chromatograms derived from specific proteins, in proteins containing non-isotope labeled and isotope labeled amino acids.

Next, an analysis method using an internal standard substance that is a metabolically isotope labeled protein or a cell containing an internal standard substance that is a metabolically isotope labeled protein will be explained.

As explained in the first embodiment of the present invention, the internal standard substance that is the metabolically isotope labeled protein or the cell containing the internal standard substance that is the metabolically isotope labeled protein is added beforehand to each sample, protein from each sample is extracted, fractionated and the like, and measured with a mass spectroscopic device. Then, by carrying out the analysis method according to the present invention, which involves waveform separation processing, as described in FIG. 5, and FIG. 9 to FIG. 11, quantitative analysis of a biological molecule is possible. Note that such analysis method is useful when a sample cannot be cultured, and even when a sample can be cultured, in cases where there is an influence by passage culture, and in cases where samples cannot be prepared at the same time in the same laboratory. In addition, if a protein in the internal standard substance is in a known quantity, absolute quantitation is possible.

Figure 12:
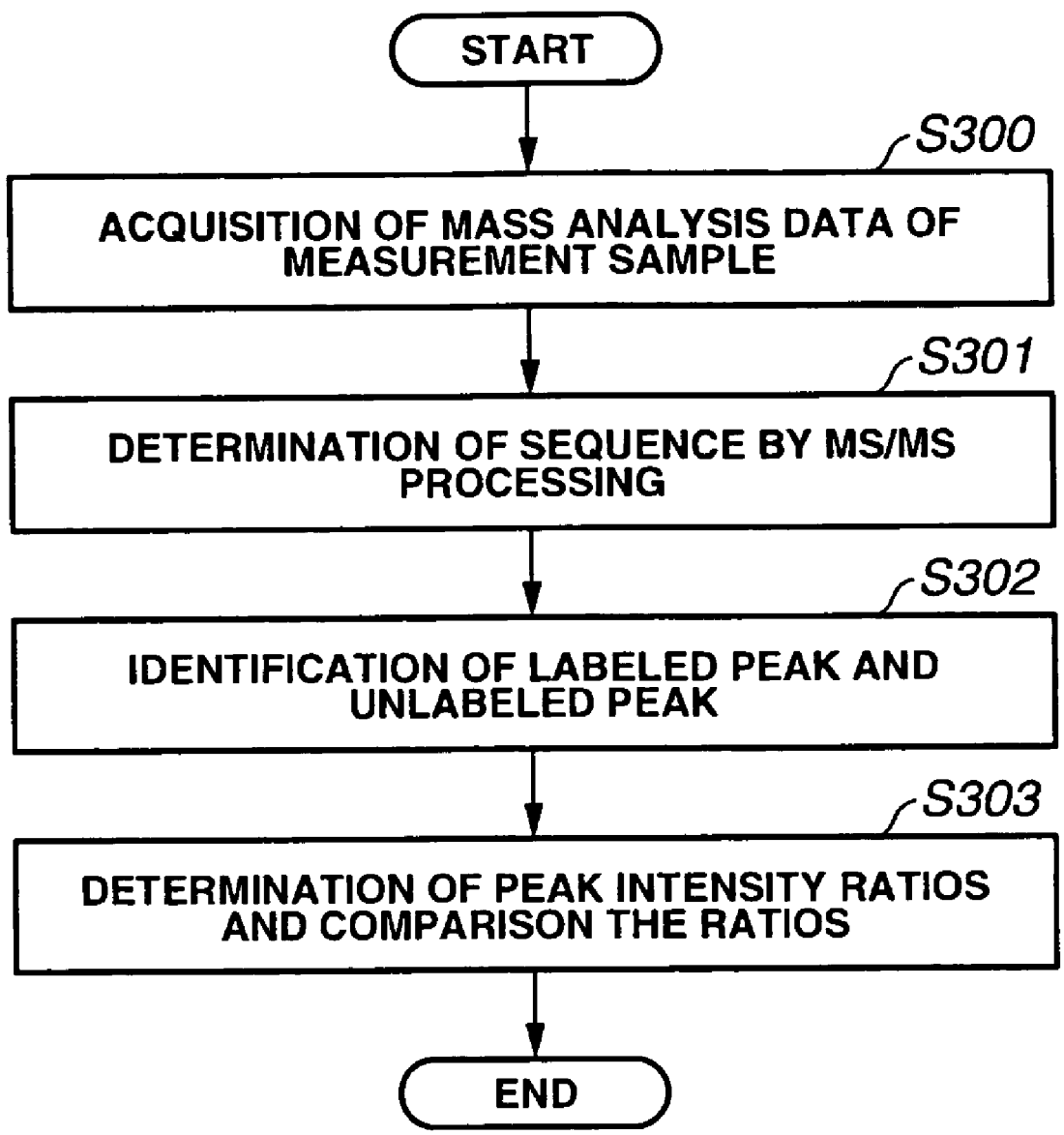
FIG. 12 shows a flowchart of a program for performing a method in the first embodiment according to the present invention.

Here, a program for executing the method for determining and comparing ratios of intensities between the labeled peak and the unlabeled peak of the biological molecule in the first embodiment of the present invention, will be described. FIG. 12 shows a flowchart of the program for determining and comparing ratios of intensities in the first embodiment of the present invention. In step S300 shown in FIG. 12, mass analysis data of various measurement samples measured in the mass spectroscopic device 20 are acquired in the analysis device unit 30 of the analysis system 10 according to the present invention. The measurement samples may contain a fractionated sample, a purified sample, a separated sample, a digested sample or a sample separated by HPLC, as described above. Here, in particular, biological molecules that are not metabolically isotope labeled, and non-isotope labeled biological molecules are the subjects of the measurement.

Next, in step S301, while retrieving data related to the measurement result of the mass spectra with the external database, for example, the NCBInr database, via a communication control IF unit 70 of the analysis device unit 30, the data related to the mass analysis obtained by MS/MS processing, specifically, identification of isotope labeled and non-isotope labeled proteins, in other words, an amino acid sequence is determined in the processing unit of the control unit 60. Thereafter, the isotope labeled peak and the non-isotope labeled peak to be analyzed are specified (see step S302).

Based on the above result, as shown in step S303, a ratio of peak intensities between the isotope labeled peak and the non-isotope labeled peak in a molecule for which an amino acid sequence of a peptide has been identified is calculated in the control unit 60. By executing the above operation for a plurality of peptides obtained from each sample, ratios of peak intensities can be compared among different peptides.

Moreover, when the isotope labeled biological molecule is in known quantity, if the steps shown in FIG. 12 are executed, the present invention provides a program for quantitating absolutely a biological molecule.

Meanwhile, regarding the waveform separated mass chromatogram, the mass chromatogram that has been actually measured and waveform separated originally is obtained by mass analyzing a protein from which a sample to be analyzed has been separated by two-dimensional electrophoresis or the like. During preparation of this sample, a protein spot band on the gel is cut out and recovered into a container. The gel inside the container is then digested with an enzyme such as trypsin to recover digested peptide fragments, so as to carry out mass analysis.

The peptides recovered in this way derive from the band derived from a protein spot that has been cut-out, but the band per se does not contain a single protein, and even for a same protein, since a peptide may be cut in a sample processing step, it is usual for the same protein to be present in a plurality of bands. Therefore, even if a mass chromatogram has been waveform separated as described above, the same peptide may be measured as a plurality of waveform separated mass chromatograms. Thus, even if the peptide is the same, the value of the ratio (peak of the non-isotope labeled peptide)/(the peak of the isotope labeled peptide) or the ratio (the area of waveform of the non-isotope labeled peptide)/(the area of waveform of the isotope labeled peptide) (hereinafter, these are collectively designated "quantitative value") is different for each peak that has been subjected to mass analysis, thereby leading to the existence of a plurality of values.

In view of the above, from the result of waveform separated mass chromatograms, focusing on one or a plurality of peptides, it can be examined whether or not a protein constituted by the peptides is identified. For example, information on the function of a protein can be obtained by retrieving the result of the mass spectra with the database having information on the function of proteins, such as LocusLink. Here, in LocusLink, link information from a key information in a plurality of databases such as NCBInr, IPI and Sport, to a common key called "Locus ID", and information on the function of proteins are provided. Thus, from a peptide sequence, using a database such as NCBInr, IPI and Sport, a key information can be obtained in each database. Next, using LocusLink, a Locus ID can be obtained from the key information. Then, information on the function of the protein can be obtained from the Locus ID. For instance, from the peptide sequence, using a database such as NCBInr, a key information designated by "GiNo" can be obtained. Next, using LocusLink, a Locus ID is obtained from the GiNo. Then, information on the function of the protein can be obtained from the Locus ID.

Figure 13:
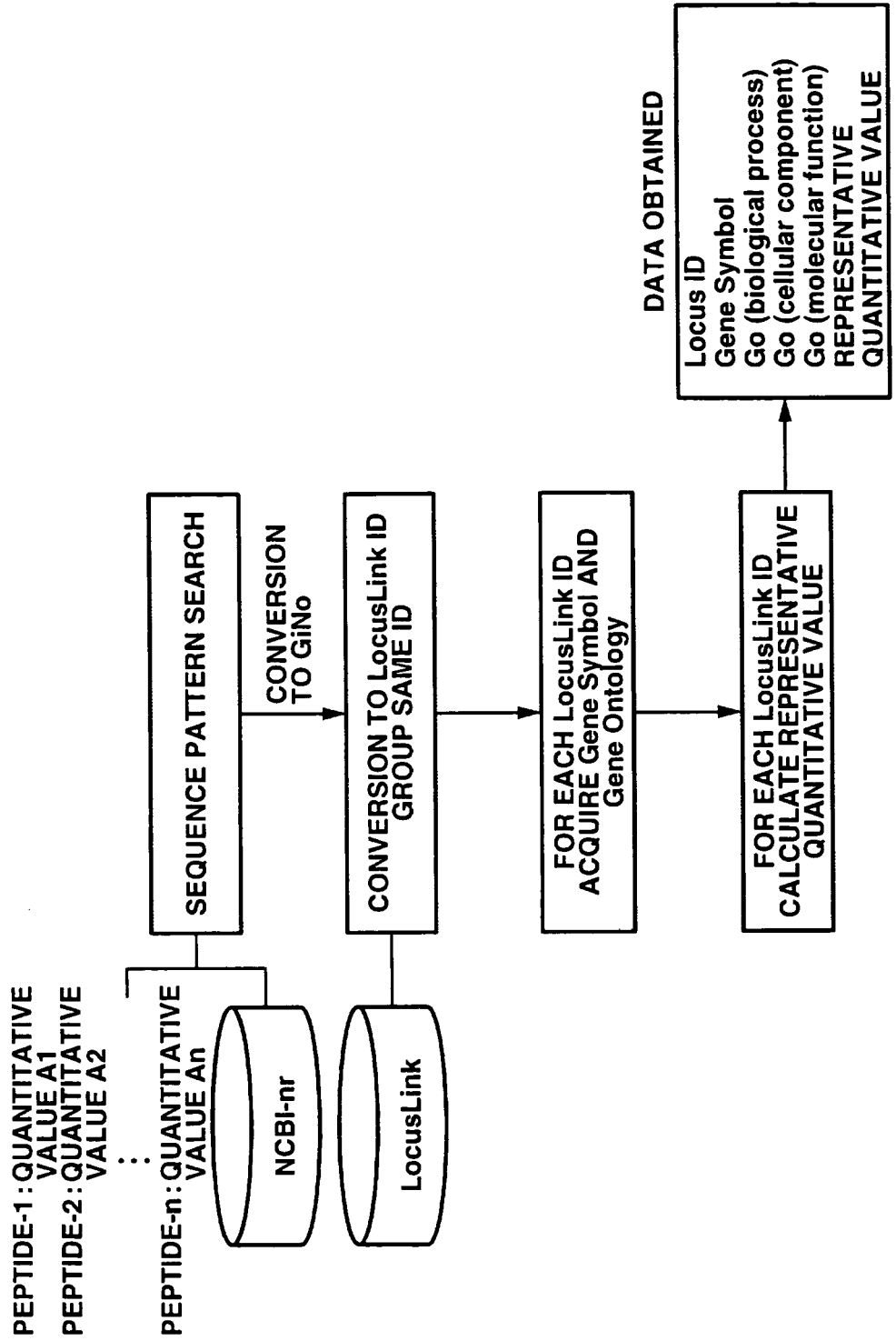
FIG. 13 shows a scheme related to the acquisition of functional information using an external database which is used in the present invention.

FIG. 13 shows a scheme related to the acquisition of functional information using an external database in the present invention. As shown in FIG. 13, once classification by peptide that underwent waveform separation has been performed, databases having information on the function of proteins, for example, such as NCBInr, IPI and Sport, are accessed. In particular, a sequence pattern is verified using NCBI-BLAST. A GiNo, which is a key information of NCBInr, is acquired from the obtained sequence pattern, connection is performed to LocusLink, which is a database having detailed functional information, and a Locus ID is acquired from the GiNo. Thereafter, those with the same Locus ID are grouped, and, from the ID, information of Gene Symbol, Gene Ontology (biological process), Gene Ontology (cellular component), Gene Ontology (molecular function) and representative quantitative value can be obtained. Note that the step prior to waveform separation, is similar to the step shown in FIG. 5 and FIG. 10.

In addition, information on a protein that was constituted by each peptide can also be acquired from the above grouped Gene Symbol, and calculation of a quantitative value of a protein from measurement values of a plurality of peptides becomes possible. This realizes the linking of the quantitative value with biological information of the protein. Note that in the case of the quantitative value of the peptide, although it is possible to calculate simply the average quantitative value thereof, in this case, it is prone to influences from the maximum value and the minimum value of the quantitative value of the peptide. On the other hand, when calculating the quantitative value of the protein, if a standard deviation is determined in the grouped function protein, and the average is determined again with data within the limits of this standard deviation to serve as the quantitative value of this protein, the relationship becomes significant between the quantitative value of the protein, rather than the quantitative value of peptide, and biological information thereof.

The operation for adding the quantitative value and the functional information can be carried out by the information addition unit shown in FIG. 11 using the external database. Note that the process related to the mass analysis data is through the means shown in FIG. 9 and the like, and is similar to information processing step until waveform separation.

Figure 14:
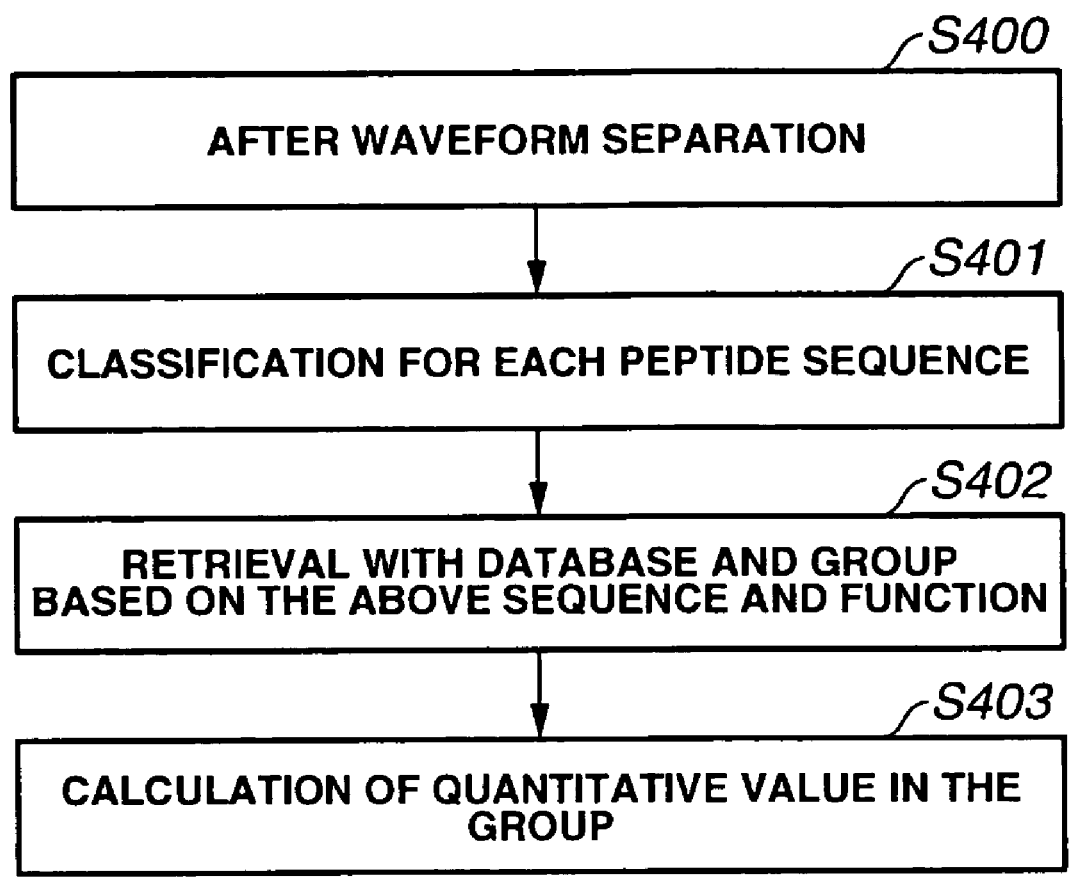
FIG. 14 shows a flowchart for performing method for carrying out addition of functional information, based on the result of mass chromatogram of peptide after waveform separation according to the present invention.

FIG. 14 shows a flowchart for executing, after waveform separation (step S400), a method for carrying out addition of functional information based on the result of the sequence of the peptide determined, in the present invention. In step S401, classification is carried out by sequences of the peptides selected, and the peptide sequence to be analyzed subsequently is specified. Then, as shown in FIG. 9, the external database is accessed via the communication control interface, to acquire functional information. Here, concrete examples of the external database include databases such as NCBInr (http://www.ncbi.nlm.nih.gov/), IPI and Sport and the like. A sequence pattern is then searched from such databases, and information such as a GiNo is acquired. Thereafter, in step S402, from information such as a GiNo of the peptide, the presence or the absence of information regarding the protein that was constituted by the peptide is examined. If protein information is present, the protein is grouped as sequences sharing the information. The quantitative value for this grouped protein is calculated (see step S403). In addition, for this information, as shown in FIG. 14, functional information such as Gene Symbol, GO (biological process), GO (cellular component) GO (molecular function) can also be obtained. Note that determination of the mean value of the above quantitative value and calculation of the representative quantitative value of the peptide can be carried out in the computation unit of the control unit 60 shown in FIG. 9 and FIG. 11.

In this way, from the result of the sequence of the peptide determined, the protein that was constituted by the peptide can be detected, and the quantitative value of this protein can be linked with functional information, specifically, to the Gene Ontology information. This is to suggest a relationship between a quantitative value of the protein and biological data.

In addition, in the present invention it is also possible, after determination of the amino acid sequence constituting the peptide from the mass spectra obtained from MS/MS processing, and without performing waveform separation processing, to access the database having information on the function of the above protein (such as NCBInr) and find the relationship between the quantitative value of the peptide and the biological data. This is also applicable when the mass spectra per se of the peptide for which an amino acid sequence has been determined does not require waveform separation.

Figure 15:
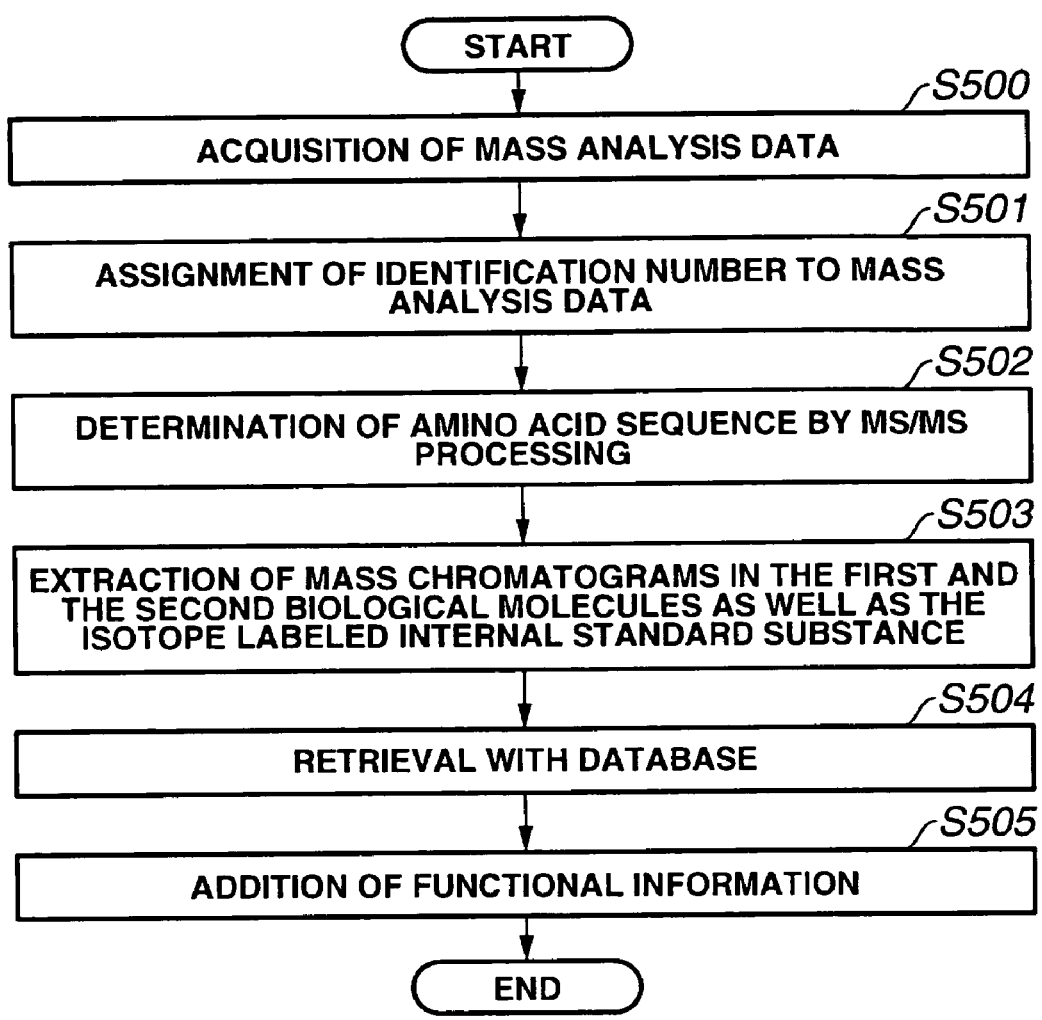
FIG. 15 shows a flowchart for performing a method for carrying out addition of functional information, without performing waveform separation, based on the result of a mass spectrum of a peptide.

FIG. 15 shows a flowchart for executing a method for carrying out addition of functional information, without performing waveform separation, based on the result of mass spectra of the peptide in the presence of an internal standard substance, which is an isotope labeled biological molecule, specifically, based on the result of an amino sequence. As up to steps S500 to S502 shown in FIG. 15, the process is common to steps S200 to S205 shown in FIG. 10, the description will be omitted. In a preferred aspect of the present invention, a mass chromatogram is extracted at the first and the second m/z, as well as at the m/z value of the internal standard substance, in step S503. After step S502, in step S504, the external database is accessed via the communication control interface shown in FIG. 9 in order to acquire functional information. As described above, examples of the external database include databases such as NCBInr (http://www.ncbi.nlm.nih.gov/), IPI and Sport. A sequence pattern of a peptide is searched from such databases, and information such as a GiNo is acquired. Thereafter, in Step 505, from information such as the GiNo of a peptide, the presence of absence of information regarding the protein that was constituted by the peptide is searched, and if a protein information is present, from this protein information, linking is possible with functional information such as Gene Symbol, GO (biological process), GO (cellular component), GO (molecular function) and representative quantitative value. Note that it is not indicated in the flowchart shown in FIG. 15 that the step for determining the ratio of the areas of waveforms of non-isotope labeled peptide and isotope labeled peptide, which is executed in step S209 of FIG. 10. However, it is also possible to determine, in the isotope labeled and non-isotope labeled peptides sequenced in step S502, the area of the waveform of each peptide, calculate the ratio (the area of waveform of non-isotope labeled peptide)/(the area of waveform of isotope labeled peptide), and execute the steps S504 and S505, for linking with functional information. Note that linking with functional information is also similarly possible, using not only the ratio of the areas of waveforms, but also the peak intensity ratio.

EXAMPLE

In the following, the present invention will be illustrated using specific examples; however, the present invention is not limited to these.

Example 1

The following operations were carried out to prepare a cell containing an internal standard substance that was a metabolically isotope labeled biological molecule.

Mouse neuroblastoma Neuro2A was cultured. RPMI-1640 (Sigma, R-7130) containing 10% fetal bovine serum (MOREGATE, BATCH 32300102), 100 U/ml of penicillin G and 100 μg/ml of streptomycin (GIBCO, 15140-122) was used as a culture medium. As RPMI-1640, a powder culture medium not containing L-glutamine, L-lysine, L-methionine, L-leucine and sodium hydrogencarbonate was selected, and components missing from the culture medium were added (L-glutamine (G-8540 manufactured by Sigma), L-lysine (L-9037 manufactured by Sigma), L-methionine (M-5308 manufactured by Sigma) and sodium bicarbonate (Wako Pure Chemical Industries, 191-01305) were added in the amounts of 0.3 g/L, 0.04 g/L, 0.015 g/L and 2 g/L respectively. In addition, 0.05 g/L of L-leucine labeled with a stable isotope (Cambridge Isotope Laboratories, CLM-2262) was added) for preparation. Using the culture medium prepared in this way, a culture was carried out under 5% $CO_2$ at 37° C. The cell which was obtained by this culture was used as a cell containing an internal standard substance that was a metabolically isotope labeled biological molecule in the experiment below (Example 2-7).

The following operation was carried out to measure an amount of a protein in a cell containing an internal standard substance that was a metabolically isotope labeled biological molecule.

A quantity of $1.9 \times 10^7$ cells containing an internal standard substance that was a metabolically isotope labeled biological molecule was solubilized with 1 mL of cell lysis solution M-PER (PIERCE, 78501), and the insoluble fraction was eliminated by centrifugal separation to prepare a soluble fraction. An amount of a protein contained in this soluble fraction was quantitated using the protein quantitation reagent Micro BCA (PIERCE, 23235). As a result, the amount was 6.2 mg/mL.

Example 2

The following experiment was carried out to confirm reproducibility.

<Preparation of Measurement Sample>

A plurality of wild type mice (C57BL/6) and mice from which the ADAM22 gene which was deleted were prepared as samples, and respective whole brains were removed and cryopreserved. In order to measure an amount of a protein per wet weight of brain, the wet weight of one brain among these was measured, furthermore, the brain was homogenized in 10 mM HEPES-(pH 7.4)-1 mM DTT-1 mM $MgCl_2$-1 mM NaF-1 mM vanadate containing protease inhibitors (Complete™ (Roche Diagnostics Co., LTD., product number 1 697 498) dissolved so as to have two tablets per 50 mL of extract from a sample), and a soluble fraction was prepared by a centrifugal separation at 100,000×g for one hour. When an amount of a protein in this soluble fraction was measured, the amount of protein was 39.4 mg per gram of brain wet weight.

A brain to serve as a test sample was thawed, the brain wet weight was measured, and the amount of protein in the test sample was extrapolated from the above amount of protein per brain wet weight. Then, cells containing the internal standard substance that was the metabolically isotope labeled biological molecule obtained in Example 1 worth a cell number ($12.1 \times 10^7$) that gives an equal amount of protein were added, the mixture was homogenized with a Teflon® homogenizer, and non-disrupted cells, nuclei and the like were removed by centrifugal separation at 500×g for 5 minutes. Next, the supernatant thereof was centrifuged at 100,000×g for one hour to prepare a soluble fraction.

<Extraction, Fractionation, Purification and Digestion of the Sample>

In order to confirm that a protein present in a sample can be quantitated, the following operation was carried out using an affinity matrix (Anal. Chem. 75, 2159-2165, 2003) with immobilized E7070, which is known to have affinity for cytosolic malate dehydrogenase (cMDH) (J. Med. Chem. 42, 3789-99, 1999). A quantity of 0.1 mL of soluble fraction was diluted with 0.9 mL of PBS, mixed and reacted with 0.1 mL of affinity matrix with immobilized E7070, the supernatant was then eliminated by centrifugal separation. The precipitated affinity matrix was washed with PBS and 1M NaCl, then the adsorbed protein was eluted with PBS-10 mM NADH solution (NADH was Sigma, N-8129) to recover cMDH. The recovered fraction was concentrated by ultrafiltration, subjected to SDS PAGE (e-PAGEL, E-T520L, manufactured by ATTO) for purification, a band corresponding to cMDH was cut out, and in-gel digestion (Rapid Comm Mass Spectrom., 15, 1416-1421, 2001: Rapid Comm Mass Spectrom., 17, 1071-1078, 2003) was carried out with trypsin (Cat. No. V5111, manufactured by Promega) to obtain a digested sample.

<Measurement of Digested Sample>

The digested sample was measured by MALDI-MS (ABI4700, manufactured by Applied Biosystems: alpha-cyano-4-hydroxyl cinnamic acid (CHCA) as the matrix, co-crystallized with the sample by the Dry-droplet method). Based on the obtained result, fragment identification, calculation of peak intensity ratio (peak areas were calculated to calculate the intensity ratio, with the accompanying software) were performed. The concrete calculation was carried out as follows.

By dividing an unlabeled peak derived from cMDH in a wild type mouse (for instance, when m/z=1750, unlabeled peak=12405.31) with a labeled peak derived from cMDH in an internal standard substance (when m/z=1762 (the molecular weight increases by 12 since two leucines are contained), labeled peak=5373.19), the unlabeled peak/the labeled peak in cMDH (12405.31/5373.19=2.308743) was determined, for cMDH in wild type mouse (Wild) and ADAM22 gene knock out mouse (KO). Next, similarly, by dividing an unlabeled peak derived from cMDH in a wild type mouse (for instance, when m/z=1770, unlabeled peak=4533.977) with a labeled peak derived from cMDH in an internal standard substance (when m/z=1776 (the molecular weight increases by 6 since one leucine is contained), labeled peak=3156.617), the unlabeled peak/the labeled peak in cMDH (4533.977/3156.617=1.436341) was determined. In addition, similarly, for the unlabeled peaks derived from cMDH in a wild type mouse with m/z=1392 and 1039, the ratio of the unlabeled peak/the labeled peak was determined in the same way, and calculated to be 2.435703 and 1.750933 respectively. Next, the mean value 1.98293 of these respective peak intensity ratios 2.308743, 1.436341, 2.435703, 1.750933 was determined, which served as the peak intensity ratio derived from cMDH in a wild type mouse.

On the other hand, by dividing an unlabeled peak of cMDH in ADAM22 gene knock out mouse (unlabeled peak=13011.03) with a labeled peak derived from cMDH in an internal standard substance (labeled peak=6035.838), the unlabeled peak/the labeled peak in the biological molecule (13011.03/6035.838=2.155629) was determined. Similarly, the ratio of the unlabeled peak/the labeled peak were determined, and calculated to be 2.056147, 2.340332 and 2.090195, respectively. Then, the mean value 2.160576 of these respective peak intensity ratios 2.155629, 2.056147, 2.340332, and 2.090195 was determined, which served as the peak intensity ratio derived from cMDH in a ADAM22 gene deficient mouse.

Next, peak intensity ratio in wild type mouse (2.308743) and peak intensity ratio in ADAM22 gene knock out mouse (2.160576) were compared to obtain the ratio 0.917778.

Figure 16:
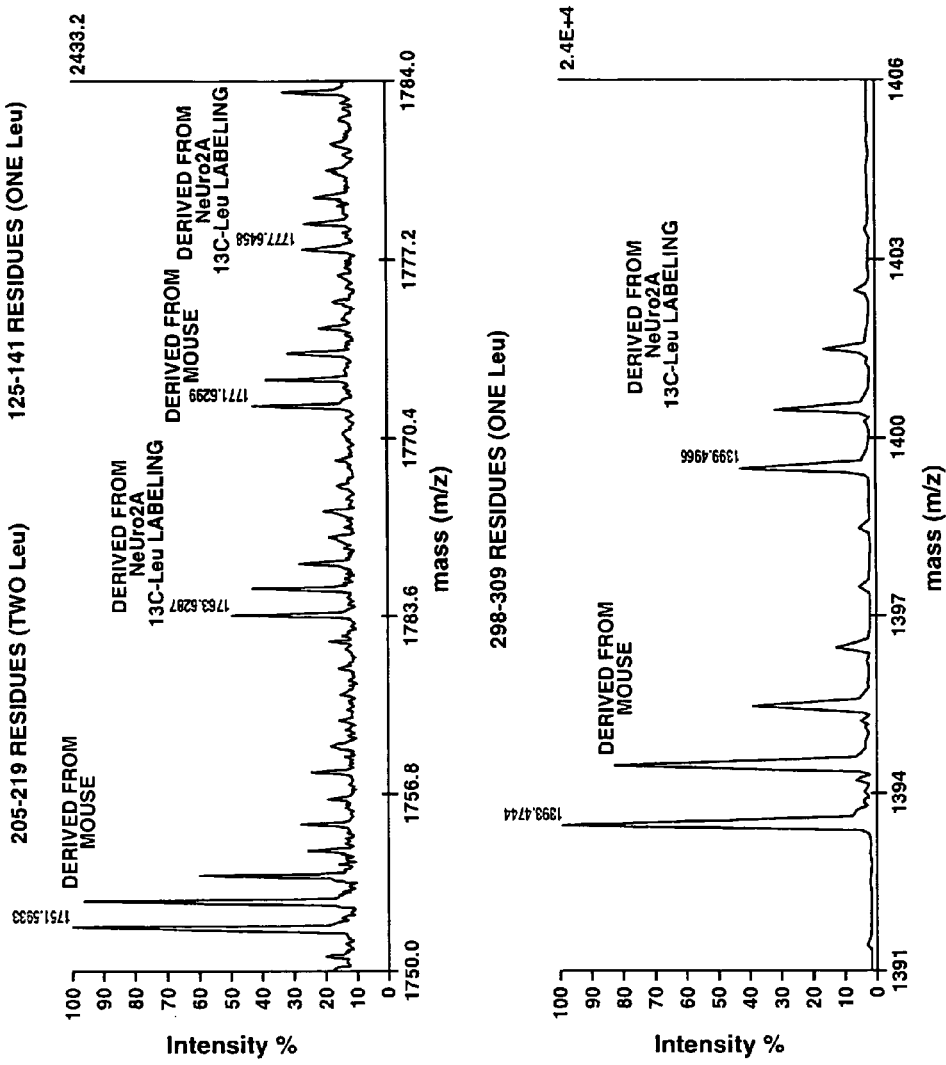
FIG. 16 shows mass spectra derived from a wild type mouse brain and derived from an internal standard substance that is a metabolically isotope labeled biological molecule, for cMDH.

This operation was repeated five times, and the variation in the measurement values among experiments was examined. As a result, regardless of going through a step of affinity purification in which the variation of measurement value among experiments is large, a result with good reproducibility could be obtained, with a CV value of 4.1%. (FIG. 16 and Table 1)

TABLE 1

| Wild mass | Area(L) | Area(H) | Ratio(L/H) | K/O mass | Area(L) | Area(H) | Ratio(L/H) | Ratio(W/k) |
|---|---|---|---|---|---|---|---|---|
| 1750 | 12405.31 | 5373.19 | 2.308743 | 1750 | 1301103 | 6035.838 | 2.155629 | |
| 1770 | 4533.977 | 3156617 | 1.436341 | 1770 | 3705.164 | 1801.993 | 2.056147 | |
| 1392 | 138421.1 | 56830.04 | 2.435703 | 1392 | 1502735 | 64210.36 | 2.340332 | |
| 1039 | 28555.8 | 16308.91 | 1.750933 | 1039 | 24660.15 | 11798.01 | 2.090195 | |

TABLE 1-continued

| Wild mass | Area(L) | Area(H) | Ratio(L/H) | K/O mass | Area(L) | Area(H) | Ratio(L/H) | Ratio(W/k) |
|---|---|---|---|---|---|---|---|---|
| | | Average | 1.98293 | | | Average | 2.160576 | 0.917778 |
| 1750 | 13551 | 5744332 | 2.359022 | 1750 | 2395493 | 9910.511 | 2.417124 | |
| 1770 | 5397.259 | 2702.94 | 1.996811 | 1770 | 9646849 | 5032.268 | 1.916998 | |
| 1392 | 147268.9 | 61704.06 | 2.386697 | 1392 | 2817336 | 114592.9 | 2.458561 | |
| 1039 | 26854.76 | 13698.29 | 1.961161 | 1039 | 5694268 | 25618.81 | 2.22269 | |
| | | Average | 2.175923 | | | Average | 2.253843 | 0.965428 |
| 1750 | 11257.72 | 5114787 | 2.201015 | 1750 | 1510669 | 6867.176 | 2.19984 | |
| 1770 | 5187.533 | 3096606 | 1.675232 | 1770 | 4214857 | 2928.235 | 1.439385 | |
| 1392 | 148330.8 | 65778.05 | 2.255019 | 1392 | 2562836 | 102502.1 | 2.500276 | |
| 1039 | 24789.65 | 15605.92 | 1.588478 | 1039 | 3310672 | 18069.98 | 1.83214 | |
| | | Average | 1.929936 | | | Average | 1.99291 | 0.968401 |
| 1750 | 14410.3 | 6681.478 | 2.156753 | 1750 | 1245894 | 5465.123 | 2.279717 | |
| 1770 | 5477.694 | 3650.52 | 1.500524 | 1770 | 5134186 | 3409.58 | 1.505812 | |
| 1392 | 155057.6 | 63450.08 | 2.443773 | 1392 | 194511 | 83196.93 | 2.337968 | |
| 1039 | 30016.37 | 20676.58 | 1.451709 | 1039 | 31857.73 | 15395.36 | 2.069307 | |
| | | Average | 1.88819 | | | Average | 2.048199 | 0.921878 |
| 1750 | 7476.987 | 2575517 | 2.903102 | 1750 | 919284 | 3680.458 | 2.497744 | |
| 1770 | 2126.221 | 1691176 | 1.257244 | 1770 | | | | |
| 1392 | 66495.31 | 28199.55 | 2.358027 | 1392 | 1342732 | 53852.04 | 2.493373 | |
| 1039 | 12364.09 | 8749955 | 1.413046 | 1039 | 1274557 | 7087.918 | 1.798211 | |
| | | Average | 1.982855 | | | Average | 2.263109 | 0.876164 |
| | | | | | | | Average | 0.92998 |
| | | | | | | | Stdev | 0.038221 |
| | | | | | | | CV (%) | 4.110099 |

Table 1: Regarding cMDH, reproducibility (n=5) of the peak intensity ratio to the internal standard substance that was the metabolically isotope labeled biological molecule in the wild type mouse brain and the ADAM22 gene deficient mouse brain, as well as comparison of the peak intensity ratio of the wild type mouse brain and the peak intensity ratio of the ADAM22 gene deficient mouse brain with respect to the internal standard substance, is represented.

Example 3

The following experiment was carried out in order to confirm that a ratio of intensities of peaks on mass spectrum varies proportionally according to the variation in amounts of target substance.

<Preparation of Measurement Sample>

A whole brain of a wild type mouse (C57B6) was removed and cryopreserved as a sample. The brain wet weight was measured, the brain was homogenized in 10 mM HEPES-(pH 7.4)-1 mM DTT-1 mM $MgCl_2$-1 mM NaF-1 mM vanadate containing protease inhibitors (Complete™ (Roche Diagnostics Co., LTD., product number 1 697 498) dissolved so as to have two tablets per 50 mL of extract from a sample) and a soluble fraction was prepared by a centrifugal separation at 100,000×g for one hour. Preparation was carried out to obtain 3.7 mg/mL for the protein concentration of the soluble fraction.

A quantity of $1.9 \times 10^7$ cells containing an internal standard substance that was a metabolically isotope labeled biological molecule obtained in Example 1 was solubilized with 1 mL of cell lysis solution M-PER (PIERCE, 78501), and the insoluble fraction was removed by centrifugal separation to prepare the internal standard substance that was the metabolically isotope labeled biological molecule. The internal standard substance that was the metabolically isotope labeled biological molecule was mixed at the proportion of 1:3, 1:1, 3:1 and 10:1 based on the above soluble fraction to serve as soluble fractions of the sample (0.2 mL each).

<Extraction, Fractionation, Purification and Digestion of the Measurement Sample>

In order to confirm that a protein present in a sample can be quantitated, the following operation was carried out using an affinity matrix (Anal. Chem. 75, 2159-2165, 2003) with immobilized E7070, which is known to have affinity for cytosolic malate dehydrogenase (cMDH) (J. Med. Chem. 42, 3789-99, 1999). A quantity of 0.1 mL of soluble fraction was diluted with 0.9 mL of PBS, mixed and reacted with 0.1 mL of affinity matrix with immobilized E7070, the supernatant was then eliminated by centrifugal separation. The precipitated affinity matrix was washed with PBS and 1M NaCl, then the adsorbed protein was eluted with PBS-10 mM NADH solution (NADH was Sigma, N-8129) to recover cMDH. The recovered fraction was concentrated by ultrafiltration, subjected to SDS PAGE (e-PAGEL, E-T520L, manufactured by ATTO) for purification, a band corresponding to cMDH was cut out, and in-gel digestion (Rapid Comm Mass Spectrom., 15, 1416-1421, 2001: Rapid Comm Mass Spectrom., 17, 1071-1078, 2003) was carried out with trypsin (Cat. No. V5111, manufactured by Promega) to obtain a digested sample.

<Measurement of Measurement Sample>

Figure 17:
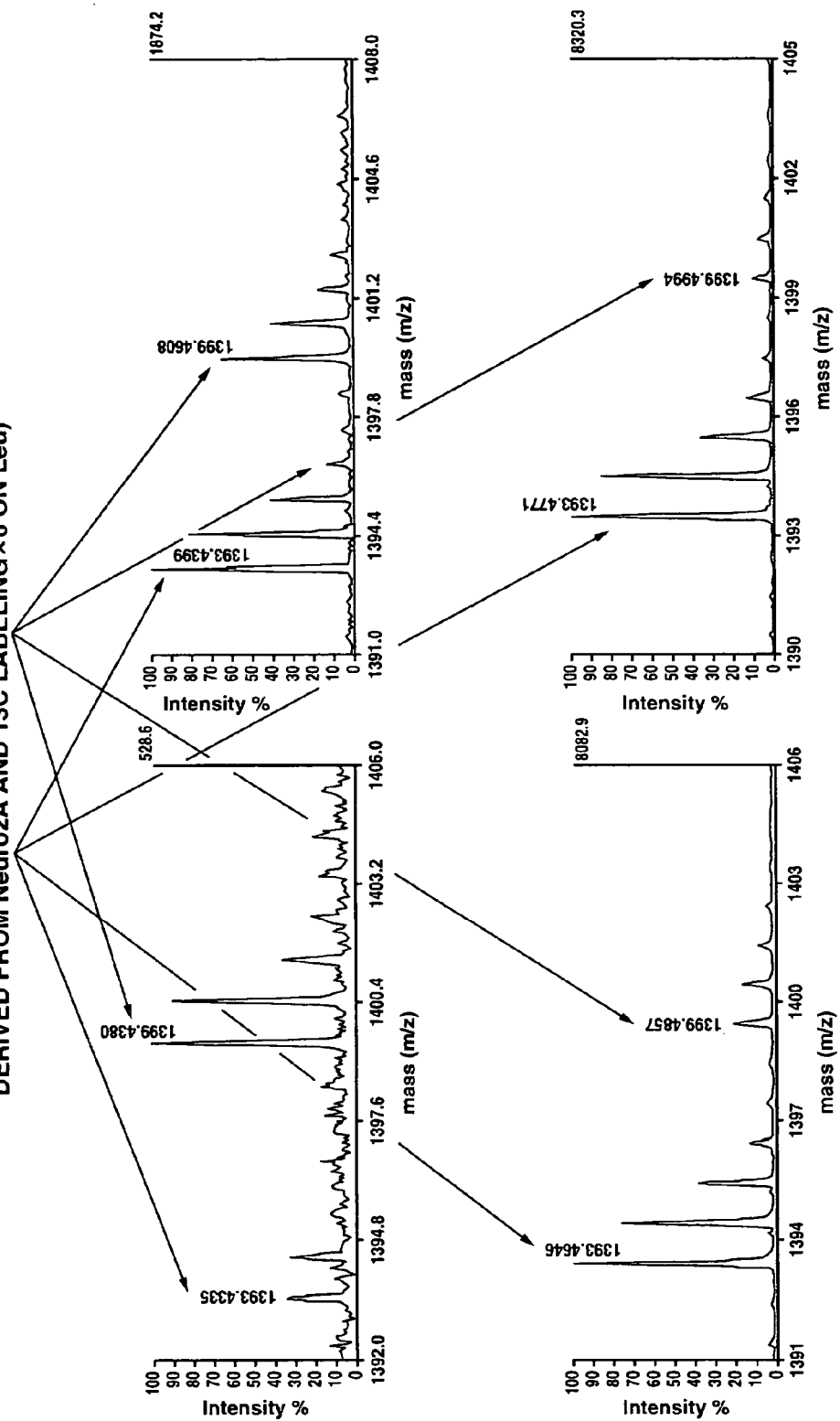
FIG. 17 shows a representation of dose dependency in the ratio of mass spectra derived from a wild type mouse brain and derived from an internal standard substance that is a metabolically isotope labeled biological molecule, for cMDH.
Figure 18:
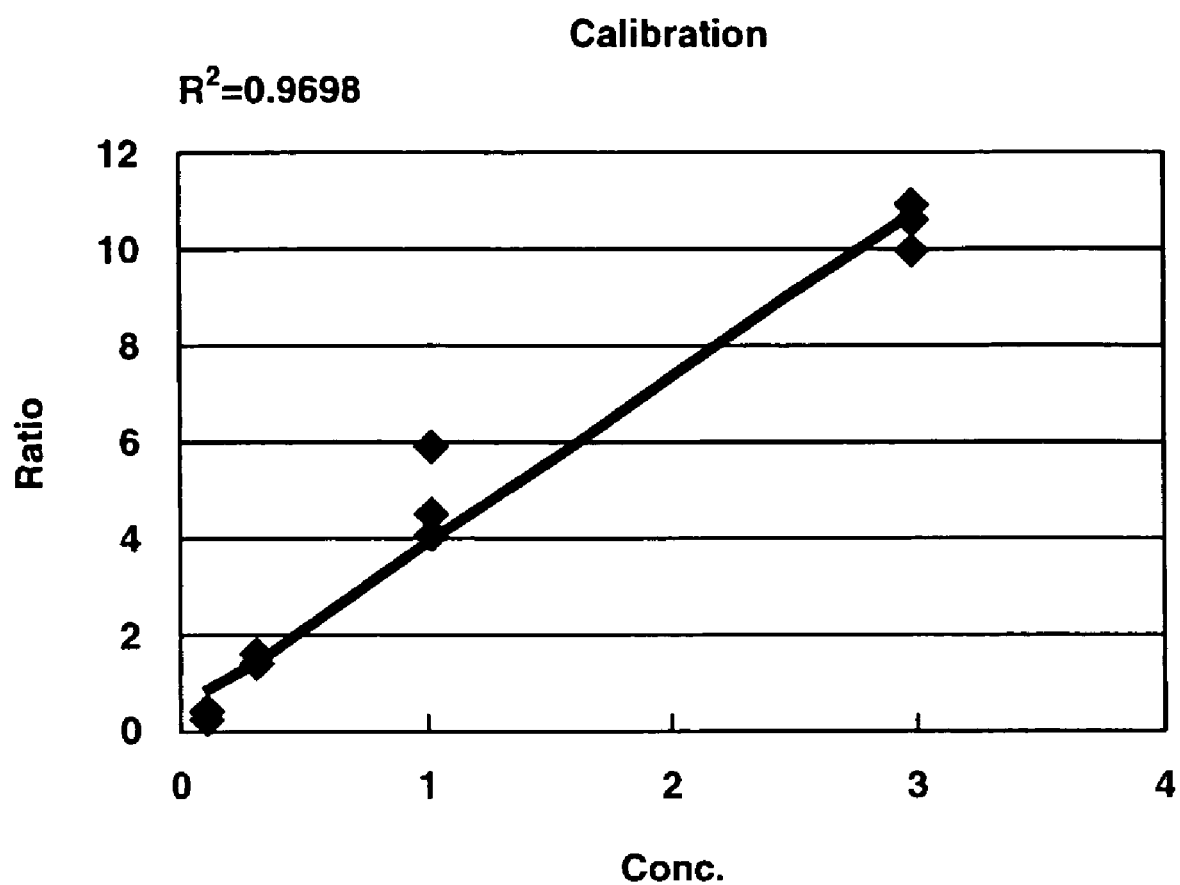
FIG. 18 shows a plot of the theoretical ratio and the actually measured ratio of the expression amount derived from a wild type mouse brain and derived from an internal standard substance that is a metabolically isotope labeled biological molecule by mass analysis, for cMDH.
Figure 19:
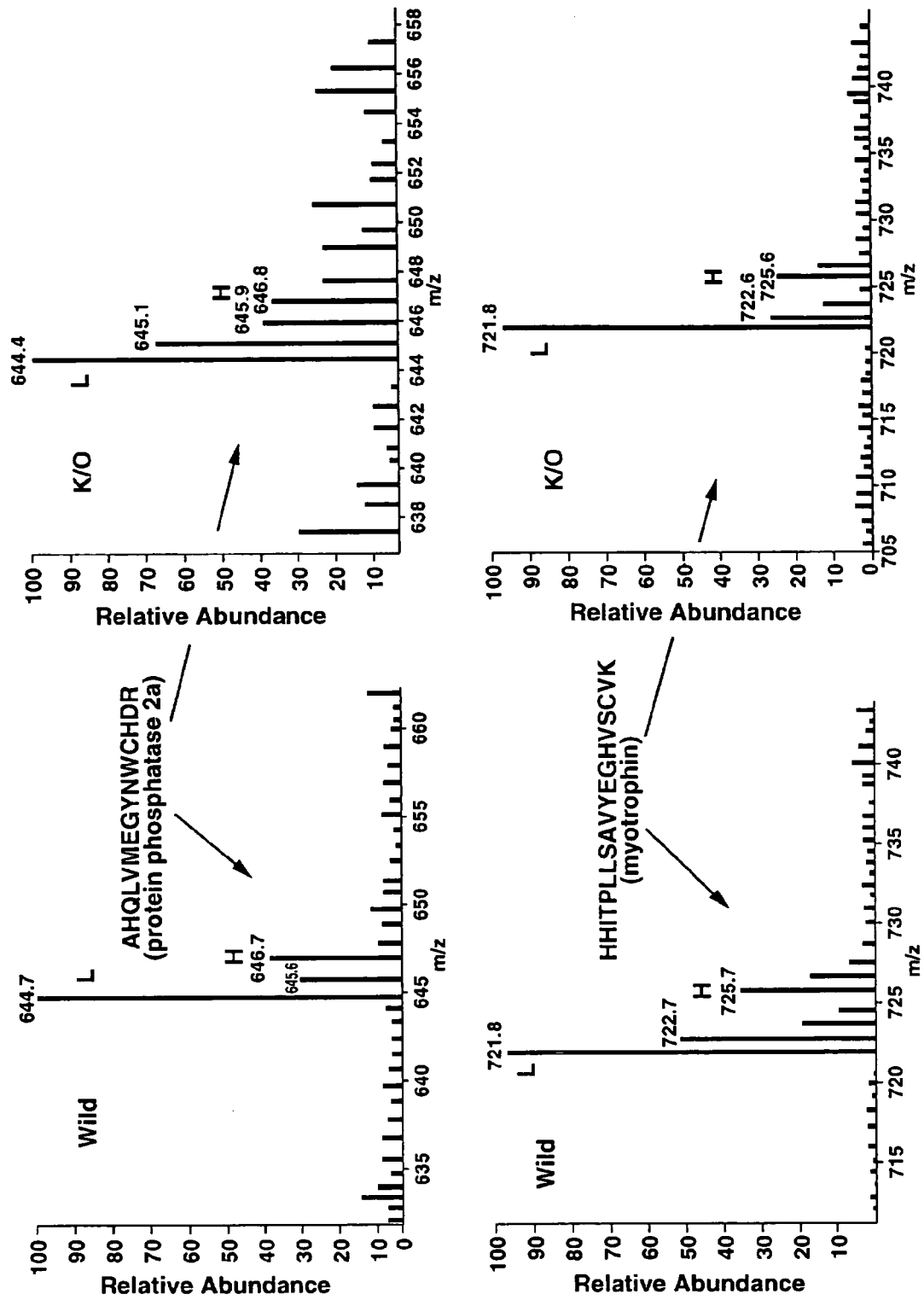
FIG. 19 shows mass spectra (L) derived from a wild type mouse brain (Wild) and (H) derived from an internal standard substance that is a metabolically isotope labeled biological molecule, as well as, mass spectra (L) derived from ADAM22 gene deficient mouse brain (K/O) and (H) derived from an internal standard substance that is a metabolically isotope labeled biological molecule, for protein phosphatase 2a and myotrophin.
Figure 20:
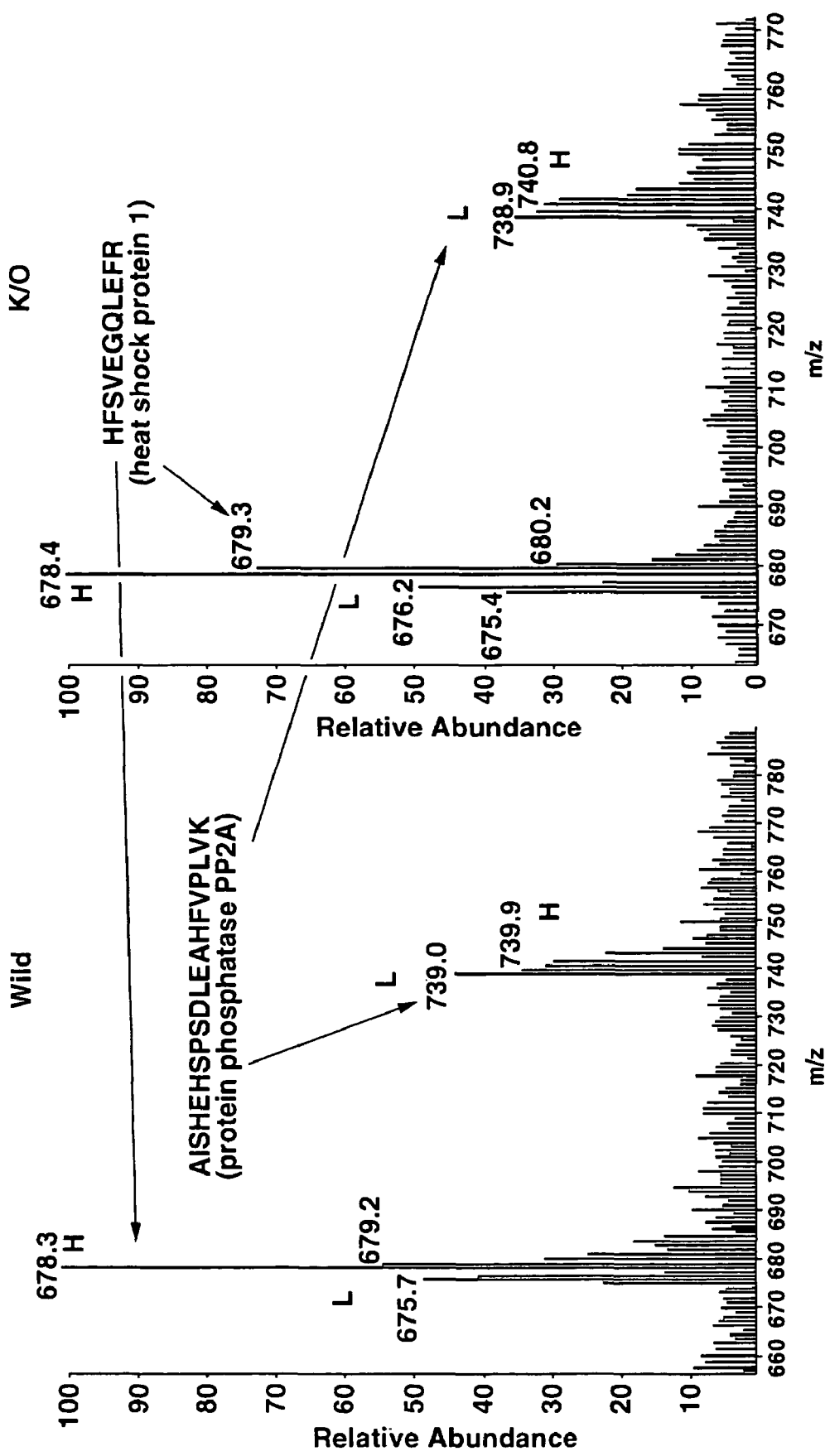
FIG. 20 shows mass spectra (L) derived from a wild type mouse brain (Wild) and (H) derived from an internal standard substance that is a metabolically isotope labeled biological molecule, as well as, mass spectra (L) derived from ADAM22 gene deficient mouse brain (K/O) and (H) derived from an internal standard substance that is a metabolically isotope labeled biological molecule, for protein phosphatase PP2A and heat shock protein 1.
Figure 21:
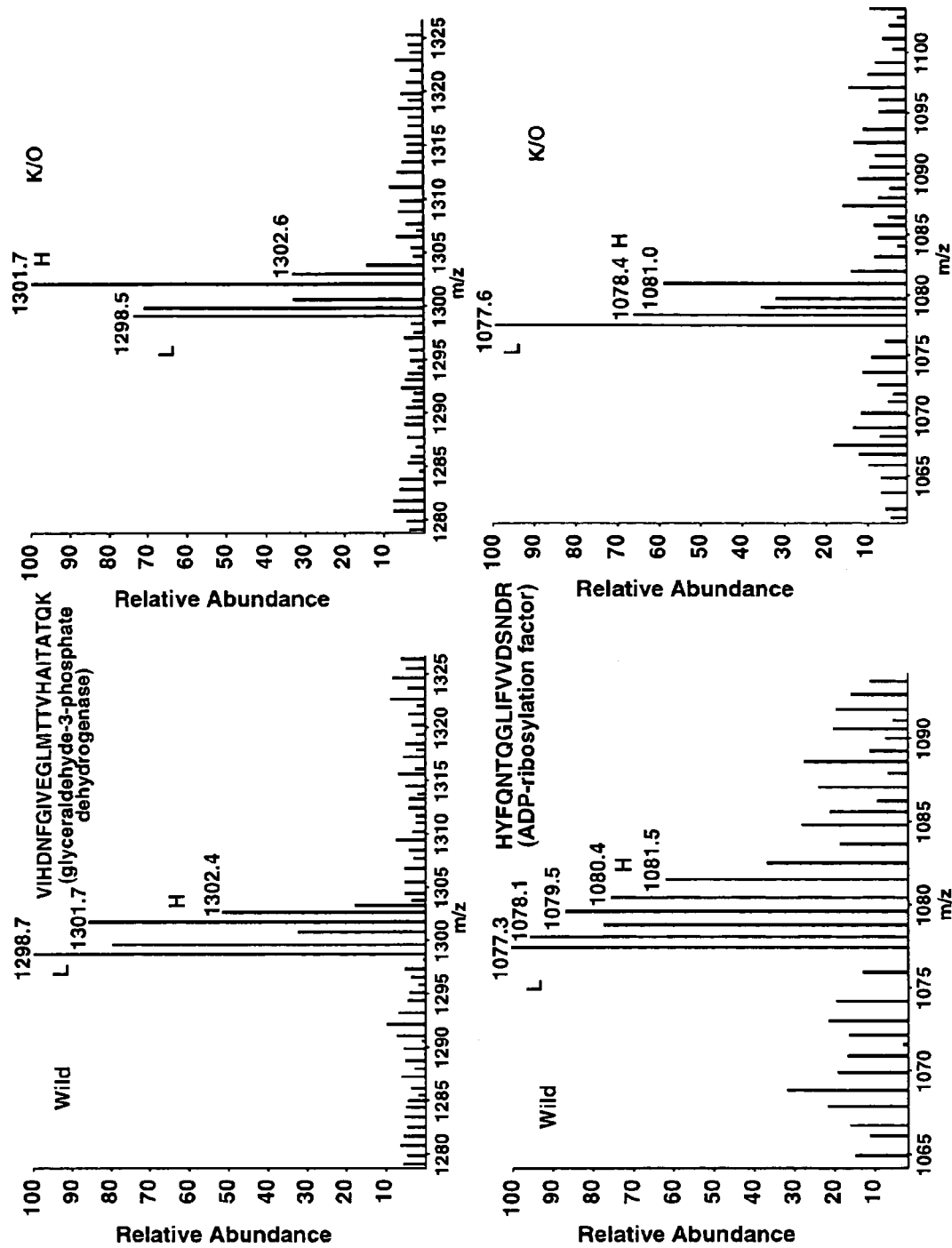
FIG. 21 shows mass spectra (L) derived from a wild type mouse brain (Wild) and (H) derived from an internal standard substance that is a metabolically isotope labeled biological molecule, as well as, mass spectra (L) derived from ADAM22 gene deficient mouse brain (K/O) and (H) derived from an internal standard substance that is a metabolically isotope labeled biological molecule, for glyceraldehyde-3-phosphate dehydrogenase and ADP-ribosylation factor.
Figure 22:
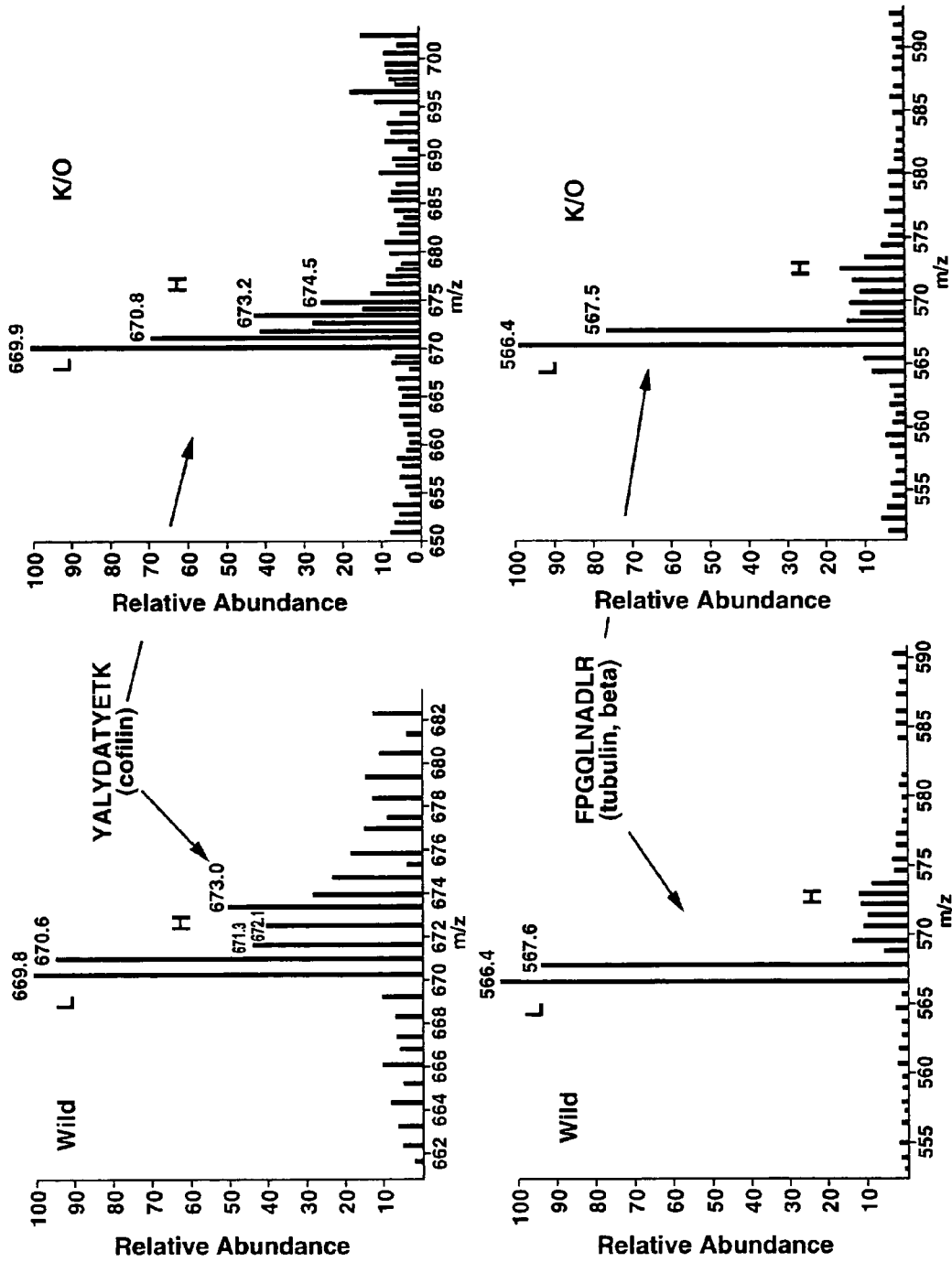
FIG. 22 shows mass spectra (L) derived from a wild type mouse brain (Wild) and (H) derived from an internal standard substance that is a metabolically isotope labeled biological molecule, as well as, mass spectra (L) derived from ADAM22 gene deficient mouse brain (K/O) and (H) derived from an internal standard substance that is a metabolically isotope labeled biological molecule, for cofilin and tubulin-beta.

The digested sample was measured by MALDI-MS (ABI4700, manufactured by Applied Biosystems: alpha-cyano-4-hydroxyl cinnamic acid (CHCA) as the matrix, co-crystallized with the sample by the Dry-droplet method). Based on the obtained result, fragment identification, calculation of peak intensity ratio (peak areas were calculated to calculate the intensity ratio, with the accompanying software) were performed. As a result, the peak intensity ratio was a straight line proportional to the amount of sample quantity ($R^2=0.97$), such that quantitation was possible with an extremely good accuracy (FIGS. 17 and 18).

Example 4

The following experiment was carried out in order to confirm that the present method can be applied to comparison among samples derived from animal tissues.

<Preparation of Measurement Sample>

Preparation was carried out so as to obtain a protein concentration in the soluble fraction of 3.7 mg/mL.

A wild type mouse (C57B6) and mouse with the ADAM22 gene deleted (lineage, breeder) were prepared as samples, the respective whole brains were removed and cryopreserved. Next, a brain was thawed, the brain wet weight was measured, and an amount of a protein in the sample was calculated from the amount of protein per brain wet weight obtained in Example 1. Cells containing an internal standard substance that was a metabolically isotope labeled biological molecule obtained in Example 1 worth a cell number that gives an equal amount of protein were added, the mixture was homogenized with a Teflon®, and non-disrupted cells, nuclei and the like were removed by centrifugal separation at 500×g for 5 minutes. The supernatant thereof was then centrifuged at 100,000×g for one hour to prepare a soluble fraction. When the amount of protein was measured, the protein derived from wild type mouse was 3.02 mg/mL, the protein derived from mouse with the ADAM22 gene deleted was 3.12 mg/mL. These served as fractionated samples.

Next, for each fractionated sample, the following operation was carried out for each 2 mL (for each two 1 mL tubes). Urea (Bio-Rad Cat. No. 161-0731) was added to obtain 8M, and 3 m per 1 mL of dithiothreitol (Wako Pure Chemical Industries Cat. No. 045-08974: DTT) was added to a 0.5M Tris buffer solution (pH 8.3, manufactured by Sigma), 500 μL of which was added to each fractionated sample, and incubation was carried out at 37° C. for 3 hours to reduce cysteine residues in the proteins. Thereafter, urea was added to obtain 8M, 8 mg of acrylamide (Cat. No. 161-0107 manufactured by Bio-Rad) was added to a 0.5M Tris buffer solution (pH 8.3), 500 μL of which was added to each fractionated sample, and incubation was carried out at room temperature for 3 hours to alkylate cysteine residues. An amount of 8 mg of DTT was added therein to inactivate excess acrylamide. Using SnakeSkin with a 10,000 molecular weight cutoff (Pierce, Cat. No. 68100), dialysis was carried out with a 1000-fold volume of 10 mM ammonium hydrogencarbonate buffer solution at 4° C. for one day and night to remove reducing and alkylating reagents, the fractionated samples were separated into two tubes, each of protein derived from wild type mouse and protein derived from mouse with the ADAM22 gene deleted respectively, and lyophilized with a SpeedVac. The each fractionated sample was redissolved with 200 μL of a 0.2% beta octylglucoside aqueous solution containing 8M urea, diluted 5-fold with 50 mM ammonium hydrogencarbonate, to a total of 1 mL. To a quantity of protein of 0.3 mg, 100 μL of trypsin (Cat. No. V5111, manufactured by Promega) was added, and digestion was carried out at 37° C. for 24 hours. The digested sample was obtained here. Each one tube of the each digested sample (protein derived from wild type mouse, protein derived from mouse with the ADAM22 gene deleted) was applied onto an anion exchange column (Mini-Q PC 3.2/3: Amersham Biosciences Cat. No. 17-0686-01) and a cation exchange column (Mini-S PC 3.2/3: Amersham Biosciences Cat. No. 17-0687-01), and fractionation was carried out each minute. In case of the anion exchange column, 50 μL of aqueous ammonia and 0.5 mL of ultra pure water were added to the digested sample, the mixture was centrifuged at 20,000×g for one minute, and the supernatant was injected onto the anion exchange column. On the other hand, in case of the cation exchange column, 50 μL of formic acid and 0.5 mL of ultra pure water were added to the digested sample, the mixture was centrifuged at 20,000×g for one minute, and the supernatant was injected onto the cation exchange column. For the HPLC conditions, flow rate was 0.2 mL per minute, UV detection wavelength was 235 nm & 280 nm, in case of the cation exchange column, the mobile phase A was 5% acetonitrile to 25 mM of formic acid, the mobile phase B was 1M ammonium formate at pH 3.5 and 5% acetonitrile. In the case of anion exchange, the mobile phase A was 25 mM ammoniacal and 5% acetonitrile, mobile phase B was 1M ammonium acetate at pH 8.6 and 5% acetonitrile. For the gradient, the first 5 minutes was 100% mobile phase A, thereafter the mobile phase concentration was linearly increased to 40% over 40 minutes, thereafter the mobile phase B was 100% in 15 minutes and flown for 5 minutes. Each fraction eluted from the column was acidified with the addition of TFA, and applied to ZipTipC18 (Cat. No. ZTC18S960 manufactured by Millipore) which was beforehand washed with acetonitrile then conditioned with 0.1% TFA water. Next, the sample was demineralized by washing three times with 20 μL of 0.1% TFA water containing 5% acetonitrile, and eluting with 5 μL of 0.1% TFA water containing 70% acetonitrile. A sample separated by HLPC was obtained here.

Next, this sample separated by HPLC was diluted with 95 μL of 0.1% TFA water and measured with LC (C18 column)/ MS (ThermoFinnigan LCQ). As the conditions for the above measurement, on the HPLC side, 0.2% acetic acid water containing 5% acetonitrile and 0.01% TFA as the mobile phase A, and 0.2% acetic acid water containing 95% acetonitrile and 0.01% TFA as the mobile phase B were used with a Magic C18 column 0.2×150 mm (Cat. No. 902-61261-00) from Michrom BioResources Inc, the first one minute being 100% mobile phase A, thereafter, mobile phase B was brought linearly to 40% over 35 minutes, then, mobile phase B was brought to 100% in 0.1 minute and maintained for 7 minutes, thereafter mobile phase A was brought to 100% for 14 minutes prior to injecting the following sample. For the device, the ROM from the LC-10A series by Shimadzu Corporation were changed to the micro handler, as the mixing chamber, the accessory chamber manufactured by Shimadzu Corporation was removed and a T-connector from Valco was adopted. As the flow rate, the Flow-splitting method was adopted and the flow rate as adjusted so as to obtain a flow rate of approximately 1-2 μL per minute to the column. With the auto sampler PAL from CTC Corporation, 50 μL of sample was injected, and once the sample was concentrated in the capillary trapping column for peptide (Michrom BioResource, Cat. No. 004-25109-32) embedded in the sample loop of the injector, it was sent to the analytical column. For the mass spectroscopic device, LCQ Duo from ThermoFinnigan was fitted with a low flow rate handling sub-nanosprayer that does not use seath gas and can arbitrarily adjust the spray position with an XYZ stage, which was custom made by AMR, and, for spraying, a metal needle ((catalogue number 7820-59001) manufactured by GL Science) was directly connected to C18 column, and used. As the ESI voltage, 2.6 kV was applied. For the measurement, Repeat of Dynamic Exclusion was set to 1 in the Data Dependent mode. Note that to gain on the number of scans, measurements were performed with the Zoom Scan mode off, in a so-called double-play mode.

Regarding the obtained data, SonarMSMS (Genomic solution) and NCBInr database were used to carry out automatic identification of protein. A portion of the program was altered such that even a leucine labeled with a stable isotope (for each leucine, an increase of 6 in molecular weight) can be searched against NCBInr. As quantitation is carried out with the peak of a peptide containing leucine, among the peptides identified by SonarMSMS, a software was built for automatically calling scan information from LCQ_dta.exe file, which is a software associated with LCQ Duo, to choose only the peptides containing leucine, and, to specify the elution position of this peptide peak (retention time in HPLC=scan number in mass analysis). From this scan number information, a mass spectrum corresponding to this scan number was extracted, for the peak of a natural leucine peptide and the peak of an isotope peptide, parent ion information (m/z value) when MS/MS was measured and how many leucines there were in this peptide, then how many electric charges there were, were determined from the result of the search in SonarMSMS. A peak to be paired was looked for, and the peak intensity ratio thereof was automatically calculated. Using the analysis software according to the present invention established in this way, identification of the protein and calculation of peak intensity ratio were performed. In addition, for a protein that is present in a sample, and, identified by mass analysis and not present in the internal standard substance that is a metabolically isotope labeled biological molecule, a peak intensity ratio with a peptide peak derived from the internal standard substance that is the metabolically isotope labeled biological molecule present at a Scan number that is identical or close to the mass spectrum in which this peptide has been identified, was determined. Next, amounts of protein contained in the soluble fraction between the whole brain of a wild type mouse and the whole brain of a mouse with the ADAM22 gene deleted was calculated by comparing the peak intensity ratios determined previously.

FIG. 19 to FIG. 22 show the result of protein identification obtained in Example 4 according to the present invention. As a result, a plurality of biological molecules (for instance, protein phosphatase 2a, myotrophin, heat shock protein 1, protein phosphatase PP2A, glyceraldehyde-3-phosphate dehydrogenase, ADP-ribosylation factor, cofilin, tubulin-beta, and the like) were identified, and could be relatively quantitated comprehensively as shown below.

FIGS. 23 to 26 show the result for the ratio of the areas of waveforms derived from an individual protein subjected to waveform separation processing according to the present invention, based on the result of protein identification above.

The proteome analysis according to the present invention will be explained taking a protein containing leucin as example. From the mass analysis result of a protein derived from protein phosphatase 2a shown in FIG. 19, the focus was on a peak, the m/z value of which was 644.7, derived from a protein containing non-isotope labeled leucine (indicated by L in FIG. 19). It should be noted that the fact that the present peak derived from leucine was revealed in the above MS/MS processing. In other words, steps S200 to S203 shown in FIG. 10 have already been executed in the above description.

Figure 23:
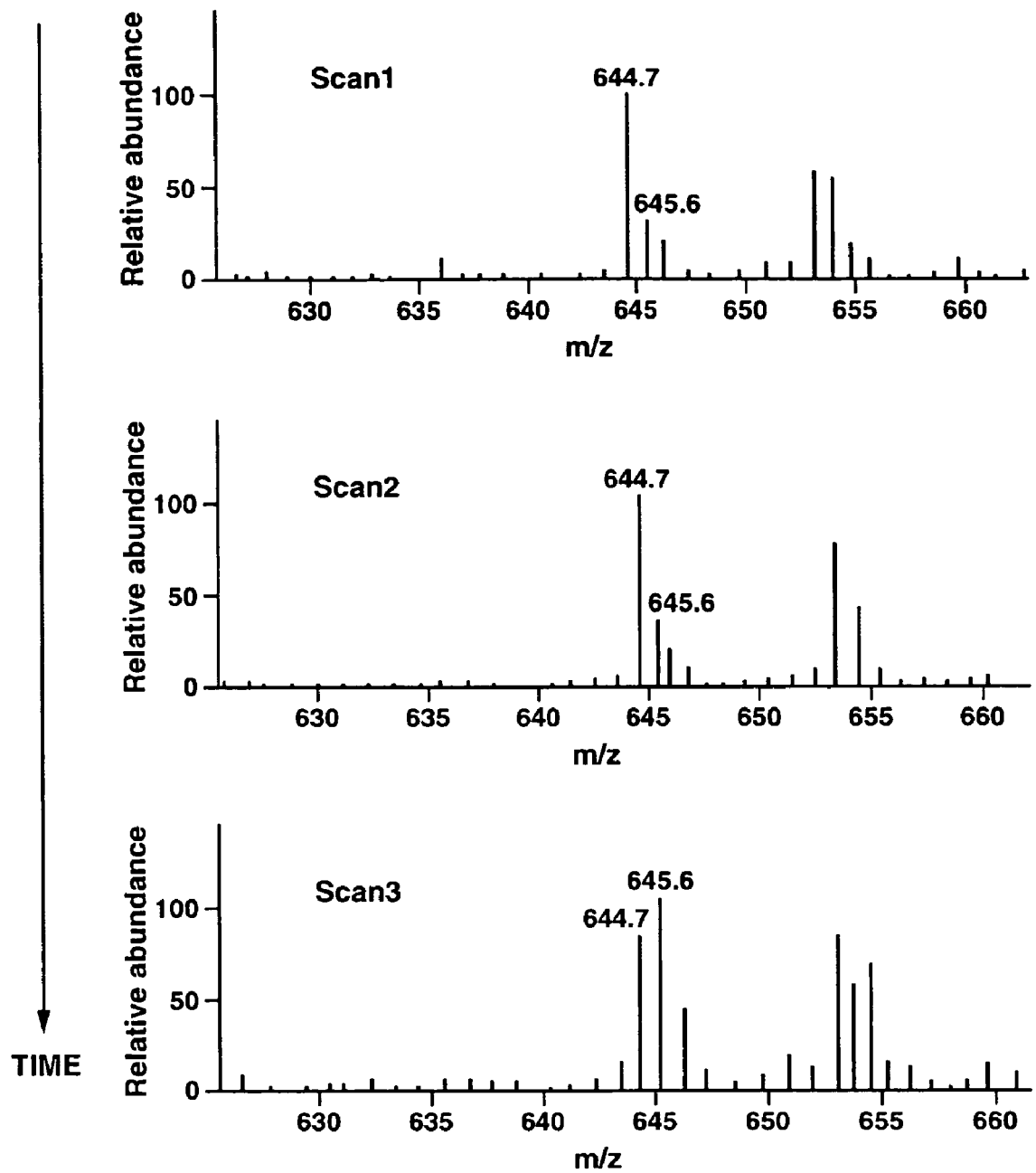
FIG. 23 shows mass spectra against times, in other words, at specific continuous scan numbers. In this figure, L indicates a peak derived from a protein containing leucines that are not isotope labeled.

FIG. 23 shows mass spectra in times, in other words, at specific continuous scan numbers. From the results shown in FIG. 23, the m/z value that is 644.7 reaches a maximum at scan 2 and decays thereafter is clear from the variation in the peak height.

Figure 24:
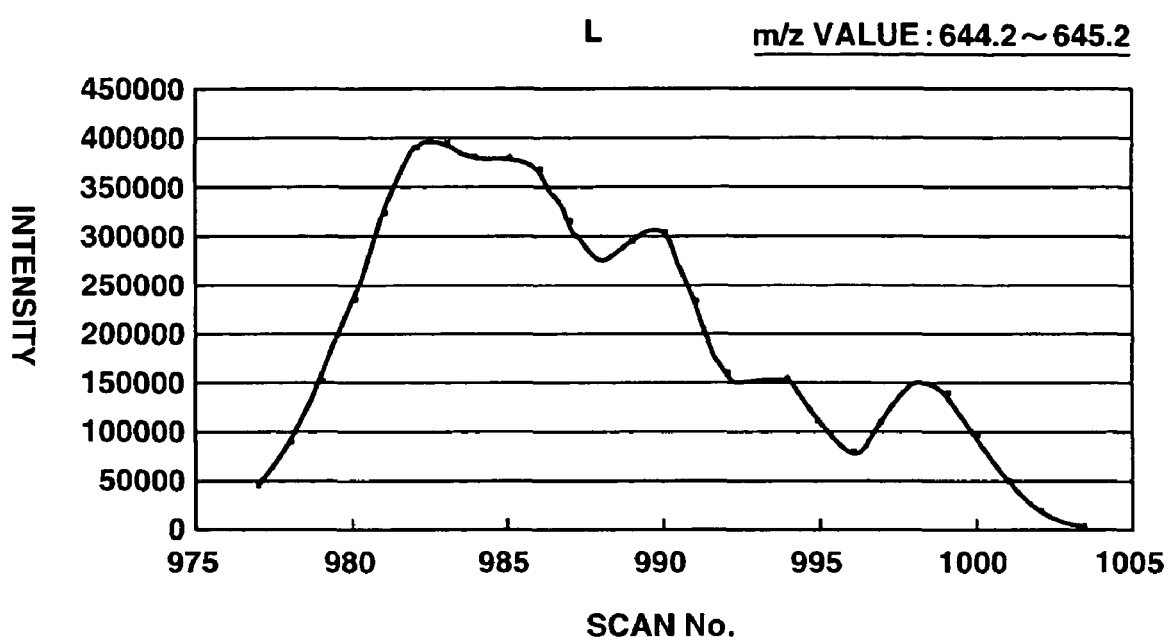
FIG. 24 shows a mass chromatogram at scan numbers 975 to 1005, with m/z values centered on 644.7, and 644.2 to 645.2 wide.

FIG. 24 shows a mass chromatogram resulting from continuously connecting only the necessary number of scan numbers shown in FIG. 23. Specifically, FIG. 24 shows the mass chromatogram created by connecting mass spectra from scan numbers 975 to 1005, centered on 644.7 (m/z value: 644.2 to 645.2).

The possibility to execute the above operation by calling the required scan information with the above-mentioned analysis software is easily understood by those skilled in the art.

Next, the focus was on a peak derived from a protein containing an isotope labeled leucine. In this case, the molecular weight the protein containing the isotope labeled leucine is greater by only 6/z than the unlabeled protein. Here, z is an electric charge that a protein possesses. From the result of mass spectra shown in FIG. 19, in step S204 of FIG. 10, focusing on a peak of mass spectra with 644.7+6/3=646.7 for the m/z value of the mass spectra derived from isotope labeled leucine of protein phosphatase 2a with an electric charge of 3, the focused mass spectra were extracted from the actually measured mass spectra (Step 205 in FIG. 10). Note that in FIG. 19, the mass spectra derived from the protein containing the isotope labeled leucine is represented by H.

Figure 25:
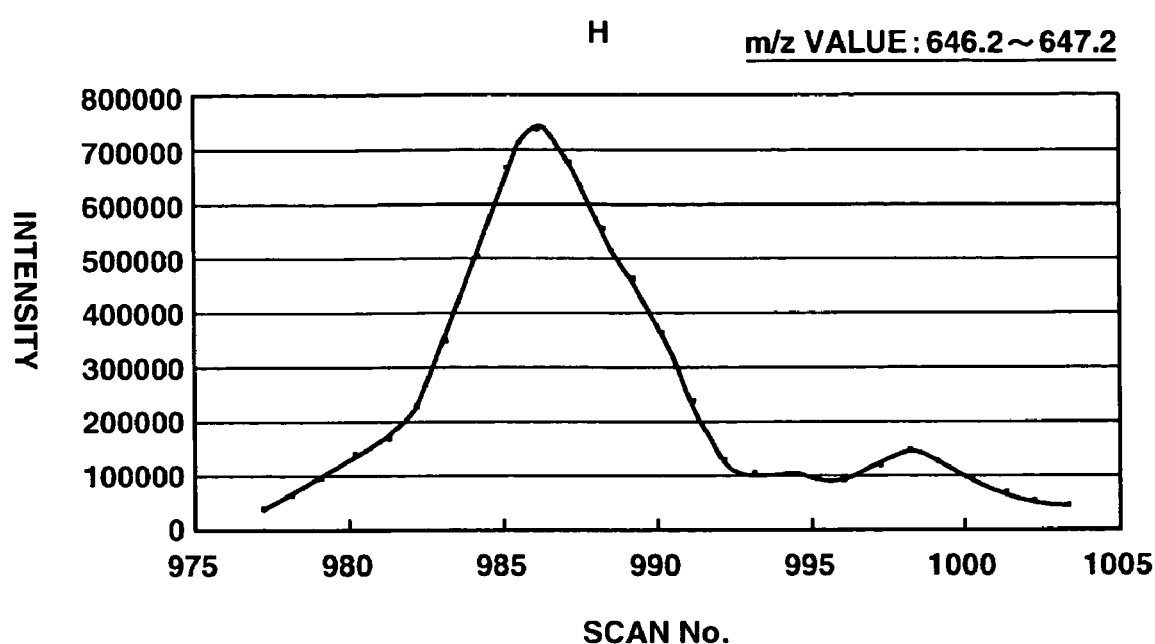
FIG. 25 shows a mass chromatogram at scan numbers 975 to 1005, with m/z values centered on 646.7, and 646.2 to 647.2 wide. In this figure, H indicates a peak derived from a protein containing a leucine that is isotope labeled.

FIG. 25 shows a mass chromatogram resulting from continuously connecting only the necessary number of scan numbers shown in FIG. 23. Specifically, FIG. 25 shows a mass chromatogram created by connecting mass spectra from scan numbers 975 to 1005, centered on 646.7 (m/z value: 646.2 to 647.2).

In general, for the mass chromatogram at the specific m/z value, if derived from the protein containing the single leucine, the single peak should be observed. However, from the results shown in FIGS. 24 and 25, a plurality of peaks have been observed.

Thus, in the present invention, in order to obtain the mass chromatogram derived from the specific protein, waveform separation processing of mass spectra obtained in FIG. 24 and FIG. 25 was carried out as follows in step S206 of FIG. 10. That is to say, waveform separation processing was executed by the curve fitting method, combining Gaussian function and Lorenz function.

Figure 26B:
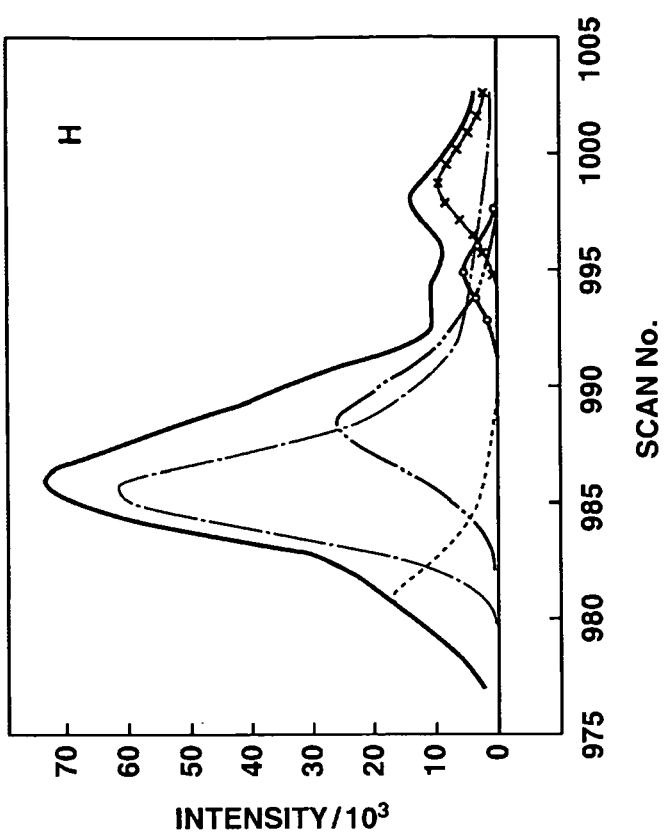
FIGS. 26A and 26B show the results of waveform separation processing according to the present invention.
Figure 26A:
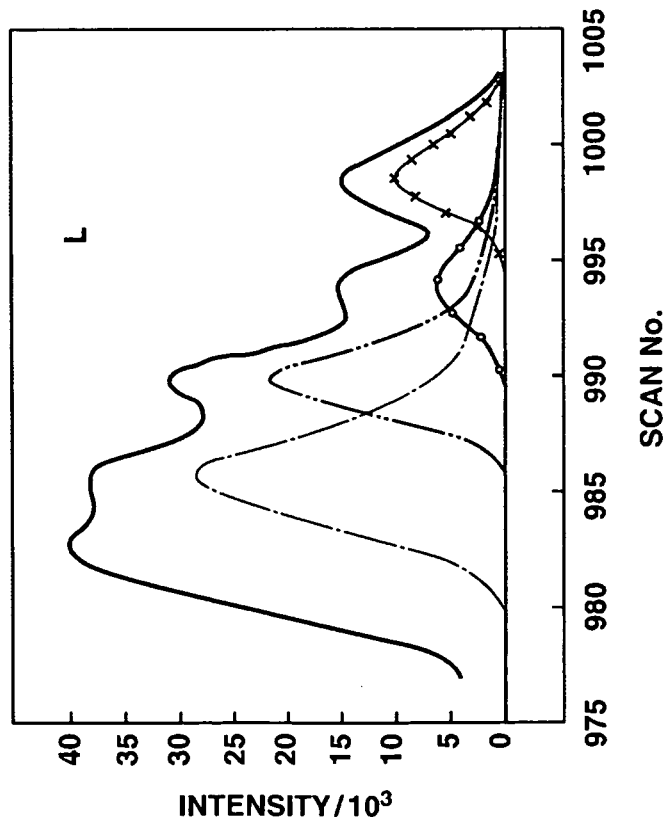

FIGS. 26A and 26B show the results of waveform separation processing according to the present invention. FIG. 26A shows the result of waveform separation processing of the mass chromatogram represented by L of protein phosphatase 2a derived from the wild type mouse brain (Wild) shown in FIG. 19, on the other hand, FIG. 26B shows the result of waveform separation processing of the mass chromatogram represented by H of isotope labeled protein phosphatase 2a derived from the wild type mouse brain (Wild) shown in FIG. 19. The actually measured mass chromatograms of L and H were each found to be overlaps of five mass chromatograms derived from specific proteins.

In waveform 1 to waveform 5 after waveform separation shown in FIG. 26A, the area of each waveform can be calculated by integration. Similarly, in waveform 6 to waveform 10 after waveform separation in FIG. 26B, the area of each waveform can be calculated by integration (step S207 of FIG. 10).

As necessary, the analysis results obtained from the above descriptions, can be stored in the memory unit 100 shown in FIG. 9. The area of waveform calculated in this way, by observing the ratio between the waveform derived from the protein containing the isotope labeled amino acid and the waveform derived from the protein containing non-isotope labeled amino acid, a time-dependent variation of the specific protein expressed in a cell of which the amino acid sequence has been determined can be quantitatively followed up from the ratio with the protein containing the isotope labeled amino acid.

FIG. 27 shows the results obtained by the analysis method of the present invention. FIG. 27 shows comparisons of peak intensity ratios derived from the wild type mouse brain (Wild) and derived from ADAM22 gene deficient mouse brain (K/O), when peaks of the same sequence derived from the internal standard substance that was the metabolically isotope labeled biological molecule were used and when the peaks from different sequences were used, in calculating the intensity ratios of peaks derived from the wild type mouse brain (Wild) and derived from ADAM22 gene deficient mouse brain (K/O) with respect to the peak derived from the internal standard substance that was the metabolically isotope labeled biological molecule.

The following experiment was carried out in order to confirm that absolute quantitation is possible.

Example 5

Quantitation of HSP60 in a Cell Containing an Internal Standard Substance that was a Metabolically Isotope Labeled Biological Molecule Example of Quantitation by ELISA A quantitation of HSP60 in a cell containing an internal standard substance that was the metabolically isotope labeled biological molecule was carried out using the Hsp60 ELISA Kit (Stressgen, EKS-600). The cell containing the internal standard substance that was the metabolically isotope labeled biological molecule obtained in Example 1 was washed with PBS (Sigma, D-8537), $3.75 \cdot 10^7$ cells were dissolved with 3 mL of a dissolution solution included with the Hsp60 ELISA Kit, and the centrifugation supernatant thereof served as the soluble fraction. Subsequent quantitation manipulation was carried out according to the instructions of the Hsp60 ELISA Kit. As a result, HSP60 concentration in the soluble fraction was determined to be 480 ng/mL. Thus, it was calculated that 1440 ng of HSP60 was present in $3.75 \times 10^7$ cells containing the internal standard substance that was the metabolically isotope labeled biological molecule.

Based on this value, quantitation of HSP60 in wild type mouse brain was carried out. The amount of protein extracted from 1 g of brain was 39.4 mg, and cells containing the same protein quantity of the internal standard substance that was the metabolically isotope labeled biological molecule ($12.1 \times 10^7$ cells) were added (Example 2); therefore, the amount of HSP60 in the internal standard substance that was the metabolically isotope labeled biological molecule that was added to the sample was $12.1 \times 10^7$ cells$\times 1440$ ng/$3.75 \times 10^7$ cells=4636 ng. On the other hand, the ratio intensities of peaks of HSP60 derived from a wild type mouse brain (sequence LPDGVAVLK) and HSP60 derived from the internal standard substance that was the metabolically isotope labeled biological molecule in the mass analysis peak was 6.8. Thus, it was calculated that 4636 ng$\times$6.8=approximately 32 µg of HSP60 was present per gram of the wild type mouse brain.

Consequently, it was confirmed that in a measurement by mass analysis, absolute quantitation could be carried out using this cell containing the internal standard substance that was the metabolically isotope labeled biological molecule.

Example 6

Quantitation of cMDH in a Cell Containing an Internal Standard Substance that was a Metabolically Isotope Labeled Biological Molecule Example where Specific Activity of a Purified Enzyme Standard Material was an Indicator An amount of $1.9 \times 10^7$ cells containing the internal standard substance that was the metabolically isotope labeled biological molecule obtained in Example 1 were dissolved in 1 mL M-PER (Pierce, 78501), and the centrifugation supernatant served as the soluble fraction.

<Preparation of Standard Substance> cMDH used as a standard substance was prepared as follows. Human cMDH gene was cloned, a FLAG tag was inserted on the N terminal side thereof and the resulting gene was integrated into a baculovirus vector. Then, the baculovirus having this vector was used to infect Sf9 cells, which were cultured. The cultured cells were recovered by centrifugal separation, the precipitate thereof was frozen at −80° C., then thawed, suspended with 25 mL of PBS, to extract cMDH. After extraction, the insoluble fraction was removed by centrifugal separation, and the supernatant thereof served as the crude extract. For the purification of cMDH, the crude extract was applied to 1.5 mL of Anti FLAG M2 Agarose (Sigma, A-2220), washed with 10 mL of PBS, then eluted with 5 mL of FLAG PEPTIDE (Sigma, F-3290) solution (0.1 mg/mL in PBS). The protein concentration in the main elution fraction was 0.4 mg/mL. This fraction was used in quantitation as a standard cMDH standard material.

<Measurement of Specific Activity>

For measurement of cMDH activity, 1 µL of cMDH solution was added to the following reaction solution, diminution of optical density at 340 nm derived from NADH was measured over time using a spectrophotometer (Amersham Bioscience, Ultrospec 4300 pro), and the diminution of optical density per minute served as the cMDH activity. As a result, diminution of optical density was 0.068/minute when 1 µL of a solution with a cMDH concentration of 0.02 mg/mL was used, and the diminution of optical density was 0.057/minute when 1 µL of the soluble fraction was used.

| | |
|---|---|
| Reaction buffer solution: 10 mM Tris-HCl (pH 7.4)-0.15 M NaCl | 0.98 mL |
| Oxaloacetic acid (Wako Pure Chemical Industries, Lot. SEH1972): 10 mM aqueous solution | 0.01 mL |
| NADH (Sigma, Lot.102K701): 10 mM aqueous solution | 0.01 mL |
| Reaction solution: | 1 mL |

From this measurement result, the cMDH concentration in the wild type mouse brain was quantitated as follows. Protein quantity in the soluble fraction was 6.2 mg/mL (Example 1). In addition, cMDH concentration with respect to the solution in the soluble fraction was 0.057/0.068×0.02 mg/mL=0.0167 mg/mL. Thus, the cMDH concentration with respect to the amount of protein in the soluble fraction was calculated to be 0.0167/6.2=0.0027 mg/mg.

Further, in the measurement by mass analysis (Example), the ratio of intensities of peaks of cMDH derived from the wild type mouse brain and cMDH derived from the internal standard substance that was the metabolically isotope labeled biological molecule was approximately 2.0 (Table 1, Wild). Thus, cMDH concentration with respect to the amount of protein in the soluble fraction derived from the wild type mouse brain was 0.0027×2=0.0054 mg/mg. Furthermore, 39.4 mg of protein per gram of wild type mouse brain was contained (Example 2). Therefore, it could be calculated that 39.4×0.0054=0.21 mg of cMDH was present per gram of wild type mouse brain.

Therefore, it was found that in the measurement by mass analysis, absolute quantitation could be carried out by using this cell containing the internal standard substance that was the metabolically isotope labeled biological molecule.

Example 7

Absolute Quantitation of Biological Molecule

Example Using a Synthetic Peptide

An amount of $1.9 \times 10^7$ cells containing the internal standard substance that was the metabolically isotope labeled biological molecule obtained in Example 1 was dissolved with 1 mL of M-PER (Pierce, 78501) and the centrifugation supernatant thereof served as the soluble fraction.

<Preparation of Synthetic Peptide>

For the 5 types of synthetic peptide set forth in the following, the preparations were ordered and obtained from Peptide Institute Inc (Osaka). SQIHDIVLVGGSTR (heat shock 70 kDa protein 8 isoform 1), HFSVEGQLEFR (heat shock protein 90-beta), HLIPAANTGESK (14-3-3 epsilon), SYELPDGQVITIGNER (mutant beta-actin (beta'-actin), ELEAELEDER (Myosin heavy chain, nonmuscle type B). An amount of 2 pmol each of these synthetic peptides was added to the soluble fraction. An amount of 3 μL of a mixed solution of soluble fraction (990 ng/μL) and synthetic peptide (91 nmol/μL) was measured by LC/MSMS (QSTAR PULSAR i, manufactured by Applied Corporation). The measurement conditions were as follows.

<LC Condition>

Auto sampler: HTS-PAL (manufactured by CTC Analytica Corporation)

Pump and controller: two LC-10 Avp's (high pressure gradient systems), SCL-10Avp (manufactured by Shimadzu Corporation)

Flow splitter: resistance tube (fused silica capillary with 25 μm internal diameter and 150 mm length, manufactured by GL Science) stuck to a 3-way tee (manufactured by GL Science).

Column: electrospray needle (manufactured by New Objective Inc., internal diameter: 0.1 mm; length: 150 mm; tip diameter: 8 μm; conducting substance envelope: none) slurry filled with a reverse phase system filling agent (ReproSil-Pur 120 C18-AQ, 3 μm, manufactured by Dr. Maisch Corporation).

Mobile phase: (A) 0.5% acetic acid aqueous solution, (B) 0.5% acetic acid aqueous solution, 80% acetonitrile Flow rate: 0.06 mL/min (value at pump exit), 25 nL/min (after split)

Gradient elution condition:

TABLE 2

| Time (Minute) | Concentration of mobile phase B |
|---|---|
| 0 | 5 |
| 5 | 10 |
| 65 | 25 |
| 70 | 100 |
| 80 | 100 |
| 80.1 | 5 |
| 110 | 5 |

Measurement time: 110 minutes

Mass analysis conditions:

ESI interface: for nanoelectrospray (manufactured by Protana Corporation)

MS scan: 350-1400 amu, 1.0 second

MSMS scan: maximum 4 times per MS scan, 85-1400 amu, 1.5 seconds each

Measurement time: 110 minutes

Spray voltage: 2400V

Identification of peptide sequence was carried out by sending out the MS/MS spectra to the database search engine Mascot (MatrixScience, London). NCBI protein database (http://www4.ncbi.nlm.nih.gov/) was used for the protein database. Quantitation was carried out using the ratio of intensities of peaks on the mass spectra. As the metabolically isotope labeled biological molecule in the soluble fraction had leucine labeled with 6 stable isotopes $^{13}C$, it could be easily distinguished from the peak derived from the added synthetic peptide on the mass spectra.

In addition, based on the value calculated from the peak intensity ratio, absolute quantity of each protein that was present in the soluble fraction was shown in Table 3 (wt % at the right end: proportion contained in soluble fraction)

TABLE 3

| Protein | Peptide | Ratio $_{(label/unlabel)}$ | Protein $_{(fmol/uL)}$ | MW (kD) | ng/uL | wt % |
|---|---|---|---|---|---|---|
| heat shock 70 kDa protein 8 Isoform | SQIHDIVLVGGSTR | 1.36 | 123.64 | 70.97 | 8.77 | 0.88 |
| heat shock protein 90-beta | HFSVEGQLEFR | 1.65 | 150.00 | 83.42 | 12.51 | 1.26 |
| 14-3-3 epsilon | HLIPAANTGESK | 0.24 | 21.82 | 29.32 | 0.64 | 0.06 |
| mutant beta-actin (beta'-actin) | SYELPDGQVITIGN | 3.47 | 315.45 | 41.98 | 13.24 | 1.34 |
| Myosin heavy chain, nonmuscle tyr | ELEAELEDER | 0.058 | 5.27 | 229.48 | 1.21 | 0.12 |

Table 3: It is shown that results of measurement of the absolute quantity of each protein expressed in the internal standard substance that was the metabolically isotope labeled biological molecule.

On the other hand, as shown in Example 4, the ratio of the intensities of the peaks of the protein derived from the wild type mouse brain and the protein derived from the internal standard substance that was the metabolically isotope labeled biological molecule was determined. Then, the wild type mouse brain and the cell containing the internal standard substance that was the metabolically isotope labeled biological molecule were each mixed in such a way that the protein quantity was identical, and measured (Example 4). In addition, the protein quantity was 39.4 mg per gram of mouse brain (Example 2). Thus, the absolute quantity contained in one gram of mouse brain could be calculated as in Table 4.

Consequently, it was found that in the measurement by mass analysis, absolute quantitation could be carried out by using this cell containing the internal standard substance that was the metabolically isotope labeled biological molecule.

TABLE 4

| Protein | Ration in the wild-type strain | mg quantity per gram of brain (wild-type strain) | Ratio in the knock-out | mg quantity per gram of brain (knock-out strain) |
|---|---|---|---|---|
| heat shock 70 kDa protein 8 isoforml | 1.05 | 0.33 | 1.07 | 0.33 |
| heat shock protein 90-beta | 1.64 | 0.30 | 1.64 | 0.30 |
| 14-3-3 epsilon | 0.25 | 0.10 | 0.27 | 0.09 |
| beta'-actin | 0.38 | 1.38 | 0.39 | 1.35 |
| Myosin heavy chain | 0.39 | 0.12 | 0.49 | 0.10 |

Table 4: it is shown results of measurement of the absolute quantity of each protein in the wild type mouse brain and the ADAM22 gene deficient mouse brain.

As mentioned above, by absolutely quantitating each protein in the cell containing the internal standard substance that was the metabolically isotope labeled biological molecule, it was possible to quantitate a biological molecule absolutely and comprehensively.

Next, a linking between the data concerning the mass spectra after waveform separation obtained in Example 4, in particular, the value of the quantitative value, and functional information, will be described.

Example 8

First, as illustrated in Example 4, one or a plurality of sequences after waveform separation were considered. FIG. 28 shows a sequence after waveform separation considered in one example of the present invention, and the quantitative value of this sequence. Specifically, in the example four sequences were considered: (1) ALVLELCCNDESGED-VEVPYVR, (2) KPLLESGTLGTK, (3) NFPNAIE-HTLQWAR and (4) YFLVGAGAIGCELLK. In addition, the quantitative value shown in FIG. 28 represents the value for each of the sequences. Note that isotope labeling was carried out using L-Leucine labeled with a stable isotope. As shown in FIG. 28, a plurality of quantitative values were calculated for an identical peptide for the sequence NFPNAIE-HTLQWAR and the sequence YFLVGAGAIGCELLK.

Based on the peptide sequence shown in FIG. 28, retrieving with the external database, specifically, the NCBInr database, was performed, and in the database, a pattern search was executed in HomoSapiens. As a result, for each sequence to be searched, a GiNo of the identified protein was obtained (see FIG. 29). For all the sequences to be searched, (1) gi|23510340|ref|NP_695012.1|, (2) gi|35830|emb|CAA40296.1|, (3) gi|24485|emb|CAA37078.1| were identified. When the search was performed in LocusLink regarding these three GiNo's, they were summarized to LocusID=7317. The results shown in FIGS. 30A and 30B were obtained for this LocusID.

On the other hand, regarding the protein with LocusID=7317, when isotope labeled with L-Leucine, the quantitative value of (the area of waveform from protein with LocusID=7317)/(the area of waveform of isotope labeled LocusID=7317) was 1.10726332649. This value is different from the value obtained in each peptide sequence shown in FIG. 28; however, if it is adopted as the quantitative value of the protein, and if this quantitative value is used for each protein, linking of the protein with the well known function and the quantitative value is possible. Note that in the present invention, since the sample is pre-digested with the enzyme or the like and decomposed for mass analysis, actual mass spectra of the protein per se was not measured. However, under the assumption that the mass spectra of the protein per se were measured, information suggesting the quantitative value of the protein and the biological function can be provided.

Example 9

Preparation of Synthetic Peptide

Among the 114 types of synthetic peptide set forth in the following, 8 types were obtained from Peptide Institute Inc (Osaka). The remaining 106 types (containing at least one Leu and one Tyr) were synthesized in-house using the Shimadzu PSSM-8 peptide synthesizer. For the synthesis method and the cleavage method, the protocol for F-moc included with the device was followed. After fractionation under the HPLC conditions shown below, the mass number of the target fraction was confirmed with MS. Furthermore, target fraction was analyzed with HPLC-UV (280 nm), and the solution concentration was calculated from the peak area of the main peak and the molar extinction coefficient of Tyr.

Fractionation HPLC Conditions

LC system (auto sampler, pump, UV detector, fraction collector, controller):
LC10Avp (Manufactured by Shimadzu Corporation)
Column: YMC-Pack Pro C18 (10 mm diameter, 150 mm length)
Mobile phase: (A) 0.1% trifluoroacetic acid aqueous solution, (B) acetonitrile
Flow rate: 4 mL/min
Detector wavelength: 220 nm
Gradient elution condition:

TABLE 5

| Time (Minute) | Concentration of mobile phase B |
|---|---|
| 0 | 5 |
| 10 | 60 |
| 10.01 | 5 |
| 20 | 5 |

Measurement time: 20 minutes

Analytical HPLC Conditions

Identical to the above except for flow rate, column diameter and detector wavelength.
Column: YMC-Pack Pro C18 (4.6 mm diameter, 150 mm length)
Flow rate: 1 mL/min
Detector wavelength: 280 nm An amount of 2 pmol each of synthetic peptides obtained in this way was added to the earlier soluble fraction. An amount of 3 μL of a mixed solution of soluble fraction (990 ng/μL) and synthetic peptide (91 nmol/μL) were measured by LC/MSMS (QSTAR PULSAR i, manufactured by Applied Corporation). In addition, mixed solutions in which the quantity of synthetic peptide was 5-times and ⅕ were prepared and measured in the same way. The measurement conditions were as follows.

TABLE 6

| Time (Minute) | Concentration of mobile phase B |
|---|---|
| 0 | 5 |
| 5 | 10 |
| 65 | 25 |
| 70 | 100 |
| 80 | 100 |
| 80.1 | 5 |
| 110 | 5 |

Measurement time: 110 minutes
MS conditions:
ESI interface: for nanoelectrospray (manufactured by Protan)
MS scan: 350-1400 amu, 1.0 second
MSMS scan: maximum 4 times per MS scan, 85-1400 amu, 1.5 seconds each
Measurement time: 110 minutes
Spray voltage: 2400V Identification of peptide sequence was carried out by sending out the MS/MS spectra to the database search engine Mascot (MatrixScience, London). SwissProt protein database (http://kr.expasy.org/sprot/) was used for the protein database. Quantitation was carried out using the ratio of intensities of peaks on the mass spectra. As the metabolically isotope labeled biological molecule in the soluble fraction had leucine labeled with 6 stable isotopes $^{13}C$, it could be easily distinguished from the peak derived from the added synthetic peptide on the mass spectra.

In addition, based on the value calculated from the peak intensity ratio, absolute quantity of each protein that was present in the soluble fraction is shown in Table 4 (Conc in neuro2a at the right end: proportion contained per mg of neuro2a soluble fraction protein).

TABLE 7

| Accession number | Protein Name | Peptide sequence | Source | Conc in Neuro2a (pmol/mg) |
|---|---|---|---|---|
| P35215 | 14-3-3 protein zeta/delta (Protein kinase C Inhibi | NLLSVAYK | In-house | 180.9 |
| P10852 | 4F2 cell-surface antigen heavy chain (4F2hc) | YLVVLNFR | In-house | 10.3 |
| P57780 | Alpha-actinin 4 (Non-muscle alpha-actinin 4) (F-actin cross linking protein) | HRPELIEYDK | In-house | 4.6 |
| P05201 | Aspartate aminotransferase, cytoplasmic (EC 2.6.1.1) (Transaminase A) | VNLGVGAYR | In-house | 6.3 |
| P05202 | Aspartate aminotransferase, mitochondrial precursor | ILIRPLYSNPPLNGAR | In-house | 19.5 |
| Q91V92 | ATP-citrate synthase (EC 2.3.3.8) (ATP-citrate (pro-S-)-lyase) (Citrate cleavage enzyme) | DGVYILDLAAK | In-house | 19.4 |
| P48975 | Actin, cytoplasmic 1 (Beta-actin). | SYELPDGQVITIGNER | Peptide Institute, Inc | 572.9 |
| P51881 | ADP, ATP carrier protein, fibroblast Isoform | YFPTQALNFAFK | In-house | 125.4 |
| P05064 | Fructose-bisphosphate aldolase A (EC 4.1.2.13) | LQSIGTENTEENR | Peptide Institute, Inc | 99.8 |
| Q61024 | Asparagine synthetase [glutamine-hydrolyzing] (EC 6.3.5.4) | ELYLFDVLR | In-house | 19.4 |
| Q03265 | ATP synthase alpha chain, mitochondrial precursor | HALIIYDDLSK | In-house | 70.5 |
| P56480 | ATP synthase beta chain, mitochondrial precursor (EC 3.6.3.14) | VALTGLTVAEYFR | In-house | 79.8 |
| Q9DCX2 | ATP synthase D chain, mitochondrial (EC 3.6.3.14) | YTALVDQEEK | In-house | 13.1 |
| Q06647 | ATP synthase oligomycin sensitivity conferral protein | YATALYSAASK | In-house | 37.1 |
| Q91V12 | Cytosolic acyl coenzyme A thioester hydrolase (EC 3.1.2.2) | VLEVPPIVYLR | In-house | 10.8 |
| Q64433 | 10 kDa heat shock protein, mitochondrial (Hsp10) (10 kDa chaperonin) (CPN10) | DYFLFR | In-house | 41.0 |
| P11442 | Clathrin heavy chain. | ALEHFTDLYDIK | Peptide Institute, Inc | 26.1 |

TABLE 7-continued

| Accession number | Protein Name | Peptide sequence | Source | Conc in Neuro2a (pmol/mg) |
|---|---|---|---|---|
| P18760 | Cofilin, non-muscle isoform | YALYDATYETK | In-house | 49.6 |
| P14211 | Calreticulin precursor (CRP55) (Calregulin) | FYALSAK | In-house | 54.2 |
| Q9JIK5 | Nucleolar RNA helicase II (Nucleolar RNA helicase | STYEQVDLIGK | In-house | 14.3 |
| Q91VC3 | Probable ATP-dependent helicase DDX48 (DEAD-box protein 48) | LDYGQHVVAGTPGR | In-house | 4.6 |
| Q62167 | DEAD-box protein 3 (DEAD-box RNA helicase DEAD3) (mDEAD3) (Embryonic RNA helicase) | YLVLDEADR | In-house | 6.8 |
| Q61656 | Probable RNA-dependent helicase p68 (DEAD-box protein p68) (DEAD-box protein 5) | NFYQEHPDLAR | In-house | 14.8 |
| O70133 | ATP-dependent RNA helicase A (Nuclear DNA helicase II) (NDH II) (DEAH-box protein 9) | DFVNYLVR | In-house | 9.7 |

TABLE 8

| Accession number | Protein Name | Peptide sequence | Source | Conc in Neuro2a (pmol/mg) |
|---|---|---|---|---|
| Q62188 | Dihydropyrimidinase related protein-3 (DRP-3) | IFNLYPR | In-house | 14.3 |
| P20001 | Elongation factor 1-alpha 1 (EF-1-alpha-1) | EHALLAYTLGVK | In-house | 413.5 |
| Q9D8N0 | Elongation factor 1-gamma (EF-1-gamma) (eEF-1B gamma) | ALIAAQYSGAQVR | In-house | 30.2 |
| P58252 | Elongation factor 2 (EF-2). | GVQYLNEIK | In-house | 56.1 |
| Q60899 | ELAV-like protein 2 (Hu-antigen B) (HuB) (ELAV-like neuronal protein 1) | DANLYVSGLPK | In-house | 14.8 |
| P17182 | Alpha enolase (EC 4.2.1.11) | YITPDQLADLYK | In-house | 283.3 |
| P08113 | Endoplasmin precursor | GLFDEYGSK | In-house | 42.8 |
| P19096 | Fatty acid synthase (EC 2.3.1.85) | ELSFAAVSFYHK | In-house | 14.8 |
| Q61553 | Fascin (Singed-like protein) | YLAPSGPSGTLK | In-house | 11.4 |
| P16858 | Glyceraldehyde 3-phosphate dehydrogenase | YDNSLK | In-house | 190.0 |
| Q61598 | Rab GDP dissociation inhibitor beta-2 (Rab GDI beta-2) (GDI-3) | FLVYVANFDEK | In-house | 17.7 |
| O35501 | Stress-70 protein, mitochondrial precursor | VINEPTAAALAYGLDK | In-house | 92.6 |
| P07823 | 78 kDa glucose-regulated protein precursor (GRP 78) | NELESYAYSLK | In-house | 12.0 |
| P02304 | Histone H4 | ISGLIYEETR | In-house | 126.5 |
| Q63413 | Probable ATP-dependent RNA helicase p47 | LTLHGLQQYYVK | In-house | 41.2 |
| P19378 | Heat shock cognate 71 kDa protein. | SQIHDIVLVGGSTR | Peptide Institute, Inc | 390.5 |
| P07901 | Heat shock protein HSP 90-alpha (HSP 86) | HFSVEGQLEFR | Peptide Institute, Inc | 446.6 |
| P23116 | Eukaryotic translation initiation factor 3 subunit 10 (eIF-3 theta) (eIF3 p167) | EEQHQLAVNAYLK | In-house | 9.1 |
| P03975 | IgE-binding protein. | VHAPVEYLQIK | In-house | 58.2 |
| Q8CAQ8 | Mitochondrial inner membrane protein (Mitofilin) | VEFEQGLSEK | In-house | 8.6 |

TABLE 8-continued

| Accession number | Protein Name | Peptide sequence | Source | Conc in Neuro2a (pmol/mg) |
|---|---|---|---|---|
| P09055 | Integrin beta-1 precursor (Fibronectin receptor beta subunit) (CD29 antigen) | LPDGVTINYK | In-house | 3.4 |
| Q9D7G0 | Ribose-phosphate pyrophosphokinase I (EC 2.7.6.1) | VYAILTHGIFSGPAISR | In-house | 15.4 |
| P52480 | Pyruvate kinase, M2 isozyme (EC 2.7.1.40). | IYVDDGLISLQVK | In-house | 102.4 |
| Q61881 | DNA replication licensing factor MCM7 (CDC47 homolog) | SQLLSYIDR | In-house | 3.4 |

TABLE 9

| Accession number | Protein Name | Peptide sequence | Source | Conc in Neuro2a (pmol/mg) |
|---|---|---|---|---|
| Q8VEM8 | Phosphate carrier protein, mitochondrial precursor | EEGLNAFYK | In-house | 22.8 |
| Q13126 | S-methyl-5-thioadenosine phosphorylase | YVDTPFGKPSDALILGK | In-house | 20.4 |
| Q9JLT0 | Myosin heavy chain, nonmuscle type B | ELEAELEDER | Peptide Institute, Inc | 16.5 |
| P28656 | Nucleosome assembly protein 1-like 1 (NAP-1 related protein) (Brain protein DN38) | FYEEVHDLER | In-house | 16.5 |
| P09405 | Nucleolin (Protein C23) | FGYVDFESAEDLEK | In-house | 57.0 |
| Q60432 | 150 kDa oxygen-regulated protein precursor (Orp150) (Hypoxia up-regulated 1) | DAVIYPILVEFTR | In-house | 14.3 |
| P50580 | Proliferation-associated protein 2G4 (Proliferation-associated protein 1) | ITSGPFEPDLYK | In-house | 19.4 |
| P29341 | Polyadenylate-binding protein 1 (Poly(A)-binding protein 1) (PABP 1) | SLGYAYVNFQQPADAER | In-house | 18.5 |
| P35700 | Peroxiredoxin 1 (EC 1.11.1.-) (Thioredoxin peroxidase 2) | DISLSEYK | In-house | 46.1 |
| Q51171 | Peroxiredoxin 2 (EC 1.11.1.-) (Thioredoxin peroxidase 1) | SLSQNYGVLK | In-house | 24.5 |
| O08807 | Peroxiredoxin 4 (EC 1.11.1.-) (Prx-IV) | LVQAFQYTDK | In-house | 34.2 |
| O08709 | Peroxiredoxin 6 (EC 1.11.1.-) (Antioxidant protein 2) (1-Cys peroxiredoxin) (1-Cys PRX) | LSILYPATTGR | In-house | 12.0 |
| P15331 | Peripherin. | YADLSDAANR | In-house | 39.7 |
| P50310 | Phosphoglycerate kinase (EC 2.7.2.3). | LGDVYVNDAFGTAHR | In-house | 14.3 |
| Q9DBJ1 | Phosphoglycerate mutase 1 (EC 5.4.2.1) | HGESAWNLENR | Peptide Institute, Inc | 54.2 |
| Q60932 | Voltage-dependent anion-selective channel protein | GYGFGLIK | In-house | 34.2 |
| Q60930 | Voltage-dependent anion-selective channel protein | YQLDPTASISAK | In-house | 25.7 |
| Q60931 | Voltage-dependent anion-selective channel protein 3 (VDAC-3) (mVDAC3) | LSQNNFALGYK | In-house | 6.8 |
| P97371 | Proteasome activator complex subunit 1 (Proteasome activator 28-alpha subunit) (PA28alpha) | TENLLGSYFPK | In-house | 9.1 |
| P46638 | Ras-related protein Rab-11B | NILTEIYR | In-house | 4.0 |
| P19253 | 60S ribosomal protein L13a | FAYLGR | In-house | 22.8 |

TABLE 9-continued

| Accession number | Protein Name | Peptide sequence | Source | Conc in Neuro2a (pmol/mg) |
|---|---|---|---|---|
| P17080 | GTP-binding nuclear protein RAN (TC4) (Ran GTPase) | NLQYYDISAK | In-house | 121.1 |
| P10113 | Ras-related protein Rap-1A (C21KG) (KREV-1 protein) (GTP-binding protein SMG-P21A) (G-22K) | INVNEIFYDLVR | In-house | 17.1 |
| Q60972 | Chromatin assembly factor 1 subunit C (CAF-1 subunit C) | TPSSDVLVFDYTK | In-house | 21.7 |

TABLE 10

| Accession number | Protein Name | Peptide sequence | Source | Conc in Neuro2a (pmol/mg) |
|---|---|---|---|---|
| Q91YQ5 | Dolichyl-diphosphooligosaccharide-protein glycosyltransferase 67 kDa subunit precursor | SEDVLDYGPFK | In-house | 8.0 |
| P39026 | 60S ribosomal protein L11. | YDGIILPGK | In-house | 51.3 |
| Q9CPR4 | 60S ribosomal protein L17(L23). | YSLDPENPTK | In-house | 42.8 |
| P41104 | 60S ribosomal protein L22 (Heparin binding protein HBp15) | ESYELR | In-house | 44.9 |
| P08526 | 60S ribosomal protein L27. | YSVDIPLDK | In-house | 40.7 |
| P04645 | 60S ribosomal protein L30 | YVLGYK | In-house | 18.2 |
| Q9D1R9 | 60S ribosomal protein L34. | LSYNTASNK | In-house | 45.6 |
| P47911 | 60S ribosomal protein L6 (TAX-responsive enhancer element binding protein 107) (TAXREB107) | HLTDAYFK | In-house | 23.9 |
| P14148 | 60S ribosomal protein L7. | SYNELIYK | In-house | 57.0 |
| P14869 | 60S acidic ribosomal protein P0 (L10E). | SNYFLK | In-house | 48.5 |
| O35737 | Heterogeneous nuclear ribonucleoprotein H (hnRNP H) | ATENDIYNFFSPLNPVR | In-house | 58.9 |
| Q7TMK9 | Heterogeneous nuclear ribonucleoprotein Q (hnRNP Q) (hnRNP-Q) | TGYTLDVTTGQR | In-house | 12.5 |
| P09900 | 40S ribosomal protein S10 | IAIYELLFK | In-house | 31.4 |
| Q02546 | 40S ribosomal protein S13 | GLSQSALPYR | In-house | 23.4 |
| P17008 | 40S ribosomal protein S16. | DILIQYDR | In-house | 216.6 |
| P25444 | 40S ribosomal protein S2 (S4) (LLREP3 protein) | SPYQEFTDHLVK | In-house | 26.8 |
| P17073 | 40S ribosomal protein S3 | ELAEDGYSGVEVR | In-house | 35.3 |
| P97351 | 40S ribosomal protein S3a | TTDGYLLR | In-house | 30.2 |
| P47961 | 40S ribosomal protein S4. | YALTGDEVK | In-house | 77.0 |
| P09058 | 40S ribosomal protein S8. | ADGYVLEGK | In-house | 45.6 |
| P29314 | 40S ribosomal protein S9. | LDYILGLK | In-house | 64.1 |
| P43331 | Small nuclear ribonucleoprotein Sm D3 (snRNP core protein D3) (Sm-D3) | VAQLEQVYIR | In-house | 20.5 |
| P16086 | Spectrin alpha chain, brain (Spectrin, non-erythroid alpha chain) (Alpha-II spectrin) | LLVSSEDYGR | In-house | 3.4 |
| Q62261 | Spectrin beta chain, brain 1 (Spectrin, non-erythroid beta chain 1) (Beta-II spectrin) | ITDLYTDLR | In-house | 6.3 |

TABLE 11

| Accession number | Protein Name | Peptide sequence | Source | Conc in Neuro2a (pmol/mg) |
|---|---|---|---|---|
| Q99L47 | Hsc70-interacting protein (Hip) (Putative tumor suppressor ST13) | LAILYAK | In-house | 37.2 |
| Q922B2 | Aspartyl-tRNA synthetase (EC 6.1.1.12) (Aspartate-tRNA ligase) (AspRS) | IYVISLAEPR | In-house | 12.0 |
| Q9CZD3 | Glycyl-tRNA synthetase (EC 6.1.1.14) (Glycine-tRN | IYLYLTK | In-house | 38.7 |
| Q99MN1 | Lysyl-tRNA synthetase (EC 6.1.1.6) (Lysine-tRNA ligase) (LysRS) | LIFYDLR | In-house | 15.4 |
| P26638 | Seryl-tRNA synthetase (EC 6.1.1.11) (Serine-tRNA ligase) (SerRS) | YLIATSEQPIAALHR | In-house | 35.2 |
| Q9Z1Q9 | Valyl-tRNA synthetase 2 (EC 6.1.1.9) (Valine-tRNA ligase 2) (ValRS 2) | TLLPVPGYK | In-house | 8.0 |
| Q9WVA4 | Transgelin 2. | GPSYGLSR | In-house | 61.6 |
| P05213 | Tubulin alpha-2 chain (Alpha-tubulin 2). | AVFVDLEPTVIDEVR | Peptide Institute, Inc | 846.5 |
| P05218 | Tubulin beta-5 chain | YLTVAAVFR | In-house | 319.2 |
| P11983 | T-complex protein 1, alpha subunit B (TCP-1-alpha) | YPVNSVNILK | In-house | 17.1 |
| P80315 | T-complex protein 1, delta subunit (TCP-1-delta) (CCT-delta) (A45) | AYILNLVK | In-house | 32.1 |
| P42932 | T-complex protein 1, theta subunit (TCP-1-theta) | QYGSETFLAK | In-house | 45.6 |
| Q62318 | Transcription intermediary factor 1-beta (TIF1-beta) (Tripartite motif protein 28) | DHQYQFLEDAVR | In-house | 7.4 |
| Q01320 | DNA topoisomerase II, alpha isozyme (EC 5.99.1.3). | TPSLITDYR | In-house | 17.1 |
| Q9CQM9 | Thioredoxin-like protein 2 | YEISSVPTFLFFK | In-house | 6.8 |
| O08810 | 116 kDa U5 small nuclear ribonucleoprotein component (U5 snRNP-specific protein, 116 kDa) | SFVEFILEPLYK | In-house | 156.8 |
| Q9DB77 | Ubiquinol-cytochrome C reductase complex core protein 2, mitochondrial precursor | IIENLHDVAYK | In-house | 8.0 |
| P20152 | Vimentin. | SLYSSSPGGAYVTR | In-house | 159.6 |

Table 7 to Table 11: It is shown results of measurements of the each protein expressed in the internal standard substance that was the metabolically isotope labeled biological molecule.

On the other hand, as shown in Example 4, the ratios of the intensities of the peaks of the protein derived from the wild type and the ADAM22 knock out mouse brain, and of the protein derived from the internal standard substance that was the metabolically isotope labeled biological molecule were determined. Then, as the wild type mouse brain and the cell containing the internal standard substance that was the metabolically isotope labeled biological molecule were each mixed in such a way that the protein quantity was identical, and measured, the weight mixing proportion was known (Example 4). Thus, the absolute quantity contained in one gram of mouse brain could be calculated as in Table 8. Therefore, it was found that in the measurement by MS, absolute quantitation could be carried out by using this cell containing the internal standard substance that was the metabolically isotope labeled biological molecule.

TABLE 12

| Accession number | Protein Name | Peptide sequence | Conc in Neuro2a (pmol/mg) | Conc in Brain wild type (pmol/mg) | Conc in Brain (ADAM22-ko) |
|---|---|---|---|---|---|
| P35215 | 14-3-3 protein zeta/delta (Protein kinase C Inhibi | NLLSVAYK | 180.9 | 326.54 | 254.51 |
| P10852 | 4F2 cell-surface antigen heavy chain (4F2hc) | YLVVLNFR | 10.3 | 6.63 | 6.66 |

TABLE 12-continued

| Accession number | Protein Name | Peptide sequence | Conc in Neuro2a (pmol/mg) | Conc in Brain wild type (pmol/mg) | Conc in Brain (ADAM22-ko) |
|---|---|---|---|---|---|
| P57780 | Alpha-actinin 4 (Non-muscle alpha-actinin 4) (F-actin cross linking protein) | HRPELIEYDK | 4.6 | 3.88 | 3.40 |
| P05201 | Aspartate aminotransferase, cytoplasmic (EC 2.6.1.1) (Transaminase A) | VNLGVGAYR | 6.3 | 7.49 | 7.02 |
| P05202 | Aspartate aminotransferase, mitochondrial precursor | ILIRPLYSNPPLNGAR | 19.5 | 13.18 | 12.08 |
| Q91V92 | ATP-citrate synthase (EC 2.3.3.8) (ATP-citrate (pro-S-)-lyase) (Citrate cleavage emzyme) | DGVYILDLAAK | 19.4 | 9.08 | 10.47 |
| P48975 | Actin, cytoplasmic 1 (Beta-actin). | SYELPDGQVITIGNER | 572.9 | 645.73 | 617.19 |
| P51881 | ADP, ATP carrier protein, fibroblast isoform | YFPTQALNFAFK | 125.4 | 120.20 | 121.35 |
| P05064 | Fructose-bisphosphate aldolase A (EC 4.1.2.13) | LQSIGTENTEENR | 99.8 | 119.89 | 88.97 |
| Q61024 | Asparagine synthetase [glutamine-hydrolyzing] (EC 6.3.5.4) | ELYLFDVLR | 19.4 | 5.70 | 5.09 |
| Q03265 | ATP synthase alpha chain, mitochondrial precursor | HALIIYDDLSK | 70.5 | 73.05 | 65.91 |
| P56480 | ATP synthase beta chain, mitochondrial precursor (EC 3.6.3.14) | VALTGLTVAEYFR | 79.8 | 88.57 | 69.58 |
| Q9DCX2 | ATP synthase D chain, mitochondrial (EC 3.6.3.14) | YTALVDQEEK | 13.1 | 13.35 | 13.91 |
| Q06647 | ATP synthase oligomycin sensitivity conferral protein | YATALYSAASK | 37.1 | 47.47 | 40.14 |
| Q91V12 | Cytosotic acyl coenzyme A thioester hydrolase (EC 3.1.2.2) | VLEVPPIVYLR | 10.8 | 15.80 | 12.60 |
| Q64433 | 10 kDa heat shock protein, mitochondrial (Hsp10) (10 kDa chaperonin) (CPN10) | DYFLFR | 41.0 | 20.14 | 20.19 |
| P11442 | Clathrin heavy chain. | ALEHFTDLYDIK | 26.1 | 49.56 | 48.33 |
| P18760 | Cofilin, non-muscle isoform | YALYDATYETK | 49.6 | 80.12 | 71.98 |
| P14211 | Calreticulin precursor (CRP55) (Calregulin) | FYALSAK | 54.2 | 37.71 | 31.45 |
| Q9JIK5 | Nucleolar RNA helicase II (Nucleolar RNA helicase | STYEQVDLIGK | 14.3 | ND | ND |
| Q91VC3 | Probable ATP-dependent helicase DDX48 (DEAD-box protein 48) | LDYGQHVVAGTPGR | 4.6 | ND | ND |
| Q62167 | DEAD-box protein 3 (DEAD-box RNA helicase DEAD3) (mDEAD3) (Embryonic RNA helicase) | YLVLDEADR | 6.8 | 3.17 | 3.20 |
| Q61656 | Probable RNA-dependent helicase p68 (DEAD-box protein p68) (DEAD-box protein 5) | NFYQEHPDLAR | 14.8 | ND | ND |
| O70133 | ATP-dependent RNA helicase A (Nuclear DNA helicase II) (NDH II) (DEAH-box protein 9) | DFVNYLVR | 9.7 | ND | 4.46 |
| Q62188 | Dihydropyrimidinase related protein-3 (DRP-3) | IFNLYPR | 14.3 | 22.74 | 23.42 |
| P20001 | Elongation factor 1-alpha 1 (EF-1-alpha-1) | EHALLAYTLGVK | 413.5 | 197.82 | 214.17 |

TABLE 13

| Accession number | Protein Name | Peptide sequence | Conc in Neuro2a (pmol/mg) | Conc in Brain wild type (pmol/mg) | Conc in Brain (ADAM22-ko) |
|---|---|---|---|---|---|
| Q9D8N0 | Elongation factor 1-gamma (EF-1-gamma) (eEF-1B gamma) | ALIAAQYSGAQVR | 30.2 | 20.04 | 17.66 |
| P58252 | Elongation factor 2 (EF-2). | GVQYLNEIK | 56.1 | 28.61 | 28.40 |
| Q60899 | ELAV-like protein 2 (Hu-antigen B) (HuB) (ELAV-like neuronel protein 1) | DANLYVSGLPK | 14.6 | ND | ND |
| P17182 | Alpha enolase (EC 4.2.1.11) | YITPDQLADLYK | 283.3 | 179.89 | 169.66 |
| P08113 | Endoplasmin precursor | GLFDEYGSK | 42.8 | 20.23 | 19.87 |
| P19096 | Fatty acid synthase (EC 2.3.1.85) | ELSFAAVSFYHK | 14.8 | 10.60 | 10.46 |
| Q61553 | Fascin (Singed-like protein) | YLAPSGPSGTLK | 11.4 | 9.33 | 12.33 |
| P16858 | Glyceraldehyde 3-phosphate dehydrogenase | YDNSLK | 190.0 | 202.87 | 198.56 |
| Q81598 | Rab GDP dissociation inhibitor beta-2 (Rab GDI beta-2) (GDI-3) | FLVYVANFDEK | 17.7 | 17.45 | 16.40 |
| O35501 | Stress-70 protein, mitochondrial precursor | VINEPTAAALAYGLDK | 92.6 | 42.92 | 45.03 |
| P07823 | 78 kDa glucose-regulated protein precursor (GRP 78) | NELESYAYSLK | 12.0 | 8.46 | 7.28 |
| P02304 | Histone H4 | ISGLIYEETR | 126.5 | 14.19 | 46.94 |
| Q63413 | Probable ATP-dependent RNA helicase p47 | LTLHGLQQYYVK | 41.2 | 24.86 | 18.31 |
| P19378 | Heat shock cognate 71 kDa protein. | SQIHDIVLVGGSTR | 390.5 | 317.10 | 278.82 |
| P07901 | Heat shock protein HSP 90-alpha (HSP 86) | HFSVEGQLEFR | 446.6 | 283.99 | 234.45 |
| P23116 | Eukaryotic translation Initiation factor 3 subunit 10 (elF-3 theta) (elF3 p167) | EEQHQLAVNAYLK | 9.1 | 6.16 | 5.83 |
| P03975 | IgE-blnding protein. | VHAPVEYLQIK | 58.2 | 18.83 | ND |
| Q8CAQ8 | Mitochondrial inner membrane protein (Mitofilin) | VEFEQGLSEK | 8.6 | ND | ND |
| P09055 | Integrin beta-1 precursor (Fibronectin receptor beta subunit) (CD29 antigen) | LPDGVTINYK | 3.4 | ND | ND |
| Q9D7G0 | Ribose-phosphate pyrophosphokinase I (EC 2.7.6.1) | VYAILTHGIFSGPAISR | 15.4 | 21.06 | 7.37 |
| P52480 | Pyruvate kinase, M2 isozyme (EC 2.7.1.40). | IYDDGLISLQVK | 102.4 | 53.96 | 72.35 |
| Q61881 | DNA replication licensing factor MCM7 (CDC47 homolog) | SQLLSYIDR | 3.4 | 1.23 | 1.90 |
| Q8VEM8 | Phosphate carrier protein, mitochondrial precursor | EEGLNAFYK | 22.8 | 21.93 | 22.95 |
| Q13126 | S-methyl-5-thioadenosine phosphorylase | YVDTPFGKPSDALILGK | 20.4 | ND | 9.77 |
| Q9JLT0 | Myosin heavy chain, nonmuscle type B | ELEAELEDER | 16.5 | 13.37 | 13.54 |
| P28656 | Nucleosome assembly protein 1-like 1 (NAP-1 related protein) (Brain protein DN38) | FYEEVHDLER | 16.5 | 8.01 | 7.97 |

TABLE 14

| Accession number | Protein Name | Peptide sequence | Conc in Neuro2a (pmol/mg) | Conc in Brain wild type (pmol/mg) | Conc in Brain (ADAM22-ko) |
|---|---|---|---|---|---|
| P09405 | Nucleolin (Protein C23) | FGYVDFESAEDLEK | 57.0 | 21.90 | 18.90 |
| Q60432 | 150 kDa oxygen-regulated protein precursor (Orp150) (Hypoxia up-regulated 1) | DAVIYPILVEFTR | 14.3 | 5.33 | 5.89 |
| P50580 | Proliferation-associated protein 2G4 (Proliferation-associated protein 1) | ITSGPFEPDLYK | 19.4 | 2.67 | ND |
| P29341 | Polyadenylate-binding protein 1 (Poly(A)-binding protein 1) (PABP 1) | SLGYAYVNFQQPADAER | 18.5 | 12.01 | 17.37 |
| P35700 | Peroxiredoxin 1 (EC 1.11.1.-) (Thioredoxin peroxidase 2) | DISLSEYK | 46.1 | 29.31 | 29.79 |
| Q61171 | Peroxiredoxin 2 (EC 1.11.1.-) (Thioredoxin peroxidase 1) | SLSQNYGVLK | 24.5 | 26.51 | 27.38 |
| O08807 | Peroxiredoxin 4 (EC 1.11.1.-) (Prx-IV) | LVQAFQYTDK | 34.2 | 16.69 | 15.74 |
| O08709 | Peroxiredoxin 6 (EC 1.11.1.-) (Antioxidant protein 2) (1-Cys peroxiredoxin) (1-Cys PRX) | LSILYPATTGR | 12.0 | 8.94 | 9.43 |
| P15331 | Peripherin. | YADLSDAANR | 39.7 | 15.99 | 8.49 |
| P50310 | Phosphoglycerate kinase (EC 2.7.2.3). | LGDVYVNDAFGTAHR | 14.3 | 19.13 | 16.29 |
| Q9DBJ1 | Phosphoglycerate mutase 1 (EC 5.4.2.1) | HGESAWNLENR | 54.2 | 82.05 | 72.57 |
| Q60932 | Voltage-dependent anion-selective channel protein | GYGFGLIK | 34.2 | 18.42 | 9.49 |
| Q60930 | Voltage-dependent anion-selective channel protein | VQLDPTASISAK | 25.7 | 29.68 | ND |
| Q60931 | Voltage-dependent anion-selective channel protein 3 (VDAC-3) (mVDAC3) | LSQNNFALGYK | 6.8 | 12.59 | ND |
| P97371 | Proteasome activator complex subunit 1 (Proteasome activator 28-alpha subunit) (PA28alpha) | TENLLGSYFPK | 9.1 | 4.97 | 3.17 |
| P46638 | Ras-related protein Rab-11B | NILTEIYR | 4.0 | 5.43 | 5.28 |
| P19253 | 60S ribosomal protein L13a | FAYLGR | 22.8 | 7.27 | ND |
| P17080 | GTP-binding nuclear protein RAN (TC4) (Ran GTPase) | NLQYYDISAK | 121.1 | 63.94 | 44.08 |
| P10113 | Ras-related protein Rap-1A (C21KG) (KREV-1 protein) (GTP-binding protein SMG-P21A) (G-22K) | INVNEIFYDLVR | 17.1 | 14.61 | 13.83 |
| Q60972 | Chromatin assembly factor 1 subunit C (CAF-1 subunit C) | TPSSDVLVFDYTK | 21.7 | ND | ND |
| Q91YQ5 | Dolichyl-diphosphooligosaccharide-protein glycosyltransferase 67 kDa subunit precursor | SEDVLDYGPFK | 8.0 | ND | ND |
| P39026 | 60S ribosomal protein L11. | YDGIILPGK | 51.3 | 18.12 | 25.62 |
| Q9CPR4 | 60S ribosomal protein L17 (L23). | YSLDPENPTK | 42.8 | 17.79 | ND |
| P41104 | 60S ribosomal protein L22 (Heparin binding protein HBp15) | ESYELR | 44.9 | 13.65 | 22.00 |
| P08526 | 60S ribosomal protein L27. | YSVDIPLDK | 40.7 | 13.52 | 10.36 |
| P04645 | 60S ribosomal protein L30 | YVLGYK | 18.2 | 8.08 | ND |

TABLE 15

| Accession number | Protein Name | Peptide sequence | Conc in Neuro2a (pmol/mg) | Conc in Brain wild type (pmol/mg) | Conc in Brain (ADAM22-ko) |
|---|---|---|---|---|---|
| Q9D1R9 | 60S ribosomal protein L34. | LSYNTASNK | 45.6 | 25.54 | 38.07 |
| P47911 | 60S ribosomal protein L6 (TAX-responsive enhancer element binding protein 107) (TAXREB107) | HLTDAYFK | 23.9 | 4.16 | ND |
| P14148 | 60S ribosomal protein L7. | SVNELIYK | 57.0 | 26.20 | ND |
| P14869 | 60S acidic ribosomal protein P0 (L10E). | SNYFLK | 48.5 | 44.63 | 35.60 |
| O35737 | Heterogeneous nuclear ribonucleoprotein H (hnRNP H) | ATENDIYNFFSPLNPVR | 58.9 | ND | 27.45 |
| Q7TMK9 | Heterogeneous nuclear ribonucleoprotein Q (hnRNP Q) (hnRNP-Q) | TGYTLDVTTGQR | 12.5 | ND | 10.49 |
| P09900 | 40S ribosomal protein S10 | IAIYELLFK | 31.4 | 5.88 | 6.99 |
| Q02546 | 40S ribosomal protein S13 | GLSQSALPYR | 23.4 | 10.70 | 9.49 |
| P17008 | 40S ribosomal protein S16. | DILIQYDR | 216.6 | 90.65 | 120.10 |
| P25444 | 40S ribosomal protein S2 (S4) (LLREP3 protein) | SPYQEFTDHLVK | 26.8 | 11.77 | 11.13 |
| P17073 | 40S ribosomal protein S3 | ELAEDGYSGVEVR | 35.3 | 10.15 | 21.28 |
| P97351 | 40S ribosomal protein S3a | TTDGVLLR | 30.2 | 4.81 | 27.53 |
| P47961 | 40S ribosomal protein S4. | YALTGDEVK | 77.0 | 23.93 | 26.87 |
| P09058 | 40S ribosomal protein S8. | ADGYVLEGK | 45.6 | 46.39 | 12.94 |
| P29314 | 40S ribosomal protein S9. | LDYILGLK | 64.1 | 26.92 | 32.36 |
| P43331 | Small nuclear ribonucleoprotein Sm D3 (snRNP core protein D3) (Sm-D3) | VAQLEQVYIR | 20.5 | 9.37 | 9.19 |
| P16086 | Spectrin alpha chain, brain (Spectrin, non-erythroid alpha chain) (Alpha-II spectrin) | LLVSSEDYGR | 3.4 | 7.16 | 6.65 |
| Q62261 | Spectrin beta chain, brain 1 (Spectrin, non-erythroid beta chain 1) (Beta-II spectrin) | ITDLYTDLR | 6.3 | 8.81 | 7.44 |
| Q99L47 | Hsc70-interacting protein (Hip) (Putative tumor suppressor ST13) | LAILYAK | 37.2 | 25.26 | 21.04 |
| Q922B2 | Aspartyt-tRNA synthetase (EC 6.1.1.12) (Aspartate-tRNA ligase) (AspRS) | IYVISLAEPR | 12.0 | 6.77 | 6.37 |
| Q9CZD3 | Glycyl-tRNA synthetase (EC 6.1.1.14) (Glycine-tRN | IYLYLTK | 36.7 | 13.01 | 20.94 |
| Q99MN1 | Lysyl-tRNA synthetase (EC 6.1.1.6) (Lysine-tRNA ligase) (LysRS) | LIFYDLR | 15.4 | 5.58 | 7.75 |
| P26638 | Seryl-tRNA synthetase (EC 6.1.1.11) (Serine-tRNA ligase) (SerRS) | YLIATSEQPIAALHR | 35.2 | 12.60 | 13.97 |
| Q9Z1Q9 | Valyl-tRNA synthetase 2 (EC 6.1.1.9) (Valine-tRNA ligase 2) (VaIRS 2) | TLLPVPGYK | 8.0 | 6.24 | 7.99 |
| Q9WVA4 | Transgelin 2. | GPSYGLSR | 61.6 | 13.52 | 16.00 |
| P05213 | Tubulin alpha-2 chain (Alpha-tubulin 2). | AVFVDLEPTVIDEVR | 846.5 | 2073.10 | 2956.75 |

TABLE 16

| Accession number | Protein Name | Peptide sequence | Conc in Neuro2a (pmol/mg) | Conc in Brain wild type (pmol/mg) | Conc in Brain (ADAM22-ko) |
|---|---|---|---|---|---|
| P05218 | Tubulin beta-5 chain | YLTVAAVFR | 319.2 | 682.98 | 653.04 |
| P11983 | T-complex protein 1, alpha subunit B (TCP-1-alpha) | YPVNSVNILK | 17.1 | 8.79 | 9.09 |
| P80315 | T-complex protein 1, delta subunit (TCP-1-delta) (CCT-delta) (A45) | AYILNLVK | 32.1 | 15.72 | 17.33 |
| P42932 | T-complex protein 1, theta subunit (TCP-1-theta) | QYGSETFLAK | 45.6 | 27.77 | 25.21 |
| Q62318 | Transcription Intermediary factor 1-beta (TIF1-beta) (Tripartite motif protein 28) | DHQYQFLEDAVR | 7.4 | 4.29 | 4.48 |
| Q01320 | DNA topoisomerase II, alpha isozyme (EC 5.99.1.3). | TPSLITDYR | 17.1 | ND | ND |
| Q9CQM9 | Thioredoxin-like protein 2 | YEISSVPTFLFFK | 6.8 | ND | 5.95 |
| Q08810 | 116 kDa U5 small nuclear ribonucleoprotein component (U5 snRNP-specific protein, 116 kDa) | SFVEFILEPLYK | 156.8 | ND | ND |
| Q9DB77 | Ubiquinol-cytochrome C reductase complex core protein 2, mitochondrial precursor | IIENLHDVAYK | 8.0 | ND | ND |
| P20152 | Vimentin. | SLYSSSPGGAYVTR | 159.6 | 50.35 | 55.24 |

Table 12 to Table 16: It is shown results of measurement of the absolute quantity of each protein in the wild type mouse brain and the ADAM22 gene deficient mouse brain.

As mentioned above, by absolutely quantitating each protein in the cell containing the internal standard substance that was the metabolically isotope labeled biological molecule, it was possible to quantitate biological molecules absolutely and comprehensively.

INDUSTRIAL APPLICABILITY

According to the present invention, one or a plurality of biological molecules in a sample that cannot be labeled metabolically (for instance, tissue, biological fluid, cell, cell organ, protein complex and the like) can be quantitated with good accuracy.

That is to say, a conventional in vivo labeling method could only be performed in limited cells, such as those not influenced by a culture condition; however, in the present invention, since an internal standard substance that is a metabolically isotope labeled biological molecule or a cell containing an internal standard substance that is a metabolically isotope labeled biological molecule has been added to a sample, one or a plurality of biological molecules in the sample that cannot be labeled metabolically (for instance, tissue, biological fluid, cell, cell organ, protein complex and the like) can be quantitated, without limiting to cells that can be cultured.

In addition, with a conventional in vitro labeling method, the variation of quantitative value at each experiment in the pretreatment stage, such as sample digestion, fractionation and purification could not be corrected; however, in the present invention, since an internal standard substance that is a metabolically isotope labeled biological molecule or a cell containing an internal standard substance that is a metabolically isotope labeled biological molecule is added prior to carrying out sample digestion, fractionation, purification and the like, one or a plurality of biological molecules in a sample can be quantitated with good accuracy.

According to the present invention, comparison among three or more samples has become easy. That is to say, quantitative proteome analysis method so far has been directly comparing an internal standard substance and a test sample, such that sample preparation has to be carried out at each measurement. In addition, when the subject to be measured changes, an internal standard substance to be labeled also changes, such that each time, labeling conditions has to be examined, in addition, comparison between experiments is not possible; however, with the present invention, by conserving and adequately using an internal standard substance that is a metabolically isotope labeled biological molecule or a cell containing an internal standard substance that is a metabolically isotope labeled biological molecule, comparison of data between experiments, for instance, obtaining comparative data after a given time lapse (for instance, after one month, after one year, etc.) and analyzing against existing experimental data, becomes possible. Furthermore, by transferring or lending the internal standard substance that is the metabolically isotope labeled biological molecule or the cell containing the internal standard substance that is the metabolically isotope labeled biological molecule used, until now impossible data comparison between investigators, which was not possible so far, becomes possible.

According to the present invention, by calculating beforehand a concentration of an internal standard substance that is a metabolically isotope labeled biological molecule or a biological molecule in a cell containing an internal standard substance that is a metabolically isotope labeled biological molecule, absolute quantitation of the biological molecule is possible. By transferring or lending the internal standard substance that is the metabolically isotope labeled biological molecule or the cell containing the internal standard substance that is the metabolically isotope labeled biological molecule, data sharing between investigators becomes possible.

Furthermore, according to the analysis device and analysis method of the present invention, a mass spectrum derived from an individual biological molecule can be obtained, and quantitatively analyzing the amount of biological molecule expressed in a cell inside an organism, which varies sometimes constantly, becomes possible. In addition, according to a program of the present invention, the previous analysis method can be implemented in a computer.

In addition, according to the present invention, association of a quantitative value that is (non-isotope labeled protein)/(isotope labeled protein) in a protein and a functional information becomes possible.

With a conventional method (AQUA method), since a synthetic peptide is added to a sample, quantitative values could not be obtained with good accuracy, due to a low protein recovery rate in the fractionation, extraction, purification and digestion (in particular in-gel digestion) steps. On the other hand, with the method of the present invention, since an internal standard substance that is a metabolically isotope labeled biological molecule or a cell containing an internal standard substance that is a metabolically isotope labeled biological molecule is added to a sample, highly reproducible quantitative value can be obtained with good accuracy, without being influenced by the protein recovery rate in the fractionation, extraction, purification and digestion (in particular in-gel digestion) steps.

In addition, in a conventional method, as a synthetic peptide is added to a sample, peptides that can be quantitated are limited to peptides having a sequence that is identical to the synthetic peptide. Therefore, influence on the quantitative value of the protein becomes large, due to errors in the results of peptide measurement. On the other hand, in the method of the present invention, a biological molecule in an internal standard substance that is a metabolically isotope labeled biological molecule or a cell containing an internal standard substance that is a metabolically isotope labeled biological molecule is quantitated, and the internal standard substance that is the metabolically isotope labeled biological molecule or the cell containing the internal standard substance that is the metabolically isotope labeled biological molecule is added to a sample; therefore, peptides that can be quantitated are not limited to peptides having a sequence that is identical to the synthetic peptide, and other peptides derived from a protein that the peptide was constituting can also be quantitated. Therefore, one protein can be quantitated via a plurality of peptides, such that a highly reproducible quantitative value can be obtained with good accuracy, without a large influence on the quantitative value of the protein due to errors in the results of individual peptide measurement.

Furthermore, a peptide synthesizer employs 10-fold excess amounts of reagents, and moreover, the synthesis scale is from microgram to milligram units. Therefore, synthesis of an isotope labeled peptide becomes extremely expensive, and a comprehensive quantitating with a conventional method is difficult from the viewpoint of costs. On the other hand, with the method of the present invention, isotope labeling of the biological molecule is carried out by a cell culture, such that production is possible with good efficiency even for small quantities. In addition, as the synthetic peptide for quantitating a biological molecule in an internal standard substance that is a metabolically isotope labeled biological molecule or a cell containing an internal standard substance that is a metabolically isotope labeled biological molecule can be handled with ordinary peptide synthesis that does not require an isotope, it is suited for a comprehensive quantitation method.

We claim:

1. A method for quantitating a known biological molecules in a sample, comprising the steps of:
    obtaining a cell containing an internal standard substance that is a metabolically labeled biological molecule by culturing a cell derived from the same species and same tissue as the sample in a culture medium comprising an isotope labeled precursor of the biological molecule;
    adding the obtained cell to the sample
    extracting and fractionating the biological molecule from the sample; and
    determining, using a mass spectrometer device, a ratio of intensities between a labeled peak and an unlabeled peak of the fractionated biological molecule to quantitate the biological molecule in the sample.

2. The method according to claim 1, wherein the biological molecule in the internal standard substance that is the metabolically isotope labeled biological molecule, or in the cell containing the internal standard substance that is the metabolically isotope labeled biological molecule, is present in a known quantity.

3. The method according to claim 1, wherein the quantitation is an absolute quantitation.

4. The method according to claim 1, wherein the sample is a sample that is unable to be labeled metabolically.

5. The method according to claim 1, wherein the biological molecule is a molecule selected from the group consisting of a protein, a lipid, a sugar chain, and a nucleic acid.

6. The method according to claim 1, wherein the biological molecule is a protein and wherein the method further comprises the steps of: extracting and fractionating the protein; and digesting the protein.

7. The method according to claim 1, wherein the sample is a sample selected from the group consisting of a tissue, a biological fluid, a cell, a cell organ and a protein complex.

8. The method according to claim 1, wherein the isotope is an isotope selected from the group consisting of $^{2}H$, $^{13}C$, $^{15}N$, $^{17}O$, $^{18}O$, $^{33}P$, $^{34}S$, and combinations thereof.

* * * * *